(12) United States Patent
Prassler et al.

(10) Patent No.: US 8,206,977 B2
(45) Date of Patent: Jun. 26, 2012

(54) TRICISTRONIC VECTORS AND USES THEREFOR

(75) Inventors: Josef Prassler, Germering (DE); Yvonne Stark, Munich (DE)

(73) Assignee: MorphoSys AG (DE)

( * ) Notice: Subject to any disclaimer, the term of this patent is extended or adjusted under 35 U.S.C. 154(b) by 960 days.

(21) Appl. No.: 10/522,535

(22) PCT Filed: Jul. 30, 2003

(86) PCT No.: PCT/IB03/03681
§ 371 (c)(1), (2), (4) Date: Oct. 12, 2005

(87) PCT Pub. No.: WO2004/013276
PCT Pub. Date: Feb. 12, 2004

(65) Prior Publication Data
US 2006/0121563 A1    Jun. 8, 2006

Related U.S. Application Data

(60) Provisional application No. 60/399,150, filed on Jul. 30, 2002.

(51) Int. Cl.
*C12N 15/13* (2006.01)
*C12P 21/02* (2006.01)

(52) U.S. Cl. .................................... 435/320.1; 435/69.6

(58) Field of Classification Search ........................ None
See application file for complete search history.

(56) References Cited

U.S. PATENT DOCUMENTS
2002/0034733 A1 * 3/2002 Lohning ........................... 435/5

FOREIGN PATENT DOCUMENTS
WO    WO 91/17271    11/1991
WO    WO 98/11241    3/1998

OTHER PUBLICATIONS

Burger et al., Appl. Microbiol Biotechnol (1999) 52:345-353.*
Kozak, Microbiological Reviews, 47 (1), 1-45, 1983.*
Crameri et al., "Display of biologically active proteins on the surface of filamentous phages: a cDNA cloning system . . . ." Gene, 137:69-75 (1993).
Mielke et al., "Stabilized, long-term expression of heterodimeric proteins from tricistronic mRNA" Gene 254:1-8 (2000).
Brinkmann, et al.: "Phage display of disulfide-stabilized Fv fragments", Journal of Immunological Methods 182 (1995) 41-50.
Hannig, et al.: "Tricistonic recombinant adenovirus expressing clone specific immunoglobulin and enhanced green fluoresecent protein (EGFP) as genetransfer vector for immunotherapy in Non-Hodgkin lymphoma", Gene Transfer—biology and Marketing Studies (2000), Abstract # 5396.

* cited by examiner

*Primary Examiner* — Nancy Vogel

(57) ABSTRACT

A tricistronic vector (i.e., a vector capable of expressing three exogenous genes, which are not fused together, under the control of one promoter) effectively can encode an immunoglobulin-presenting polypeptide and two immunoglobulin (Ig) polypeptides. The encoded Ig-presenting polypeptide is able to associate with at least one of the Ig polypeptides via co-expressed associating agents. A vector according to the present invention particularly is suited for phage display technology, e.g., when the Ig-presenting polypeptide is a phage coat protein and the Ig polypeptides associate to form a Fab.

13 Claims, 25 Drawing Sheets

FIG. 2B-1

```
                                        HuCAL rev 100.0%
                                        ------------------------
1501 GGAGCGGAGG CGCGCCGCAC CATCATCACC ATCACTGCTG ATAAGCTTGA CCTGTGAAGT GAAAAATGGC GCAGATTGTG CGACATTTTT TTTGTCTGCC
     CCTCGCCTCC GCGCGGCGTG GTAGTAGTGG TAGTGACGAC TATTCGAACT GGACACTTCA CTTTTTACCG CGTCTAACAC GCTGTAAAAA AAACAGACGG
1601 GTTTAATGAA ATTGTAAACG TTAATATTTT GTTAAAATTC GCGTTAAATT TTTGTTAAAT CAGCTCATTT TTTAACCAAT AGGCCGAAAT CGGCAAAATC
     CAAATTACTT TAACATTTGC AATTATAAAA CAATTTTAAG CGCAATTTAA AAACAATTTA GTCGAGTAAA AAATTGGTTA TCCGGCTTTA GCCGTTTTAG
1701 CCTTATAAAT CAAAAGAATA GACCGAGATA GGGTTGAGTG TTGTTCCAGT TTGGAACAAG AGTCCACTAT TAAAGAACGT GGACTCCAAC GTCAAAGGGC
     GGAATATTTA GTTTTCTTAT CTGGCTCTAT CCCAACTCAC AACAAGGTCA AACCTTGTTC TCAGGTGATA TTTCTTGCA CCTGAGGTTG CAGTTTCCCG
1801 GAAAAACCGT CTATCAGGGC GATGGCCCAC TACCGAGAAC ATCACCCTAA TCAAGTTTTT TGGGGTCGAG GTGCCGTAAA GCACTAAATC GGAACCCTAA
     CTTTTTGGCA GATAGTCCCG CTACCGGGTG ATGCTCTTGG TAGTGGGATT AGTTCAAAAA ACCCCAGCTC CACGGCATTT CGTGATTTAG CCTTGGGATT
1901 AGGGAGCCCC CGATTTAGAG CTTGACGGGG AAAGCGGACG AACGTGGCGA GAAAGGAAGG GAAGAAAGCG AAAGGAGCGG GCGCTAGGGC GCTGGCAAGT
     TCCCTCGGGG GCTAAATCTC GAACTGCCCC TTTCGGCCGC TTGCACCGCT CTTTCCTTCC CTTCTTTCGC TTTCCTCGCC CGCGATCCCG CGACCGTTCA
                                                   NheI
                                                   ------
2001 GTAGCGGTCA CGCTGCGCGT AACCACCACA CCCGCCGCGC TTAATGCGCC GCTACAGGGC GCGTGCTAGC CATGTGAGCA AAAGGGCAGC AAAAGGCCAG
     CATCGCCAGT GCGACGCGCA TTGGTGGTGT GGGCGGCGCG AATTACGCGG CGATGTCCCG CGCACGATCG GTACACTCGT TTTCCGTCG TTTTCCGGTC
2101 GAACCGTAAA AAGGCCGCGT TGCTGGCGTT TTTCCATAGG CTCCGCCCCC CTGACGAGCA TCACAAAAAT CGACGCTCAA GTCAGAGGTG GCGAAACCGG
     CTTGGCATTT TTCCGGCGCA ACGACCGCAA AAAGGTATCC GAGGCGGGGG GACTGCTCGT AGTGTTTTTA GCTGCGAGTT CAGTCTCCAC GCTTTGGGC
2201 ACAGGACTAT AAAGATACCA GGCGTTTCCC CCTGGAAGCT CCCTCGTGCG CTCTCCTGTT CCGACCCTGC CGCTTACCGG ATACCGTCC GCCTTTCTCC
     TGTCCTGATA TTTCTATGGT CCGCAAAGGG GGACCTTCGA GGGAGCACGC GAGAGGACAA GGCTGGGACG GCGAATGGCC TATGGACAGG CGGAAAGAGG
2301 CTTCGGGAAG CGTGGCGCTT TCTCATAGCT CACGCTGTAG GTATCTCAGT TCGGTGTAGG TCGTTCGCTC CAAGCTGGGC TGTGTGCACG AACCCCCCGT
     GAAGCCCTTC GCACCGCGAA AGAGTATCGA GTGCGACATC CATAGAGTCA AGCCACATCC AGCAAGCGAG GTTCGACCCG ACACACGTGC TTGGGGGGCA
2401 TCAGTCCGAC CGCTGCGCCT TATCCGGTAA CTATCGTCTT GAGTCCAACC CGGTAAGACA CGACTTATCG CGCTGAATAGC GGTGACCGTC GTCGGTGACC ATTGTCCTAA
     AGTCAGGCTG GCGACGCGGA ATAGGCCATT GATAGCAGAA CTCAGGTTGG GCCATTCTGT GCTGAATAGC GGTGACCGTC GTCGGTGACC ATTGTCCTAA
2501 AGCAGAGCGA GGTATGTAGG CGGTGCTACA GAGTTCTTGA AGTGGTGGCC TAACTACGGC TACACTAGAA GAACAGTATT TGGTATCTGC GCTCTGCTGT
     TCGTCTCGCT CCATACATCC GCCACGATGT CTCAAGAACT TCACCACCGG ATTGATGCCG ATGTGATCTT CTTGTCATAA ACCATAGACG CGAGACGACA
2601 AGCCAGTTAC CTTCGGAAAA AGAGTTGGTA GCTCTTGATC CGGCAAACAA ACCACCGCTG GTAGCGGTGG TTTTTTTGTT TGCAAGCAGC AGATTACGCG
     TCGGTCAATG GAAGCCTTTT TCTCAACCAT CGAGAACTAG GCCGTTTGTT TGGTGGCGAC CATCGCCACC AAAAAAACAA ACGTTCGTCG TCTAATGCGC
                                                   BglII
                                                   -----
2701 CAGAAAAAAA GGATCTCAAG AAGATCCTTT GATCTTTTCT ACGGGGTCTG ACGCTCAGTG GAACGAAAAC TCACGTTAAG GGATTTTGGT CAGATCTAGC
     GTCTTTTTTT CCTAGAGTTC TTCTAGGAAA CTAGAAAAGA TGCCCCAGAC TGCGAGTCAC CTTGCTTTTG AGTGCAATTC CCTAAAACCA GTCTAGATCG
2801 ACCAGGCGTT TAAGGGCACC AATAACTGCC TTAAAAAAAT TACGCCCCGC CCTGCCACTC ATCGCAGTAC TGTTGTAATT CATTAAGCAT TCTGCCGACA
     TGGTCCGCAA ATTCCCGTGG TTATTGACGG AATTTTTTTA ATGCGGGGCG GGACGGTGAG TAGCGTCATG ACAACATTAA GTAATTGTA AGACGGCTGT
2901 TGGAAGCCAT CACAAACGGC ATGATGAACC TGAATCGCCA GCGGCATCAG CACCTTGTCG CCTTGCGTAT AATATTTGCC CATAGTGAAA ACGGGGGCGA
     ACCTTCGGTA GTGTTTGCCG TACTACTTGG ACTTAGCGGT CGCCGTAGTC GTGGAACAGC GGAACGCATA TTATAAACGG GTATCACTTT TGCCCCGCT
3001 AGAAGTTGTC CATATTGGCT ACGTTTAAAT CAAAACTGGT GAAACTCACC CAGGGATTGG CTGAGACGAA AAACATATTC TCAATAAACC CTTTAGGGAA
     TCTTCAACAG GTATAACCGA TGCAAATTTA GTTTTGACCA CTTTGAGTGG GTCCCTAACC GACTCTGCTT TTTGTATAAG AGTTATTTGG GAAATCCCTT
3101 ATAGGCCAGG TTTTCACCGT AACACGCCAC ATCTTGCGAA TATATGTGTA GAAACTGCCG GAAATCGTCG TGGTATTCAC TCCAGAGCGA TGAAAACGTT
     TATCCGGTCC AAAAGTGGCA TTGTGCGGTG TAGAACGCTT ATATACACAT CTTTGACGGC CTTTAGCAGC ACCATAAGTG AGGTCTCGCT ACTTTTGCAA
3201 TCAGTTTGCT CATGGAAAAC GGTGTAACAA GGGTGAACAC TATCCCATAT CACCAGCTCA CCGTCTTTCA TTGCCATACG GAACTCGGG TGAGCATTCA
     AGTCAAACGA GTACCTTTTG CCACATTGTT CCCACTTGTG ATAGGGTATA GTGGTCGAGT GGCAGAAAGT AACGGTATGC CTTGAGGCCC ACTCGTAAGT
3301 TCAGGCGGGC AAGAATGTGA ATAAAGGCCG GATAAACTTT GTGCTTATTT TTCTTTACGG TCTTTAAAAA GGCCGTAATA TCCAGCTGAA CGGTCTGGTT
     AGTCCGCCCG TTCTTACACT TATTTCCGGC CTATTTTGAA CACGAATAAA AAGAAATGCC AGAAATTTTT CCGGCATTAT AGGTCGACTT GCCAGACCAA
3401 ATAGGTACAT TGAGCAACTG ACTGAAATGC CTCAAAATGT TCTTTACGAT GCCATTGGGA TATATCAACG GTGGTATATC CAGTGATTTT TTCTCCATT
     TATCCATGTA ACTCGTTGAC TGACTTTACG GAGTTTTACA AGAAATGCTA CGGTAACCCT ATATAGTTGC CACCATATAG GTCACTAAAA AAGAGGTAA
                                                   AatII
                                                   -----
3501 TTAGCTTCCT TAGCTCCTGA AAATCTCGAT AACTCAAAAA ATACGCCCGG TAGTGATCTT ATTTCATTAT GGTGAAAGTT GGAACCTCAC CCGACGTCTA
     AATCGAAGGA ATCGAGGACT TTAGAGCTA TTGAGTTTTT TATGCGGGCC ATCACTAGAA TAAAGTAATA CCACTTTCAA CCTTGGAGTG GGCTGCAGAT
                                                   M13 rev 100.0%
                                                   --------------
```

FIG. 2B-2

```
3601 ATGTGAGTTA GCTCACTCAT TAGGCACCCC AGGCTTTACA CTTTATGCTT CCGGCTCGTA TGTTGTGTGG AATTGTGAGC GGATAACAAT TTCACACAGG
     TACACTCAAT CGAGTGAGTA ATCCGTGGGG TCCGAAATGT GAAATACGAA GGCCCAGCAT ACAACACACC TTAACACTCG CCTATTGTTA AAGTGTGTCC
     M13 rev 100.0%
     --------------
3701 AAACAGCTAT GACCATGATT ACGAATTTCT AGTATACGAG GCAAAAAAT GAAAAAACTG CTGTTCGCGA TTCCGCTGGT GGTGCCGTTC TATAGCCATA
     TTTGTCGATA CTGGTACTAA TGCTTAAAGA TCATATGCTC CCGTTTTTTA CTTTTTTGAC GACAAGCGCT AAGGCGACCA CCACGGCAAG ATATCGGTAT
3801 GCGACTACTG CGACATCGAG TTTGCAGAAA CAGTTGAAAG TTGTTTAGCA AAACCCCATA CAGAAAATTC ATTTACTAAC GTCTGGAAAG ACGACAAAAC
     CGCTGATGAC GCTGTAGCTC AAACGTCTTT GTCAACTTTC AACAAATCGT TTTGGGGTAT GTCTTTTAAG TAAATGATTG CAGACCTTTC TGCTGTTTTG
3901 TTTAGATCGT TACGCTAACT ATGAGGGCTG TCTGTGGAAT GCTACAGGCG TTGTAGTTTG TACTGGTGAC GAAACTCAGT GTTACGGTAC ATGGGTTCCT
     AAATCTAGCA ATGCGATTGA TACTCCCGAC AGACACCTTA CGATGTCCGC AACATCAAAC ATGACCACTG CTTTGAGTCA CAATGCCATG TACCCAAGGA
4001 ATTGGGCTTG CTATCCCTGA AAATGAGGGT GGTGGCTCTG AGGGTGGCGG TTCTGAGGGT GGCGGCTCTG AGGGTGGCGG TACTAAACCT CCTGAGTACG
     TAACCCGAAC GATAGGGACT TTTACTCCCA CCACCGAGAC TCCCACCGCC AAGACTCCCA CCGCCGAGAC TCCCACCGCC ATGATTTGGA GGACTCATGC
4101 GTGATACACC TATTCCGGGC TATACTTATA TCAACCCTCT CGACGGCACT TATCCGCCTG GTACTGAGCA AAACCCCGCT AATCCTAATC CTTCTCTTGA
     CACTATGTGG ATAAGGCCCG ATATGAATAT AGTTGGGAGA GCTGCCGTGA ATAGGCGGAC CATGACTCGT TTTGGGGCGA TTAGGATTAG GAAGAGAACT
4201 GGAGTCTCAG CCTCTTAATA CTTTCATGTT TCAGAATAAT AGGTTCCGAA ATAGGCAGGG GCATTAACT GTTTATACGG GCACTGTTAC TCAAGGCACT
     CCTCAGAGTC GGAGAATTAT GAAAGTACAA AGTCTTATTA TCCAAGGCTT TATCCGTCCC CGTAATTGA CAAATATGCC CGTGACAATG AGTTCCGTGA
4301 GACCCCGTTA AAACTTATTA CCAGTACACT CCTGTATCAT CAAAAGCCAT GTATGACGCT TACTGGAACG GTAAATTCAG AGACTGCGCT TTCCATTCTG
     CTGGGGCAAT TTTGAATAAT GGTCATGTGA GGACATAGTA GTTTTCGGTA CATACTGCGA ATGACCTTGC CATTTAAGTC TCTGACGCGA AAGGTAAGAC
4401 GCTTTAATGA GGATCCATTC GTTTGTGAAT ATCAAGGCCA ATCGTCTGAC CTGCCTCAAC CTCCTGTCAA TGCTGGCGGC GGCTCTGGTG GTGGTTCTGG
     CGAAATTACT CCTAGGTAAG CAAACACTTA TAGTTCCGGT TAGCAGACTG GACGGAGTTG GAGGACAGTT ACGACCGCCG CCGAGACCAC CACCAAGACC
4501 TGGCGGCTCT GAGGGTGGCG GCTCTGAGGG TGGCGGTTCT GAGGGTGGCG GCTCTGAGGG TGGCGGTTCC GGTGGCGGCT CCGGTTCCGG TGATTTTGAT
     ACCGCCGAGA CTCCCACCGC CGAGACTCCC ACCGCCAAGA CTCCCACCGC CGAGACTCCC ACCGCCAAGG CCACCGCCGA GGCCAAGGCC ACTAAAACTA
4601 TATGAAAAAA TGGCAAACGC TAATAAGGGG CTATGACCG AAAATGCCGA TGAAACGCG CTACAGTCTG ACGCTAAAGG CAAACTTGAT TCTGTCGCTA
     ATACTTTTTT ACCGTTTGCG ATTATTCCCC CGATACTGGC TTTTACGGCT ACTTTTGCGC GATGTCAGAC TGCGATTTCC GTTGAACTA AGACAGCGAT
4701 CTGATTACGG TGCTGCTATC GATGGTTTCA TTGGTGACGT TTCCGGCCTT GCTAATGGTA ATGGTGCTAC TGGTGATTTT GCTGGCTCTA ATTCCCAAAT
     GACTAATGCC ACGACGATAG CTACCAAAGT AACCACTGCA AAGGCCGGAA CGATTACCAT TACCACGATG ACCACTAAAA CGACCGAGAT TAAGGGTTTA
4801 GGCTCAAGTC GGTGACGGTG ATAATTCACC TTTAATGAAT AATTTCCGTC AATATTTACC TTCTTTGCCT CAGTCGGTTG AATGTCGCCC TTATGTCTTT
     CCGAGTTCAG CCACTGCCAC TATTAAGTGG AAATTACTTA TTAAAGGCAG TTATAAATGG AAGAAACGGA GTCAGCCAAC TTACAGGGGG AATACAGAAA
4901 GGCGCTGGTA AACCATATGA ATTTTCTATT GATTGTGACA AAATAAACTT ATTCCGTGGT GTCTTTGCGT TTCTTTTATA TGTTGCCACC TTTATGTATG
     CCGCGACCAT TTGGTATACT TAAAAGATAA CTAACACTGT TTATTTGAA TAAGGCACCA CAGAAACGCA AAGAAAATAT ACAACGGTGG AAATACATAC
                                                              XbaI
                                                               -
                                                              AflII
                                                             -------
5001 TATTTTCGAC GTTTGCTAAC ATACTGCGTA ATAAGGAGTC TTAAGTAAT
     ATAAAAGCTG CAAACGATTG TATGACGCAT TATTCCTCAG AATTCATTA
```

FIG. 2B-3

```
tctagagcatgcgtaggagaaaataaaatgaaacaaagcactattgcactggcactcttaccgttgctcttcacccctgttaccaaa
gccgactacaaagatgaagtgcaattgaaagaaagcggcccggccctggtgaaaccgacccaaaccctgaccctgacctgtacct
tttccggatttagcctgtccacgtctggcgttggcgtgggctggattcgccagccgcctgggaaagccctcgagtggctggctctgat
tgattgggatgatgataagtattatagcaccagcctgaaaacgcgtctgaccattagcaaagatacttcgaaaaatcaggtggtgct
gactatgaccaacatggacccggtggatacggccacctattattgcgcgcgttttgatcctttttttgattcttttttttgattattggggc
caaggcaccctggtgacggttagctcagcgggtggcggttctggcggcggtgggagcggtggcggtggttctggcggtggtggtt
ccgatatcgtgctgacccagccgccttcagtgagtggcgcaccaggtcagcgtgtgaccatctcgtgtagcggcagcagcagcaac
attggcagcaactatgtgagctggtaccagcagttgcccgggacggcgccgaaactgctgatttatgataacaaccagcgtccctc
aggcgtgccggatcgttttagcggatccaaaagcggcaccagcgcgagccttgcgattacgggcctgcaaagcgaagacgaagc
ggattattattgccagagctatgaccagaatgctcttgttgaggtgtttggcggcggcacgaagttaaccgttcttggccaggaattc
gagcagaagctgatctctgaggaggatctgaactagggtggtggctctggttccggtgatttgattatgaaaagatggcaaacgc
taataaggggggctatgaccgaaaatgccgatgaaaacgcgctacagtctgacgctaaaggcaaacttgattctgtcgctactgatt
acggtgctgctatcgatggtttcattggtgacgtttccggccttgctaatggtaatggtgctactggtgattttgctggctctaattccc
aaatggctcaagtcggtgacggtgataattcaccttaatgaataatttccgtcaatatttaccttccctccctcaatcggttgaatgtc
gcccttttgtcttggcgctggtaaaccatatgaattttctattgattgtgacaaaataaacttattccgtggtgtctttgcgtttctttat
atgttgccacctttatgtatgtattttctacgtttgctaacatactgcgtaataaggagtcttgataagcttgacctgtgaagtgaaaaa
tggcgcagattgtgcgacatttttttttgtctgccgtttaatgaaattgtaaacgttaatattttgttaaaattcgcgttaaattttgttaa
atcagctcatttttaaccaataggccgaaatcggcaaaatcccttataaatcaaaagaatagaccgagatagggttgagtgttgttc
cagtttggaacaagagtccactattaaagaacgtggactccaacgtcaaagggcgaaaaccgtctatcagggcgatggcccact
acgagaaccatcaccctaatcaagttttttgggggtcgaggtgccgtaaagcactaaatcggaaccctaaagggagccccgattta
gagcttgacggggaaagccggcgaacgtggcgagaaaggaagggaagaaagcgaaaggagcgggcgctagggcgctggca
agtgtagcggtcacgctgcgcgtaaccaccacacccgccgcgcttaatgcgccgctacagggcgcgtgctagccatgtgagcaaa
aggccagcaaaaggccaggaaccgtaaaaaggccgcgttgctggcgtttttccataggctccgcccccctgacgagcatcacaaa
aatcgacgctcaagtcagaggtggcgaaacccgacaggactataaagataccaggcgtttccccctggaagctccctcgtgcgctc
tcctgttccgaccctgccgcttaccggatacctgtccgcctttctcccttcgggaagcgtggcgctttctcatagctcacgctgtaggta
tctcagttcggtgtaggtcgttcgctccaagctgggctgtgtgcacgaaccccccgttcagtccgaccgctgcgccttatccggtaact
atcgtcttgagtccaacccggtaagacacgacttatcgccactggcagcagccactggtaacaggattagcagagcgaggtatgta
ggcggtgctacagagttcttgaagtggtggcctaactacggctacactagaagaacagtatttggtatctgcgctctgctgtagcca
gttaccttcggaaaaagagttggtagctcttgatccggcaaacaaaccaccgctggtagcggtggtttttttgtttgcaagcagcag
attacgcgcagaaaaaaggatctcaagaagatcctttgatcttttctacggggtctgacgctcagtggaacgaaaactcacgttaa
gggattttggtcagatctagcaccaggcgtttaagggcaccaataactgccttaaaaaaattacgccccgccctgccactcatcgca
gtactgttgtaattcattaagcattctgccgacatggaagccatcacaaacggcatgatgaacctgaatcgccagcggcatcagcac
cttgtcgccttgcgtataatatttgcccatagtgaaaacggggcgaagaagttgtccatattggctacgtttaaatcaaaactggtg
aaactcacccagggattggctgagacgaaaaacatattctcaataaacccttagggaaataggccaggttttcaccgtaacacgc
cacatcttgcgaatatatgtgtagaaactgccggaaatcgtcgtggtattcactccagagcgatgaaaacgtttcagtttgctcatgg
aaaacggtgtaacaagggtgaacactatcccatatcaccagctcaccgtctttcattgccatacggaactccgggtgagcattcatc
aggcgggcaagaatgtgaataaaggccggataaaacttgtgcttattttctttacggtctttaaaaaggccgtaatatccagctga
acggtctggttataggtacattgagcaactgactgaaatgcctcaaaatgttctttacgatgccattgggatatatcaacggtggtat
atccagtgatttttttctccatttttagcttccttagctcctgaaaatctcgataactcaaaaaatacgcccggtagtgatcttatttcatta
tggtgaaagttggaacctcacccgacgtctaatgtgagttagctcactcattaggcaccccaggctttacactttatgcttccggctcg
tatgttgtgtggaattgtgagcggataacaatttcacacaggaaacagctatgaccatgattacgaatt
```

FIG. 4D

```
ctagataacgagggcaaaaaatgaaaaagacagctatcgcgattgcagtggcactggctggtttcgctaccgtagcg
caggccgactactgcgatatcgagtttgcagaaacagttgaaagttgtttagcaaaacccccatacagaaaattcattta
ctaacgtctggaaagacgacaaaactttagatcgttacgctaactatgagggctgtctgtggaatgctacaggcgttgt
agtttgtactggtgacgaaactcagtgttacggtacatgggttcctattgggcttgctatccctgaaaatgagggtggtg
gctctgagggtggcggttctgagggtggcggctctgagggtggcggtactaaacctcctgagtacggtgatacaccta
ttccgggctatacttatatcaaccctctcgacggcacttatccgcctggtactgagcaaaacccgctaatcctaatccttc
tcttgaggagtctcagcctcttaatactttcatgtttcagaataataggttccgaaataggcaggggcattaactgttta
tacgggcactgttactcaaggcactgaccccgttaaaacttattaccagtacactcctgtatcatcaaaagccatgtatg
acgcttactggaacggtaaattcagagactgcgctttccattctggctttaatgaggatccattcgtttgtgaatatcaag
gccaatcgtctgacctgcctcaacctcctgtcaatgctggcggcggctctggtggtggttctggtggcggctctgagggt
ggcggctctgagggtggcggttctgagggtggcggctctgagggtggcggttccggtggcggctccggttccggtga
ttttgattatgaaaaaatggcaaacgctaataaggggggctatgaccgaaaatgccgatgaaaacgcgctacagtctga
cgctaaaggcaaacttgattctgtcgctactgattacggtgctgctatcgatggtttcattggtgacgtttccggccttgct
aatggtaatggtgctactggtgattttgctggctctaattcccaaatggctcaagtcggtgacggtgataattcacccttta
atgaataatttccgtcaatatttaccttctttgcctcagtcggttgaatgtcgcccttatgtctttggcgctggtaaaccata
tgaattttctattgattgtgacaaaataaacttattccgtggtgtctttgcgtttcttttatatgttgccaccttttatgtatgta
ttttcgacgtttgctaacatactgcgtaataaggagtcttaaggcctgataagcatgcgtaggagaaaataaaatgaaa
caaagcactattgcactggcactcttaccgttgctcttcaccccctgttaccaaagccgactacaaagatgaagtgcaatt
gaaagaaagcggcccggccctggtgaaaccgacccaaaccctgaccctgacctgtacctttcccggatttagcctgtcc
acgtctggcgttggcgtgggctggattcgccagccgcctgggaaagccctcgagtggctggctctgattgattgggat
gatgataagtattatagcaccagcctgaaaacgcgtctgaccattagcaaagatacttcgaaaaatcaggtggtgctg
actatgaccaacatggacccggtggatacggccacctattattgcgcgcgttttgatcctttttttttgattctttttttgattat
tggggccaaggcaccctggtgacggttagctcagcgggtggcggttctggcggcggtgggagcggtggcggtggttc
tggcggtggtggttccgatatcgtgctgacccagccgccttcagtgagtggcgcaccaggtcagcgtgtgaccatctcg
tgtagcggcagcagcagcaacattggcagcaactatgtgagctggtaccagcagttgccggggacggcgccgaaact
gctgatttatgataacaaccagcgtccctcaggcgtgccggatcgttttagcggatccaaaagcggcaccagcgcgag
ccttgcgattacgggcctgcaaagcgaagacgaagcggattattattgccagagctatgaccagaatgctcttgttgag
gtgtttggcggcggcacgaagttaaccgttcttggccaggaattcccagggggggagcggaggcgcgccgcaccatca
tcaccatcactgctgataagcttgacctgtgaagtgaaaaatggcgcagattgtgcgacattttttttttgtctgccgtttaa
tgaaattgtaaacgttaatattttgttaaaattcgcgttaaatttttgttaaatcagctcattttttaaccaataggccgaaa
tcggcaaaatcccttataaatcaaaagaatagaccgagatagggttgagtgttgttccagtttggaacaagagtccact
attaaagaacgtggactccaacgtcaaagggcgaaaaaccgtctatcagggcgatggcccactacgagaaccatcac
cctaatcaagttttttggggtcgaggtgccgtaaagcactaaatcggaaccctaaagggagccccccgatttagagcttg
acggggaaagccggcgaacgtggcgagaaaggaagggaagaaagcgaaaggagcgggcgctagggcgctggca
agtgtagcggtcacgctgcgcgtaaccaccacacccgccgcgcttaatgcgccgctacagggcgcgtgctagccatgt
gagcaaaaggccagcaaaaggccaggaaccgtaaaaaggccgcgttgctggcgtttttccataggctccgcccccct
gacgagcatcacaaaaatcgacgctcaagtcagaggtggcgaaacccgacaggactataaagataccaggcgtttcc
ccctggaagctccctcgtgcgctctcctgttccgaccctgccgcttaccggatacctgtccgcctttctcccttcgggaagc
gtggcgctttctcatagctcacgctgtaggtatctcagttcggtgtaggtcgttcgctccaagctgggctgtgtgcacga
accccccgttcagtccgaccgctgcgccttatccggtaactatcgtcttgagtccaacccggtaagacacgacttatcgc
cactggcagcagccactggtaacaggattagcagagcgaggtatgtaggcggtgctacagagttcttgaagtggtgg
cctaactacggctacactagaagaacagtatttggtatctgcgctctgctgtagccagttaccttcggaaaaagagttgg
tagctcttgatccggcaaacaaaccaccgctggtagcggtggtttttttgtttgcaagcagcagattacgcgcagaaaa
aaaggatctcaagaagatcctttgatcttttctacggggtctgacgctcagtggaacgaaaactcacgttaagggatttt
ggtcagatctagcaccaggcgtttaagggcaccaataactgccttaaaaaaattacgccccgccctgccactcatcgca
gtactgttgtaattcattaagcattctgccgacatggaagccatcacaaacggcatgatgaacctgaatcgccagcggc
atcagcaccttgtcgccttgcgtataatatttgcccatagtgaaaacggggcgaagaagttgtccatattggctacgtt
taaatcaaaactggtgaaactcacccagggattggctgagacgaaaaacatattctcaataaaccctttagggaaata
ggccaggttttcaccgtaacacgccacatcttgcgaatatatgtgtagaaactgccggaaatcgtcgtggtattcactcc
agagcgatgaaaacgtttcagtttgctcatggaaaacggtgtaacaagggtgaacactatcccatatcaccagctcacc
gtctttcattgccatacgaactccgggtgagcattcatcaggcgggcaagaatgtgaataaaggccggataaaactt
gtgcttatttttctttacggtctttaaaaaggccgtaatatccagctgaacggtctggttataggtacattgagcaactga
ctgaaatgcctcaaaatgttctttacgatgccattgggatatatcaacggtggtatatccagtgatttttttctccatttag
cttccttagctcctgaaaatctcgataactcaaaaaatacgcccggtagtgatcttatttcattatggtgaaagttggaac
ctcacccgacgtctaatgtgagttagctcactcattaggcaccccaggctttacactttatgcttccggctcgtatgttgtg
tggaattgtgagcggataacaatttcacacaggaaacagctatgaccatgattacgaattt
```

FIG. 5D

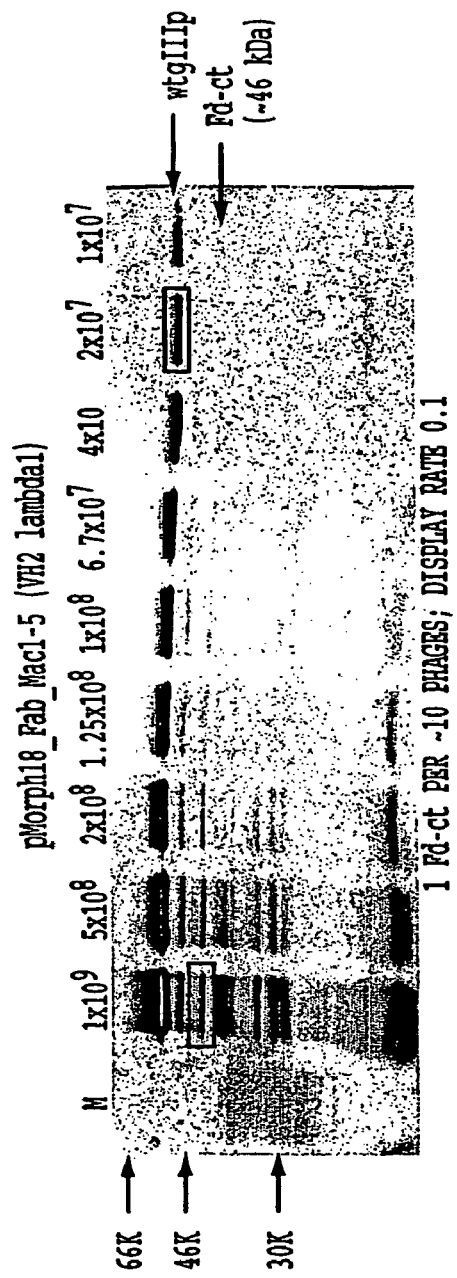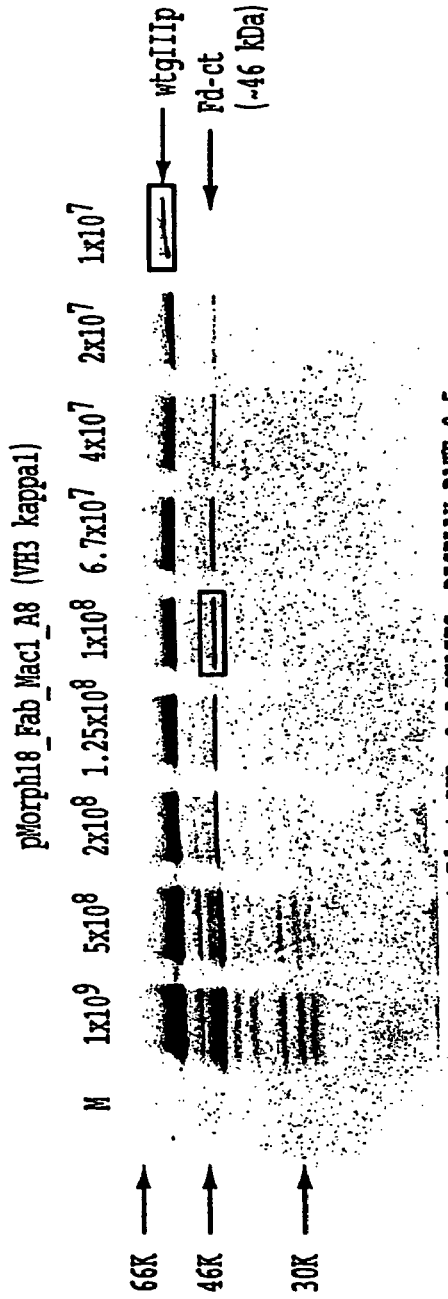

```
tctagataacgagggcaaaaaatgaaaaagacagctatcgcgattgcagtggcactggctggtttcgctaccgtagcg
caggccgatatcgtgctgacccagccgccttcagtgagtggcgcaccaggtcagcgtgtgaccatctcgtgtagcggc
agcagcagcaacattggcagcaactatgtgagctggtaccagcagttgcccgggacggcgccgaaactgctgatttat
gataacaaccagcgtccctcaggcgtgccggatcgttttagcggatccaaaagcggcaccagcgcgagccttgcgatt
acgggcctgcaaagcgaagacgaagcggattattattgccagagctatgaccagaatgctcttgttgaggtgtttggc
ggcggcacgaagttaaccgttcttggccagccgaaagccgcaccgagtgtgacgctgtttccgccgagcagcgaagaa
ttgcaggcgaacaaagcgaccctggtgtgcctgattagcgactttatccgggagccgtgacagtggcctggaaggca
gatagcagccccgtcaaggcgggagtggagaccaccacaccctccaaacaaagcaacaacaagtacgcggccagcagc
tatctgagcctgacgcctgagcagtggaagtcccacagaagctacagctgccaggtcacgcatgaggggagcacgtg
gaaaaaaccgttgcgccgactgaggcctgataagcatgcgtaggagaaaataaaatgaaacaaagcactattgcactg
gcactcttaccgttgctcttcacccctgttaccaaagcccaggtgcaattgaaagaaagcggcccggccctggtgaaa
ccgacccaaaccctgaccctgacctgtaccttttccggatttagcctgtccacgtctggcgttggcgtgggctggatt
cgccagccgcctgggaaagccctcgagtggctggctctgattgattgggatgatgataagtattatagcaccagcctg
aaaacgcgtctgaccattagcaaagatacttcgaaaaatcaggtggtgctgactatgaccaacatggaccggtggat
acggccacctattattgcgcgcgttttgatccttttttttgattctttttttgattattggggccaaggcaccctggtg
acggttagctcagcgtcgaccaaaggtccaagcgtgtttccgctggctccgagcagcaaaagcaccagcggcggcacg
gctgccctgggctgcctggttaaagattatttcccggaaccagtcaccgtgagctggaacagcggggcgctgaccagc
ggcgtgcataccttccggcggtgctgcaaagcagcggcctgtatagcctgagcagcgttgtgaccgtgccgagcagc
agcttaggcactcagacctatatttgcaacgtgaaccataaaccgagcaacaccaaagtggataaaaaagtggaaccg
aaaagcgaattcggggagggagcgggagcggtgattttgattatgaaaagatggcaaacgctaataaggggctatg
accgaaaatgccgatgaaaacgcgctacagtctgacgctaaaggcaaacttgattctgtcgctactgattacggtgct
gctatcgatggttcattggtgacgtttccggccttgctaatggtaatggtgctactggtgattttgctggctctaat
tcccaaatggctcaagtcggtgacggtgataattcacctttaatgaataatttccgtcaatatttaccttccctccct
caatcggttgaatgtcgcccttttgtctttggcgctggtaaaccatatgaattttctattgattgtgacaaaataaac
ttattccgtggtgtctttgcgtttcttttatatgttgccaccttatgtatgtattttctacgtttgctaacatactg
cgtaataaggagtcttgataagcttgacctgtgaagtgaaaaatggcgcagattgtgcgacattttttttgtctgccg
tttaatgaaattgtaaacgttaatattttgttaaaattcgcgttaaattttgttaaatcagctcatttttaaccaa
taggccgaaatcggcaaaatcccttataaatcaaaagaatagaccgagatagggttgagtgttgttccagtttggaac
aagagtccactattaaagaacgtggactccaacgtcaaagggcgaaaaaccgtctatcagggcgatggcccactacga
gaaccatcaccctaatcaagttttttggggtcgaggtgccgtaaagcactaaatcggaacccctaaagggagcccccga
tttagagcttgacggggaaagccggcgaacgtggcgagaaaggaagggaagaaagcgaaaggagcgggcgctagggcg
ctggcaagtgtagcggtcacgctgcgcgtaaccaccacacccgccgcgcttaatgcgccgctacagggcgcgtgctag
ccatgtgagcaaaaggccagcaaaaggccaggaaccgtaaaaaggccgcgttgctggcgtttttccataggctccgcc
cccctgacgagcatcacaaaaatcgacgctcaagtcagaggtggcgaaacccgacaggactataaagataccaggcgt
ttccccctggaagctccctcgtgcgctctcctgttccgaccctgccgcttaccggatacctgtccgcctttctccctt
cgggaagcgtggcgctttctcatagctcacgctgtaggtatctcagttcggtgtaggtcgttcgctccaagctgggct
gtgtgcacgaaccccccgttcagtccgaccgctgcgccttatccggtaactatcgtcttgagtccaacccggtaagac
acgacttatcgccactggcagcagccactggtaacaggattagcagagcgaggtatgtaggcggtgctacagagttct
tgaagtggtggcctaactacggctacactagaagaacagtatttggtatctgcgctctgctgtagccagttaccttcg
gaaaaagagttggtagctcttgatccggcaaacaaaccaccgctggtagcggtggtttttttgtttgcaagcagcaga
ttacgcgcagaaaaaaaggatctcaagaagatcctttgatcttttctacggggtctgacgctcagtggaacgaaaact
cacgttaagggattttggtcagatctagcaccaggcgtttaagggcaccaataactgccttaaaaaattacgccccg
ccctgccactcatcgcagtactgttgtaattcattaagcattctgccgacatggaagccatcacaaacggcatgatga
acctgaatcgccagcggcatcagcaccttgtcgccttgcgtataatatttgcccatagtgaaaacggggcgaagaag
ttgtccatattggctacgtttaaatcaaaactggtgaaactcacccaggggattggctgagacgaaaaacatattctca
ataaacccttaggggaaataggccaggttttcaccgtaacacgccacatcttgcgaatatatgtgtagaaactgccgg
aaatcgtcgtggtattcactccagagcgatgaaaacgtttcagtttgctcatggaaaacggtgtaacaagggtgaaca
ctatcccatatcaccagctcaccgtctttcattgccatacggaactccgggtgagcattcatcaggcgggcaagaatg
tgaataaaggccggataaaacttgtgcttatttttctttacggtctttaaaaaggccgtaatatccagctgaacggtc
tggttataggtacattgagcaactgactgaaatgcctcaaaatgttctttacgatgccattgggatatatcaacggtg
gtatatccagtgattttttctccatttttagcttccttagctcctgaaaatctcgataactcaaaaaatacgcccggt
agtgatcttatttcattatggtgaaagttggaacctcacccgacgtctaatgtgagttagctcactcattaggcaccc
caggctttacactttatgcttccggctcgtatgttgtgtggaattgtgagcggataacaatttcacacaggaaacagc
tatgaccatgattacgaatt
```

FIG. 6D

```
cagcagttgcccgggacggcgccgaaactgctgatttatgataacaaccagcgtccctcaggcgtgccggatcgttttagcggatc
caaaagcggcaccagcgcgagccttgcgattacgggcctgcaaagcgaagacgaagcggattattattgccagagctatgacca
gaatgctcttgttgaggtgtttggcggcggcacgaagttaaccgttcttggccagccgaaagccgcaccgagtgtgacgctgtttcc
gccgagcagcgaagaattgcaggcgaacaaagcgaccctggtgtgcctgattagcgacttttatccgggagccgtgacagtggcc
tggaaggcagatagcagccccgtcaaggcgggagtggagaccaccacaccctccaaacaaagcaacaacaagtacgcggccag
cagctatctgagcctgacgcctgagcagtggaagtcccacagaagctacagctgccaggtcacgcatgaggggagcaccgtgga
aaaaaccgttgcgccgactgaggcctctccagggggagcggaggcgcgccgcaccatcatcaccatcactgctgataatatgca
tgcgtaggagaaaataaaatgaaacaaagcactattgcactggcactcttaccgttgctcttcaccctgttaccaaagccaggtg
caattgaaagaaagcggcccggccctggtgaaaccgacccaaaccctgaccctgacctgtacctttccggatttagcctgtccacg
tctggcgttggcgtgggctggattcgccagccgcctgggaaagccctcgagtggctggctctgattgattgggatgatgataagtat
tatagcaccagcctgaaaacgcgtctgaccattagcaaagatacttcgaaaaatcaggtggtgctgactatgaccaacatggaccc
ggtggatacggccacctattattgcgcgcgttttgatcctttttttgattctttttttgattattgggccaaggcaccctggtgacggtt
agctcagcgtcgaccaaaggtccaagcgtgtttccgctggctccgagcagcaaaagcaccagcggcggcacggctgccctgggct
gcctggttaaagattatttcccggaaccagtcaccgtgagctggaacagcggggcgctgaccagcggcgtgcatacctttccggcg
gtgctgcaaagcagcggcctgtatagcctgagcagcgttgtgaccgtgccgagcagcagcttaggcactcagacctatatttgcaa
cgtgaaccataaaccgagcaacaccaaagtggataaaaaagtggaaccgaaaagcgaattcgactataaagatgacgatgacaa
aggcgcgccgtggagccaccgcagtttgaaaaatgataagcttgacctgtgaagtgaaaaatggcgcagattgtgcgacatttttt
tttgtctgccgtttaattaaaggggggggggggccggcctgggggggggtgtacatgaaattgtaaacgttaatattttgttaaat
tcgcgttaaattttttgttaaatcagctcattttttaaccaataggccgaaatcggcaaaatcccttataaatcaaaagaatagaccga
gataggggttgagtgttgttccagtttggaacaagagtccactattaaagaacgtggactccaacgtcaaagggcgaaaaaccgtct
atcagggcgatggcccactacgagaaccatcaccctaatcaagttttttggggtcgaggtgccgtaaagcactaaatcggaaccct
aaagggagccccccgatttagagcttgacggggaaagccggcgaacgtggcgagaaaggaagggaagaaagcgaaaggagcg
ggcgctagggcgctggcaagtgtagcggtcacgctgcgcgtaaccaccacacccgccgcgcttaatgcgccgctacagggcgcgt
gctagactagtgtttaaaccggaccgggggggggcttaagtgggctgcaaaacaaaacggcctcctgtcaggaagccgcttttatc
gggtagcctcactgcccgctttccagtcgggaaacctgtcgtgccagctgcatcagtgaatcggccaacgcgcggggagaggcgg
tttgcgtattgggagccagggtggttttttcttttcaccagtgagacgggcaacagctgattgcccttcaccgcctggccctgagagag
ttgcagcaagcggtccacgctggtttgccccagcaggcgaaaatcctgtttgatggtggtcagcggcgggatataacatgagctgt
cctcggtatcgtcgtatcccactaccgagatgtccgcaccaacgcgcagcccggactcggtaatggcacgcattgcgcccagcgcc
atctgatcgttggcaaccagcatcgcagtgggaacgatgccctcattcagcatttgcatggtttgttgaaaaccggacatggcactcc
agtcgccttcccgttccgctatcggctgaatttgattgcgagtgagatatattgccagccagccagacgcagacgcgccgagacag
aacttaatgggccagctaacagcgcgatttgctggtggcccaatgcgaccagatgctccacgcccagtcgcgtaccgtcctcatgg
gagaaaataatactgttgatgggtgtctggtcagagacatcaagaaataacgccggaacattagtgcaggcagcttccacagcaa
tagcatcctggtcatccagcggatagttaataatcagcccactgacacgttgcgcgagaagattgtgcaccgccgctttacaggcttc
gacgccgcttcgttctaccatcgacacgaccacgctggcacccagttgatcggcgcgagatttaatcgccgcgacaatttgcgacgg
cgcgtgcagggccagactggaggtggcaacgccaatcagcaacgactgtttgcccgccagttgttgtgccacgcggttaggaatgt
aattcagctccgccatcgccgcttccactttttcccgcgttttcgcagaaacgtggctggcctggttcaccacgcgggaaacggtctg
ataagagacaccggcatactctgcgacatcgtataacgttactggtttcacattcaccaccctgaattgactctcttccgggcgctatc
atgccataccgcgaaaggttttgcgccattcgatgctagccatgtgagcaaaaggccagcaaaaggccaggaaccgtaaaaagg
ccgcgttgctggcgtttttccataggctccgcccccctgacgagcatcacaaaaatcgacgctcaagtcagaggtggcgaaacccg
acaggactataaagataccaggcgtttccccctggaagctccctcgtgcgctctcctgttccgaccctgccgcttaccggatacctgtc
cgcctttctcccttcgggaagcgtggcgctttctcatagctcacgctgtaggtatctcagttcggtgtaggtcgttcgctccaagctgg
gctgtgtgcacgaaccccccgttcagcccgaccgctgcgccttatccggtaactatcgtcttgagtccaacccggtaagacacgactt
atcgccactggcagcagccactggtaacaggattagcagagcgaggtatgtaggcggtgctacagagttcttgaagtggtggcct
aactacggctacactagaagaacagtatttggtatctgcgctctgctgtagccagttaccttcggaaaagagttggtagctcttgat
ccggcaaacaaaccaccgctggtagcggtggttttttgtttgcaagcagcagattacgcgcagaaaaaaaggatctcaagaagat
cctttgatcttttctacggggtctgacgctcagtggaacgaaaactcacgttaagggattttggtcagatctagcaccaggcgtttaa
gggcaccaataactgccttaaaaaaattacgccccgccctgccactcatcgcagtactgttgtaattcattaagcattctgccgacat
ggaagccatcacaaacggcatgatgaacctgaatcgccagcggcatcagcaccttgtcgccttgcgtataatatttgcccatagtga
aaacgggggcgaagaagttgtccatattggctacgtttaaatcaaaactggtgaaactcacccagggattggctgagacgaaaaa
catattctcaataaaccctttagggaaataggccaggttttcaccgtaacacgccacatcttgcgaatatatgtgtagaaactgccgg
aaatcgtcgtggtattcactccagagcgatgaaaacgtttcagtttgctcatggaaaacggtgtaacaagggtgaacactatccat
atcaccagctcaccgtctttcattgccatacggaactccgggtgagcattcatcaggcgggcaagaatgtgaataaaggccggata
aaacttgtgcttatttttctttacggtctttaaaaaggccgtaatatccagctgaacggtctggttataggtacattgagcaactgactg
aaatgcctcaaaatgttctttacgatgccattgggatatatcaacggtggtatatccagtgatttttttctccatttttagcttccttagctc
ctgaaaatctcgataactcaaaaaatacgcccggtagtgatcttatttcattatggtgaaagttggaacctcacccgacgtctaatgt
gagttagctcactcattaggcaccccaggctttacactttatgcttccggctcgtatgttgtgtggaattgtgagcggataacaatttc
acacaggaaacagctatgaccatgattacgaatttctagataacgagggcaaaaaatgaaaagacagctatcgcgattgcagtg
gcactggctggtttcgctaccgtagcgcaggccgatatcgtgctgacccagccgcctcagtgagtggcgcaccaggtcagcgtgt
gaccatctcgtgtagcggcagcagcagcaacattggcagcaactatgtgagctggtac
```

FIG. 7D

```
gcgacatcgtataacgttactggtttcacattcaccaccctgaattgactctcttccgggcgctatcatgccataccgcgaaaggtttt
gcgccattcgatgctagccatgtgagcaaaaggccagcaaaaggccaggaaccgtaaaaaggccgcgttgctggcgtttttccat
aggctccgcccccctgacgagcatcacaaaaatcgacgctcaagtcagaggtggcgaaacccgacaggactataaagataccag
gcgtttccccctggaagctccctcgtgcgctctcctgttccgaccctgccgcttaccggatacctgtccgcctttctcccttcgggaagc
gtggcgctttctcatagctcacgctgtaggtatctcagttcggtgtaggtcgttcgctccaagctgggctgtgtgcacgaaccccccgt
tcagcccgaccgctgcgccttatccggtaactatcgtcttgagtccaacccggtaagacacgacttatcgccactggcagcagccact
ggtaacaggattagcagagcgaggtatgtaggcggtgctacagagttcttgaagtggtggcctaactacggctacactagaagaa
cagtatttggtatctgcgctctgctgtagccagttaccttcggaaaaagagttggtagctcttgatccggcaaacaaaccaccgctgg
tagcggtggtttttttgtttgcaagcagcagattacgcgcagaaaaaaaggatctcaagaagatcctttgatcttttctacggggtct
gacgctcagtggaacgaaaactcacgttaagggattttggtcagatctagcaccaggcgtttaagggcaccaataactgccttaaa
aaaattacgccccgccctgccactcatcgcagtactgttgtaattcattaagcattctgccgacatggaagccatcacaaacggcatg
atgaacctgaatcgccagcggcatcagcaccttgtcgccttgcgtataatatttgcccatagtgaaaacggggggcgaagaagttgtc
catattggctacgtttaaatcaaaactggtgaaactcacccaggggattggctgagacgaaaaacatattctcaataaacccttagg
gaaataggccaggttttcaccgtaacacgccacatcttgcgaatatatgtgtagaaactgccggaaatcgtcgtggtattcactcca
gagcgatgaaaacgtttcagtttgctcatggaaaacggtgtaacaagggtgaacactatcccatatcaccagctcaccgtctttcatt
gccatacggaactccgggtgagcattcatcaggcgggcaagaatgtgaataaaggccggataaaacttgtgcttatttttctttacg
gtctttaaaaaggccgtaatatccagctgaacggtctggttataggtacattgagcaactgactgaaatgcctcaaaatgttctttac
gatgccattgggatatatcaacggtggtatatccagtgatttttttctccatttagcttccttagctcctgaaaatctcgataactcaaa
aaatacgcccggtagtgatcttatttcattatggtgaaagttggaacctcacccgacgtctaatgtgagttagctcactcattaggcac
cccaggctttacactttatgcttccggctcgtatgttgtgtggaattgtgagcggataacaattcacacaggaaacagctatgacca
tgattacgaatttctagataacgagggcaaaaaatgaaaaagacagctatcgcgattgcagtggcactggctggtttcgctaccgt
agcgcaggccgatatcgtgctgacccagccgccttcagtgagtggcgcaccaggtcagcgtgtgaccatctcgtgtagcggcagca
gcagcaacattggcagcaactatgtgagctggtaccagcagttgcccgggacggcgccgaaactgctgatttatgataacaacca
gcgtccctcaggcgtgccggatcgttttagcggatccaaaagcggcaccagcgcgagccttgcgattacgggcctgcaaagcgaa
gacgaagcggattattattgccagagctatgaccagaatgctcttgttgaggtgtttggcggcggcacgaagttaaccgttcttggc
cagccgaaagccgcaccgagtgtgacgctgtttccgccgagcagcgaagaattgcaggcgaacaaagcgaccctggtgtgcctg
attagcgactttatccgggagccgtgacagtggcctggaaggcagatagcagcccgtcaaggcgggagtggagaccaccaca
ccctccaaacaaagcaacaacaagtacgcggccagcagctatctgagcctgacgcctgagcagtggaagtcccacagaagctaca
gctgccaggtcacgcatgaggggagcaccgtggaaaaaaccgttgcgccgactgaggcctgataagcatgcgtaggagaaaata
aaatgaaacaaagcactattgcactggcactcttaccgttgctcttcaccccctgttaccaaagcccaggtgcaattgaaagaaagcg
gccccggccctggtgaaaccgacccaaaccctgaccctgacctgtaccttttccggatttagcctgtccacgtctggcgttggcgtggg
ctggattcgccagccgcctgggaaagccctcgagtggctggctctgattgattgggatgatgataagtattatagcaccagcctgaa
aacgcgtctgaccattagcaaagatacttcgaaaaatcaggtggtgctgactatgaccaacatggaccggtggatacggccacct
attattgcgcgcgttttgatccttttttttgattctttttttgattattgggccaaggcaccctggtgacggttagctcagcgtcgaccaa
aggtccaagcgtgtttccgctggctccgagcagcaaaagcaccagcggcggcacggctgccctgggctgcctggttaaagattatt
tcccggaaccagtcaccgtgagctggaacagcggggcgctgaccagcggcgtgcataccttccggcggtgctgcaaagcagcgg
cctgtatagcctgagcagcgttgtgaccgtgccgagcagcagcttaggcactcagacctatatttgcaacgtgaaccataaaccga
gcaacaccaaagtggataaaaaagtggaaccgaaaagcgaattcccaggggggagcggaggcgccccgcaccatcatcaccat
cactgctgataagcttgacctgtgaagtgaaaaatggcgcagattgtgcgacattttttttgtctgccgtttaattaaagggggggg
gggccggcctgcggggggtgtacatgaaattgtaaacgttaatattttgttaaaattcgcgttaaattttttgttaaatcagctcattt
tttaaccaataggccgaaatcggcaaaatcccttataaatcaaaagaatagaccgagatagggttgagtgttgttccagtttggaac
aagagtccactattaaagaacgtggactccaacgtcaaagggcgaaaaaccgtctatcagggcgatggcccactacgagaaccat
cacccctaatcaagttttttggggtcgaggtgccgtaaagcactaaatcggaaccctaaagggagccccccgatttagagcttgacgg
ggaaagccggcgaacgtggcgagaaaggaagggaagaaagcgaaaggagcgggcgctagggcgctggcaagtgtagcggtc
acgctgcgcgtaaccaccacacccgccgcgcttaatgcgccgctacagggcgcgtgctagactagtgtttaaaccggaccggggg
ggggcttaagtgggctgcaaaacaaaacggcctcctgtcaggaagccgcttttatcgggtagcctcactgcccgctttccagtcggg
aaacctgtcgtgccagctgcatcagtgaatcggccaacgcgcggggagaggcggtttgcgtattgggagccagggtggtttttcttt
tcaccagtgagacgggcaacagctgattgcccttcaccgcctggccctgagagagttgcagcaagcggtccacgctggtttgcccc
agcaggcgaaaatcctgtttgatggtggtcagcggcgggatataacatgagctgtcctcggtatcgtcgtatcccactaccgagatg
tccgcaccaacgcgcagcccggactcggtaatggcacgcattgcgcccagccatctgatcgttggcaaccagcatcgcagtggg
aacgatgccctcattcagcatttgcatggtttgttgaaaaccggacatggcactccagtcgccttcccgttccgctatcggctgaattt
gattgcgagtgagatatttatgccagccagccagacgcagacgcgccgagacagaacttaatgggccagctaacagcgcgatttg
ctggtggcccaatgcgaccagatgctccacgcccagtcgcgtaccgtcctcatgggagaaaataatactgttgatgggtgtctggtc
agagacatcaagaaataacgccggaacattagtgcaggcagcttccacagcaatagcatcctggtcatccagcggatagttaata
atcagcccactgacacgttgcgcgagaagattgtgcaccgccgctttacaggcttcgacgccgcttcgttctaccatcgacacgacc
acgctggcaccagttgatcggcgcgagatttaatcgccgcgacaatttgcgacggcgcgtgcagggccagactggaggtggcaa
cgccaatcagcaacgactgtttgcccgccagttgttgtgccacgcggttaggaatgtaattcagctccgccatcgccgcttccactttt
tcccgcgttttcgcagaaacgtggctggcctggttcaccacgcggggaaacggtctgataagagacaccggcatactct
```

FIG. 7F caagctgtgaccgtctccgggagctgcatgtgtcagaggttttcaccgtcatcaccgaaacgcgcgaggcagctgcggtaaagctc
atcagcgtggtcgtgaagcgattcacagatgtctgcctgttcatccgcgtccagctcgttgagtttctccagaagcgttaatgtctggc
ttctgataaagcgggccatgttaagggcggttttttcctgtttggtcactgatgcctccgtgtaaggggggatttctgttcatgggggta
atgataccgatgaaacgagagaggatgctcacgatacgggttactgatgatgaacatgccggttactggaacgttgtgagggta
aacaactggcggtatggatgcggcgggaccagagaaaaatcactcagggcaatgccagcgcttcgttaatacagatgtaggtgt
tccacagggtagccagcagcatcctgcgatgcagatccggaacataatggtgcagggcgctgacttccgcgtttccagactttacg
aaacacggaaaccgaagaccattcatgttgttgctcaggtcgcagacgttttgcagcagcagtcgcttcacgttcgctcgcgtatcg
gtgattcattctgctaaccagtaaggcaaccccgccagcctagccgggtcctcaacgacaggagcacgatcatgcgcaccgtggc
caggacccaacgctgcccgagatgcgccgcgtgcggctgctggagatggcggacgcgatggatatgttctgccaagggttggttt
gcgcattcacagttctccgcaagaattgattggctccaattcttggagtggtgaatccgttagcgaggtgccgccggcttccattcag
gtcgaggtggcccggctccatgcaccgcgacgcaacgcggggaggcagacaaggtatagggcggcgcctacaatccatgccaac
ccgttccatgtgctcgccgaggcggcataaatcgccgtgacgatcagcggtccagtgatcgaagttaggctggtaagagccgcga
gcgatccttgaagctgtccctgatggtcgtcatctacctgcctggacagcatggcctgcaacgcgggcatcccgatgccgccggaa
gcgagaagaatcataatggggaaggccatccagcctcgcgtcgcgaacgccagcaagacgtagcccagcgcgtcggccgccatg
ccggcgataatggcctgcttctcgccgaaacgtttggtggcgggaccagtgacgaaggcttgagcgagggcgtgcaagattccga
ataccgcaagcgacaggccgatcatcgtcgcgctccagcgaaagcggtcctcgccgaaaatgacccagagcgctgccggcacctg
tcctacgagttgcatgataaagaagacagtcataagtgcgcgacgatagtcatgccccgcgcccaccggaaggagctgactggg
ttgaaggctctcaagggcatcggtcgacgctctcccttatgcgactcctgcattaggaagcagcccagtagtaggttgaggccgttg
agcaccgccgccgcaaggaatggtgcatgcaaggagatggcgcccaacagtcccccggccacggggcctgccaccatacccacg
ccgaaacaagcgctcatgagcccgaagtggcgagcccgatcttccccatcggtgatgtcggcgatataggcgccagcaaccgcac
ctgtggcgccggtgatgccggccacgatgcgtccggcgtagaggatccacaggacgggtgtggtcgccatgatcgcgtagtcgat
agtggctccaagtagcgaagcgagcaggactgggcggcggccaaagcggtcggacagtgctccgagaacgggtgcgcatagaa
attgcatcaacgcatatagcgctagcctgaggccagtttgctcaggctctccccgtggaggtaataattgctcgaccgataaaagcg
gcttcctgacaggaggccgttttgttttgcagcccacctcaacgcaattaatgtgagttagctcactcattaggcacccaggctttac
actttatgcttccggctcgtatgttgtgtggaattgtgagcggataacaatttcacacaggaaacagctatgaccatgattacgaattt
ctagataacgagggcaaaaaatgaaaaagacagctatcgcgattgcagtggcactggctggtttcgctaccgtagcgcaggccga
ctactgcgatatcgaattcgcagaaacagttgaaagttgtttagcaaaaccccatacagaaaattcatttactaacgtctggaaaga
cgacaaaactttagatcgttacgctaactatgagggctgtctgtgaatgctacaggcgttgtagtttgtactggtgacgaaactcag
tgttacggtacatgggttcctattgggcttgctatccctgaaaatgagggtggtggctctgagggtggcggttctgagggtggcggc
tctgagggtggcggtactaaaccctcctgagtacggtgatacacctattccgggctatacttatatcaaccctctcgacggcacttatcc
gcctggtactgagcaaaacccgctaatcctaatccttctcttgaggagtctcagcctcttaatactttcatgtttcagaataataggtt
ccgaaataggcaggggcattaactgtttatacgggcactgttactcaaggcactgaccccgttaaaacttattaccagtacactcct
gtatcatcaaaagccatgtatgacgcttactggaacggtaaattcagagactgcgctttccattctggctttaatgaggatccattcgt
ttgtgaatatcaaggccaatcgtctgacctgcctcaacctcctgtcaatgctggcggcggctctggtggtggttctggtggcggctct
gagggtggcggctctgagggtggcggttctgagggtggcggctctgagggtggcggttccggtggcggctccggttccggtgatt
ttgattatgaaaaaatggcaaacgctaataagggggctatgaccgaaaatgccgatgaaaacgcgctacagtctgacgctaaagg
caaacttgattctgtcgctactgattacggtgctgctatcgatggtttcattggtgacgtttccggccttgctaatggtaatggtgctac
tggtgattttgctggctctaattcccaaatggctcaagtcggtgacggtgataattcacctttaatgaataatttccgtcaatatttacct
tctttgcctcagtcggttgaatgtcgcccttatgtctttggcgctggtaaaccatatgaattttctattgattgtgacaaaataaacttat
tccgtggtgtctttgcgtttcttttatatgttgccacctttatgtatgtattttcgacgtttgctaacatactgcgtaataaggagtcttaa
gcttatcgatgataagctgtcaaacatgagaattcttgaagacgaaagggcctcgtgatacgcctatttttataggttaatgtcatga
taataatggtttcttagacgtcaggtggcacttttcggggaaatgtgcgcggaacccctatttgtttatttttctaaatacattcaaata
tgtatccgctcatgagacaataaccctgataaatgcttcaataatattgaaaaaggaagagtatgagtattcaacatttccgtgtcgc
ccttattcccttttttgcggcattttgccttcctgtttttgctcacccagaaacgctggtgaaagtaaaagatgctgaagatcagttggg
tgcacgagtgggttacatcgaactggatctcaacagcggtaagatccttgagagttttcgccccgaagaacgttttccaatgatgag
cacttttaaagttctgctatgtggcgcggtattatcccgtgttgacgccgggcaagagcaactcggtcgccgcatacactattctcag
aatgacttggttgagtactcaccagtcacagaaaagcatcttacggatggcatgacagtaagagaattatgcagtgctgccataac
catgagtgataacactgcggccaacttacttctgacaacgatcggaggaccgaaggagctaaccgcttttttgcacaacatggggg
atcatgtaactcgccttgatcgttgggaaccggagctgaatgaagccataccaaacgacgagcgtgacaccacgatgcctgcagc
aatggcaacaacgttgcgcaaactattaactggcgaactacttactctagcttcccggcaacaattaatagactggatggaggcgg
ataaagttgcaggaccacttctgcgctcggcccttccggctggctggtttattgctgataaatctggagccggtgagcgtgggtctcg
cggtatcattgcagcactggggccagatggtaagccctcccgtatcgtagttatctacacgacggggagtcaggcaactatggatg
aacgaaatagacagatcgctgagataggtgcctcactgattaagcattggtaactgtcagaccaagtttactcatatatactttagat
tgatttaaaacttcatttttaatttaaaaggatctaggtgaagatcctttttgataatctcatgaccaaaatcccttaacgtgagttttcg
ttccactgagcgtcagaccccgtagaaaagatcaaaggatcttcttgagatcctttttttctgcgcgtaatctgctgcttgcaaacaaa
aaaaccaccgctaccagcggtggtttgtttgccggatcaagagctaccaactctttttccgaaggtaactggcttcagcagagcgca
gataccaaatactgtccttctagtgtagccgtagttaggccaccacttcaagaactctgtagcaccgcctacatacctcgctctgctaa

```
tcctgttaccagtggctgctgccagtggcgataagtcgtgtcttaccgggttggactcaagacgatagttaccggataaggcgcagc
ggtcgggctgaacgggggggttcgtgcacacagcccagcttggagcgaacgacctacaccgaactgagatacctacagcgtgagct
atgagaaagcgccacgcttcccgaagggagaaaggcggacaggtatccggtaagcggcagggtcggaacaggagagcgcacg
agggagcttccagggggaaacgcctggtatctttatagtcctgtcgggtttcgccacctctgacttgagcgtcgattttgtgatgctc
gtcaggggggcggagcctatggaaaaacgccagcaacgcggccttttttacggttcctggccttttgctggccttttgctcacatgttc
tttcctgcgttatcccctgattctgtggataaccgtattaccgcctttgagtgagctgataccgctcgccgcagccgaacgaccgagc
gcagcgagtcagtgagcgaggaagcggaagagcgcctgatgcggtattttctccttacgcatctgtgcggtatttcacaccgcatat
ggtgcactctcagtacaatctgctctgatgccgcatagttaagccagtatacactccgctatcgctacgtgactgggtcatggctgcg
ccccgacacccgccaacacccgctgacgcgccctgacgggcttgtctgctcccggcatccgcttacaga
```

FIG. 7H-2

1 Fd-SS-gIII PER ~3 PHAGE; DISPLAY RATE 0.3

1 Fd-SS-gIII PER ~10 PHAGE; DISPLAY RATE 0.1

TRICISTRONIC VECTORS AND USES THEREFOR

This application claims priority to U.S. provisional application Ser. No. 60/399,150 filed Jul. 30, 2002. The entirety of this application is hereby expressly incorporated by reference.

BACKGROUND OF THE INVENTION

1. Field of the Invention

The field of the invention relates generally to the expression of recombinant DNA. More particularly, the invention relates to novel vectors (and uses therefor) that can be used to express at least three exogenous genes under the control of a single promoter.

2. Background

A persistent problem associated with expression of multiple, individual recombinant polypeptides (i.e. polypeptides that are not fused to each other) via a vector in an expression system is obtaining satisfactory yields of each polypeptide. This is especially true, for example, when the goal is to express multiple proteins that associate with each other upon expression, where poor yield of one or more of the components will hamper or prevent association of the expressed proteins.

The cloning, transformation and expression efficiencies of a vector typically are inversely related to its size, and therefore one common strategy for expressing multiple polypeptides in an expression system is to use multiple vectors instead of "overloading" a single vector. This approach has drawbacks, however. For instance, short of employing a selection protocol for each vector, there is no way to determine with certainty that a cell contains each vector. In addition, vector incompatibility can hinder obtaining suitable expression levels even where there is satisfactory vector uptake by the cells.

A separate approach is to integrate each exogenous gene into a single construct, but under the control of multiple promoters within that construct. This strategy, too, is riddled with disadvantages. For example, obtaining suitable expression requires successful function of multiple promoters, which can be difficult to achieve. Accordingly, there is no way to determine with certainty that a cell contains sufficient levels of each recombinant polypeptide, short of employing a selection protocol for each gene expression product operatively linked to its respective promoter. Furthermore, utilizing one promoter per exogenous gene disadvantageously results in a relatively large vector. Placing all cistrons into a single vector under the control of a single promoter has not been a viable option in nearly all applications, since, e.g., the further a cistron is positioned from its promoter, the less likely is the chance that acceptable expression yields will be obtained for that cistron.

Certain tricistronic vectors are known in the art, however. For example, Burger et al., *Appl. Microbiol. Biotechnol.* (1999) 52: 345-353 reported a tricistronic vector that encoded, in a 5-prime to 3-prime orientation, (i) a murine light chain Ig, (ii) a murine heavy chain Ig-TNFα fusion and (iii) puromycin acetyltransferase (pac) as a selective marker; Burger et al. stated that the foregoing tricistronic vector was selected because "expression of the selective marker and product are strictly linked" (id. at 351rt. col.).

However, in Burger et al., the non-Ig polypeptide (i.e., pac) functioned only as a selection vehicle and, hence, did not otherwise associate or otherwise interact with either the murine light chain Ig or heavy chain. Ig-TNFα fusion. Accordingly, Burger et al. provides no suggestion that three "structural" polypeptide domains could be expressed in sufficient yields so as to associate or otherwise interact with each other after expression. In other words, the disclosure by Burger et al. did not overcome the prejudice in the art against using a tricistronic vector to express three or more polypeptide domains that associate or otherwise interact with each other subsequent to expression. It is apparent, therefore, that a vector that satisfies these and other drawbacks known in the art is greatly to be desired. The present invention provides such vectors, together with methods for their use.

SUMMARY OF THE INVENTION

Accordingly, it is an object of the invention to provide enhanced expression vehicles for generating at least three polypeptide molecules that can interact with each other subsequent to expression.

It is a further object of the invention to provide enhanced expression vehicles that are compatible with a variety of prokaryotic hosts.

It is still a further object of the invention to provide methods of using the foregoing expression vehicles to discover new and improved therapeutics for treating disease.

These and other objects are made possible with reference to the teachings contained herein.

In one aspect, the invention provides a tricistronic vector construct that comprises a prokaryotic promoter, a first nucleic acid-sequence encoding an immunoglobulin-presenting polypeptide, a second nucleic acid sequence encoding a first immunoglobulin (Ig) polypeptide, a third nucleic acid sequence encoding a second Ig polypeptide; a first associating agent fused to or comprised within said Ig-presenting polypeptide and a second associating agent fused to or comprised within said first Ig polypeptide. The first, second and third nucleic acid sequences are under the control of said promoter and, upon expression of the tricistronic vector, the Ig-presenting polypeptide and the first Ig polypeptide associate via their respective associating agents and the first and second Ig polypeptides self-associate. The vector may optionally be a phagemid vector.

In one embodiment, the Ig-presenting polypeptide may be a phage coat protein, for example, a gIII protein or a functional fragment of a gIII protein. The gIII functional fragment may contain an N-terminal domain of gIII.

In another embodiment, the first and second Ig polypeptides self-associate to form a Fab or other functional Ig fragment, for example via a disulfide bond. The first and/or second associating agent may be a cysteine residue.

In still another embodiment, the first and second Ig polypeptides self-associate via non-covalent interactions.

In other embodiments, the vector contains (i) a first secretory signal sequence in the same reading frame as the nucleic acid sequence encoding the first Ig polypeptide, and/or a second secretory signal sequence in the same reading frame as the nucleic acid sequence encoding the second Ig polypeptide, and/or a third secretory signal sequence in the same reading frame as the nucleic acid sequence encoding the Ig-presenting polypeptide. The first, second and third secretory signal sequences may be prokaryotic signal sequences. The vector may further contain a ribosome binding site positioned 5-primeward of any or all of the nucleic acid sequences encoding the second Ig polypeptide, the first Ig polypeptide and/or the Ig-presenting polypeptide.

In still further embodiments, the associating agents become disassociated in solution upon the addition of a reducing agent. Alternatively, the second associating agent is fused to said first Ig polypeptide via a peptide linker.

The following text provides a more detailed, but non-limiting description of the present invention.

BRIEF DESCRIPTION OF THE FIGURES

FIG. 2B provides the nucleic acid sequence for the vector described in FIG. 2a (SEQ. ID NO:3).

FIG. 4D is the nucleic acid sequence for pMorph13 scFv Mac1-5 (SEQ. ID NO:4)

FIG. 5D is the nucleic acid sequence for pMorph20 Mac1-5 (SEQ. ID NO:5)

FIG. 6A is a gel that represents the display rate of a dicistronic Fab vector (pMORPH18) encoding a Fab of framework combination VH2 λ-1; (conventional display).

FIG. 6B is a gel that represents the display rate of a dicistronic Fab vector (pMORPH18) encoding a Fab of framework combination VH3 κ-1; (conventional display).

FIG. 6D is the nucleic acid sequence for pMORPH®18-Fab Mac1-5 (SEQ. ID NO:6)

FIG. 7D is the nucleic acid sequence for pMORPHX10 Fab Mac1-5 VL LHC VH FS (SEQ. ID NO:7)

FIG. 7F is the nucleic acid sequence for pMORPHX10 Fab Mac1-5 VL VH LHC (SEQ. ID NO:8)

FIG. 7H is the nucleic acid sequence for pBR-C-gIII (SEQ. ID NO:9)

DETAILED DESCRIPTION

Figure 1:
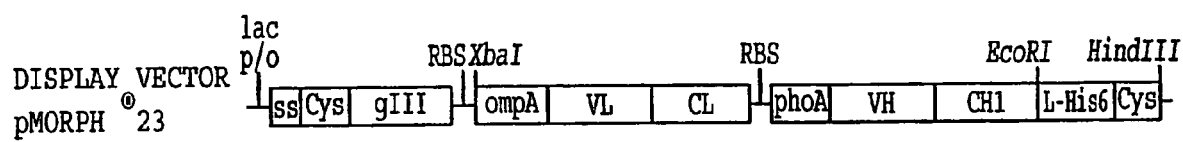
FIG. 1 is a schematic depiction of principal components of an inventive tricistronic vector, i.e., a single promoter, an Ig-presenting polypeptide, and two Ig polypeptides. Abbreviations: Lac p/o lac promoter operator region; SS gpIII signal sequence, gIII phase gene III; RBS Ribosomal binding site; ompA outer membrane protein A signal sequence; phoA alkaline phosphatase signal sequence; L-His6 PGGSGH6 linker.

The present invention provides novel tricistronic vectors that are useful in multiple contexts. The inventors surprisingly found that tricistronic vectors may constructed to express three polypeptide molecules in a suitable yield under the control of a single promoter, with the additional feature that the expressed polypeptide domains can maintain function and interact with each other. Another surprising was the observation that all three polypeptides could be exported to the periplasm of a prokaryotic host following expression in the host's cytosol/cytoplasm, and that the expressed polypeptides could interact or otherwise associate in the periplasmic space. Vectors according to the present invention are suitable for use in a number of prokaryotic expression systems.

A. Components of a Vector of the Invention

The components of a tricistronic vector of the present invention include: (i) nucleic acid sequences encoding three polypeptide molecules (non-fused to each other) and (ii) a single promoter that controls expression of all three polypeptides. The polypeptide-encoding nucleic acid sequences encode, for example, (i) an immunoglobulin (Ig)-presenting polypeptide domain, (ii) a first Ig domain, and (iii) a second Ig domain. In addition, a vector of the invention preferably contains a ribosome binding site 5'-ward of each of the foregoing polypeptide molecules, which can enhance expression levels. Upon expression, the two Ig domains associate to form a functional immunoglobulin fragment, which further associates with the Ig-presenting domain, thereby permitting, for example, display of the functional immunoglobulin fragment on the surface of a filamentous phage.

A vector of the invention may optionally contain nucleic acid sequences encoding at least two associating agents, one of which can be fused to (or comprised within) the Ig-presenting and the other of which can be fused to (or comprised within) the first Ig polypeptide or second Ig polypeptide. Preferably, subsequent to expression of the vector, the Ig-presenting polypeptide and an Ig polypeptide interact with each other via their respective associating agents, and the two Ig polypeptides associate, e.g., by self-association, hydrogen bonding, van der Waals forces, or via an associating agent(s). The foregoing interaction and association interaction and association preferably occur in the periplasm of the prokaryotic host; however, the invention also contemplates association and interaction in the host's cytosol.

a. Promoter:

As used herein, a "promotes" for use in a tricistronic vector of the invention is a promoter that is capable of driving the expression of (i.e. that is functionally linked to) a nucleic acid construct that encodes at least three independent polypeptide molecules (e g., an Ig-presenting domain and two Ig domains), where those polypeptides are not expressed as fusion proteins with each other. Suitable promoters for use in the invention include, but are not limited to, the lac/operon promoter, CMV promoter $P_{bad}$, $P_{tet}$, $P_{ara}$, $P_{ADH1}$, $P_{GAL}$, $P_{EF-1\alpha}$, $P_{SV40}$, EM-7 promoter, $P_{TEF1}$, $P_{RSV}$, $P_{UbC}$.

Prokaryotic promoters of the invention can be either constitutive or, more preferably, regulatable (i.e., inducible or derepressible). Further examples of suitable prokaryotic promoters include promoters capable of recognizing the T4 (Malik et al., *J. Biol. Chem.* (1984) 263:1174-1181; Rosenberg et al., *Gene* (1987) 59:191-200; Shinedling et al., *J. Molec. Biol.* (1987) 195:471-480; Hu et al., *Gene* (1986) 42:21-30), T3, Sp6, and T7 (Chamberlin et al., *Nature* (1970) 228:227-231; Bailey et al., *Proc. Natl. Acad. Sci. (U.S.A.)* (1983) 8024:2814-2818; Davanlook et al., *Proc. Natl. Acad. Sci. (U.S.A.)* (1984) 81:2035-2039) polymerases; the $P_R$ and $P_L$ promoters of bacteriophage lambda (THE BACTERIOPHAGE LAMBDA, Hershey, A. D., Ed., Cold Spring Harbor Press, Cold Spring Harbor, N.Y. (1973); LAMBDA II, Hendrix, R. W., Ed., Cold Spring Harbor Press, Cold Spring Harbor, N.Y. (1980)); the trp, recA, heat shock, and lacZ promoters of *E. coli*; the α-amylase (Ulmanen et al., *J. Bacteriol* (1985) 162:176-182) and the Σ28-specific promoters of *B. subtilis* (Gilman et al., *Gene* (1984) 32:11-20); the promoters of the bacteriophages of *Bacillus* (Gryczan, T. J., In: THE MOLECULAR BIOLOGY OF THE BACILLI, Academic Press, Inc., NY (1982)); *Streptomyces* promoters (Ward et al., *Mol. Gen. Genet.* (1986) 203,468-478); the int promoter of bacteriophage lambda; the bla promoter of the β-lactamase gene of pBR322, and the CAT promoter of the chloramphenicol acetyl transferase gene of pBR325, etc. Prokaryotic promoters are reviewed by Glick, B. R. (*J. Indust. Microbiol.* (1987).1:277-282); Cenatiempo, Y. (*Biochimie* (1986) 68:505-516); Watson, J. D., (In: MOLECULAR BIOLOGY OF THE GENE, 4th Ed., Benjamin/Cummings Publishing Co., inc., Menlo Park, Calif. (1987)); Gottesman, S. (*Ann. Rev. Genet.* (1984) 18:415-442)). Other prokaryotic promoters that may be used include other *E. coli* promoters (Harley et al., *Nucl. Acid Res.* (1987) 15:2343-2361), and *Streptomyces* promoters (Strohl, *Nucl. Acid Res.* (1992) 20:961-974) for use in *Streptomyces* species expression hosts. All of the foregoing references are incorporated by reference.

b. Immunoglobulin-Presenting Polypeptide:

An "immunoglobulin-presenting" or "Ig-presenting" polypeptide or polypeptide domain, as used herein, is a (poly) peptide or protein/polypeptide domain that can interact with at least one immunoglobulin polypeptide, such that the immunoglobulin(s) are able to specifically bind, or are involved in the process of specifically binding, an antigen. An Ig-presenting polypeptide preferably interacts with an Ig domain via an associating moiety that customarily is fused to (or contained within) the Ig-presenting domain.

Suitable-Ig-presenting domains include a phage coat (capsid) protein, for example a filamentous phage coat protein. A suitable phage coat protein can be, for example, gene III protein (gIIIp), gene VI protein (gVIp), gene VII protein (gVIIp), gene VII protein (gVIIIp), and gene IX protein (gIXp). A preferred phage coat protein is gIIIp. A phage coat protein may be either a wild type or a modified protein. A "wild type phage coat protein" refers to any protein forming the phage coat of a naturally occurring bacteriophage. The sequences of the foregoing phage coat proteins (including the differences between the closely related members of the filamentous bacteriophages such as f1, fd, and M13) are well known to those of skill in the art (see, e.g., Kay et al, 1996). The skilled artisan will recognize that other Ig-presenting domains are suitable for use in the present invention.

An Ig-presenting polypeptide of the invention also may be a truncated or modified variant of a phage coat protein (e.g., the C-terminal domain of gIIIp). In this regard, a "truncated" or "modified" variant (or a functional fragment thereof) refers to any phage coat protein that has been modified by deleting, inserting and/or substituting at least part of the wild type sequences. Examples of such variants include truncated gene III protein variants that have been found in bacteriophage mutants (see, for example, Crissman & Smith, 1984) or that have been generated for use in phage display methods (e.g. Bass et al., 1990; Krebber, 1996).

The invention also contemplates the use of other Ig-presenting polypeptides. An Ig-presenting polypeptide also may be a green fluorescent protein (gfp), any protein of the cell surface or of the cell wall of bacterial cell, or any protein of a bacteriophage or virus coat c. Immunoglobulin or "Ig" Polypeptide or Domain An "immunoglobulin" or "Ig" polypeptide or domain hereby is defined as a domain of the protein class IgG, IgM, IgE IgA, and IgD (and any subclass thereof), and includes all conventionally known antibodies and functional fragments thereof. A "functional fragment" refers to a fragment of an immunoglobulin which retains the antigen-binding moiety of an immunoglobulin. A preferred class of immunoglobulins for use in the present invention is IgG. More specifically, an immunoglobulin domain of the invention can include the domain of (i) a F(ab')$_2$, fragment, or (ii) a Fab fragment. The F(ab')$_2$, or Fab may be engineered to minimize the intermolecular disulphide interactions that occur between the $C_{H1}$ and $C_L$ domains. An Ig polypeptide may have an amino acid sequence derived from that of an antibody isolated from nature or derived from a natural source, or may have a sequence that is designed in silico and encoded by a nucleic acid that is synthetically created. In silico design of an antibody sequence can be achieved, for example, by analyzing a database of sequences and devising a polypeptide sequence utilizing the data obtained therefrom. Methods for designing and obtaining such in silico-created sequences are described, for example, in U.S. Pat. No. 6,300,064 to Knappik et al., which hereby is incorporated by reference in its entirety.

A tricistronic vector of the invention preferably encodes two Ig polypeptides that interact with each other and form a functional (antigen-binding) molecule. Interaction between the two Ig polypeptides typically is mediated by residues that belong to each Ig polypeptide. To this end, the first and second polypeptide can comprise heavy and light chain regions of an antibody that associate via non-covalent interactions between corresponding heavy and light chain domains, such as between VH and VL in an Fv fragment, or between VH/VL and CH1/CL in a Fab fragment Additionally, heavy and light chain regions of an antibody may associate by forming disulphide bonds between the two chains, such as is possible in a Fab fragment The present invention specifically contemplates the interaction of two Ig polypeptides by mechanisms other than formation of one or more inter-chain disulfide bonds., e.g., via a linker moiety that is non-covalently attached to at least one of the Ig domains, via hydrogen bonds, via van der Waals interactions, or via peptidic association domains fused to the Ig polypeptides, such as described in U.S. Pat. No. 6,294,353 to Pack et al., which hereby is incorporated by reference.

An "associating agent" for use in the present invention is defined as an agent that can bring about the interaction between expressed Ig-presenting and Ig polypeptides. An expressed associating agent of the invention is fused to, or comprised within, an Ig-presenting polypeptide and a complementary associating agent is fused to, or comprised within, an Ig polypeptide. The foregoing associating agents may be two different agents, or may be two identical or substantially identical agents. An associating agent according to the invention preferably contains a cysteine residue that is available for the formation of an intermolecular disulphide linkage.

Preferably, the associating agents are selected so that they do not interfere with the desired function of the fully associated protein complex. Typically, therefore, the associating agents are suitable amino acid residues that are located outside the region(s) deemed to be responsible for a putative function of the (poly)peptide/protein of interest such as binding to a target For example, a cysteine residue that is intended to form an inter-chain disulfide bond is positioned at, or in the vicinity of, either the N- or the C-terminus of a polypeptide.

Other suitable associating agents include those which (i) can be fused to the C-terminal end of an Ig polypeptide (or within about-15 amino acid residues thereof) and (ii) can interact with an associating agent fused to or comprised within an Ig-presenting polypeptide. Likewise, suitable agents include any which (i) can be fused N-terminally to (or comprised within) an Ig-presenting polypeptide (e.g., phage coat protein) and (ii) can interact with an associating agent fused to or comprised within an Ig polypeptide. A specific example of a pair of associating agents in this regard is an avidin-biotin complex.

In the context of the present invention, a cysteine residue is "available for the formation of an intermolecular disulfide bond" if the residue is (i) located N-terminal, C-terminal, or internal to a polypeptide and (ii) accessible for the formation of a disulfide bond with a second residue of the same or different kind. This includes cysteine residues that are buried, and thus not accessible in the "final" polypeptide molecule, but which are accessible in an intermediate compound formed in the course of expression, processing and/or transport in a host cell.

In one embodiment, two associating agents may associate, or attach, by the formation of a disulfide bond between (i) at least one cysteine residue present in an Ig polypeptide and (ii) a second cysteine residue present within an Ig-presenting domain that is a wild type phage coat protein. In the case of filamentous bacteriophage fd, for example, wild type proteins contain the following cysteine residues: Cys7, Cys36, Cys46, Cys53, Cys188, Cys201, Cys354, and Cys371 of protein m; residue Cys84 of protein VI; residue Cys22 of protein VII; residue Cys16 of protein IX Any one or more of these residues may act as an associating agent A tricistronic vector of the invention also may contain one or more ribosome binding sites. A ribosomal binding site (Shine-Dalgarno sequence) is a purine rich sequence that in on bacterial mRNA is located about ten nucleotides 5-primeward of the initiator codon for a particular polypeptide. A shine-Dalgarno sequence is involved in the binding of the ribosome and the mediating of efficient translation of the respective-gene.

A tricistronic vector of the invention also may contain one or more nucleic acid sequences that encode a signal or secretory polypeptide. A "signal" or "secretory" polypeptide hereby is defined as a polypeptide responsible for transporting another polypeptide from bacterial cytosol to bacterial periplasm. A signal or secretory polypeptide of the invention preferably is located N-terminal to the polypeptide to be transported to the periplasm. The use of one or more secretory polypeptides can be especially advantageous in the context of phage display technology, as described, infra, whereby the secretory polypeptide (i) is linked to a encoded polypeptide, and (ii) directs the corresponding polypeptide to the periplasmic space of its prokaryotic host cell. Secretory polypeptides include, for example, ompA and phoA, gene III signal sequence, st II, and pelB, each of which can be used in a prokaryotic expression system. Other nucleic acid sequences encoding secretory peptide sequences are well known in the art and may also be used in the present invention. In one aspect of the invention, a secretory nucleic acid sequence (e.g., ompA) is linked to the nucleic acid sequence that encodes a first Ig domain, while a second secretory nucleic acid sequence (e.g., phoA) is linked to the nucleic acid sequence that encodes a second Ig domain. A secretory nucleic acid sequence also can be linked to the nucleic acid sequence that encodes an Ig-presenting polypeptide. Alternatively, the secretory domain can be an inherent property of an Ig-presenting domain of the invention.

A tricistronic vector of the invention also may contain one or more nucleic acid sequences that can encode a "polypeptide linker" that functions to link an associating agent to an Ig-presenting and/or an Ig domain. In this context, the linker can be viewed as a "spacer" between an associating agent and its respective polypeptide. This linker preferably-contains about 1-50 amino acids, and preferably 5 to 15 amino acids. Typically, a linker consists of glycine-serine rich stretches, but can also contain other amino acid residues. The size can also be variable according to the purpose of the linker.

A tricistronic vector of the invention also can be constructed so as to contain one or more affinity tags (e.g., His6 tag) that is fused to one of the Ig domains, for example. An affinity tag can be used to purify or isolate a population of-Ig molecules bearing this tag.

A tricistronic vector of the invention also can be constructed so as to contain one or more restriction sites that facilitate cloning, sub-cloning, or other manipulation of the vector. For example, when a plurality of restriction sites are present, unique restriction sites can be engineered to flank a particular segment of the vector, thereby making the vector modular. The feature of modularity can be advantageous, e.g., for subsequent modification of the tricistronic vector at one or more discrete positions. According to this approach, a particular segment of the tricistronic vector can be excised and substituted with another desired segment, using convention technology. A library such as the HuCAL antibody library described in U.S. Pat. No. 6,300,064 to Knappik et al., is particularly preferred for use in a vector of the present invention.

Figure 2A:
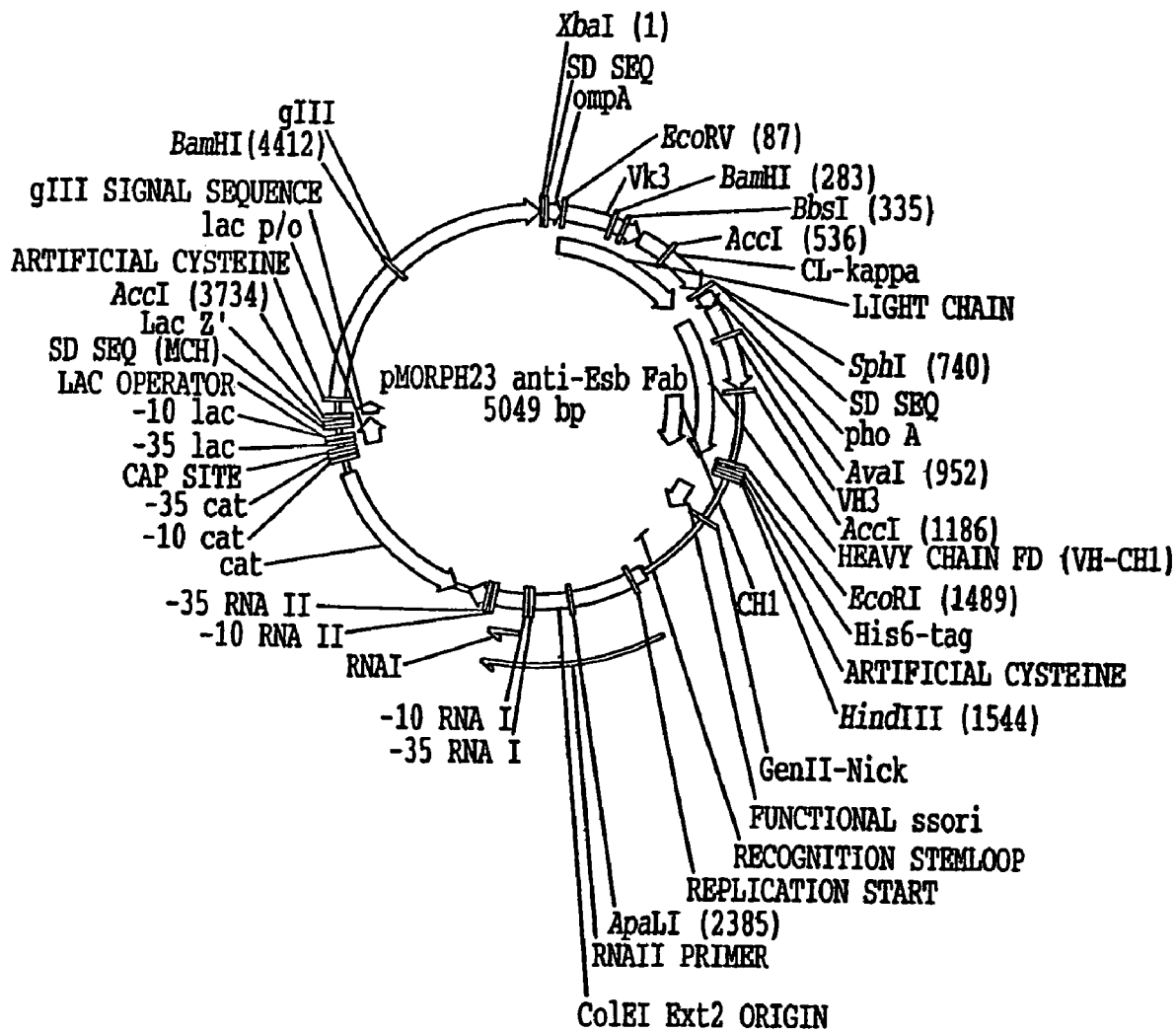
FIG. 2A is a vector map of an illustrative vector according to the present invention.
Figure 3:
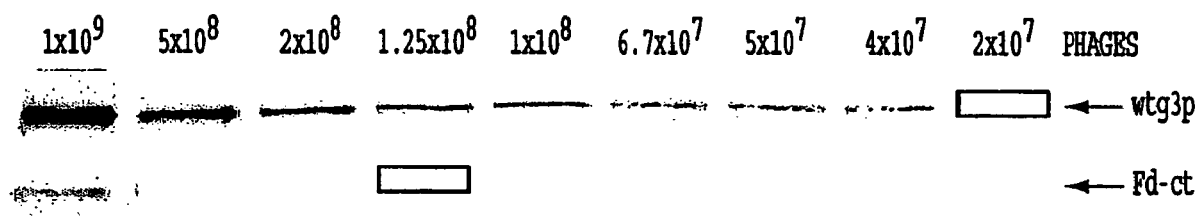
FIG. 3 is a gel that represents a quantitative analysis (by anti-gIIIp Western blot) of the mean display rate of Fab on the surfaces of phage.

An illustrative, non-limiting embodiment of a vector according to the invention (pMORPH23) is set forth in FIG. 2A. According to FIG. 2A, pMORPH23 contains a ColEI origin of replication, a functional origin for single stranded replication, and a chloramphenicol-resistance gene. The tricistronic operon is under the control of an inducible lac promoter/operator region. All functional modules are flan*ed by unique restriction sites. The first expression cassette contains the signal sequence of geneIII, and the engineered full-length (mature) geneIII sequence with an additional N-terminal cysteine residue. The second expression cassette, which is preceded by a ribosomal binding site (SD-Seq), encodes the light chain of an Ig and contains the bacterial signal sequence ompA followed by VL and CL. The third expression cassette, which is preceded by a ribosomal binding site (SD-Seq), contains a heavy chain Fd (VH1+CH1) with an additional C-terminal cysteine. The bacterial signal sequence phoA is followed by VH1 and CH1, whereby a glycine/serine-rich linker and a His6-tag act as a spacer for the introduced cysteine to the Fd chain.

B. Constructing a Vector of the Invention

Methods for constructing vectors comprising nucleic acid molecules are known in the art (see, e.g., Sambrook et al., 1989; Ausubel et al., 1994). A vector map of a representative vector of the invention (pMORPH23) is provided in FIG. 2A, with its nucleic acid sequence provided in FIG. 2B.

C. Representative Uses of a Vector According to the Invention

A tricistronic vector of the invention can be used, or can be modified to be used, in a variety of prokaryotic expression systems. A suitable host cell is any cell that permits expression and subsequent interaction of the three principal polypeptide domains (i.e., Ig-presenting and two Ig domains). Methods for introducing vectors into appropriately chosen host cells, and causing or allowing the expression of polypeptides are known in the art (see, e.g., Sambrook et al., 1989; Ausubel et al; 1994).

A vector according to the invention, is particularly suited for expression in an *E.coli* host cell. In this regard, the vector can be in the form of a phagemid vector. A phagemid consists of elements of conventional plasmid vectors (e.g., marker gene, cloned genes, plasmid origin of replication) and of elements of filamentous phage (e.g., gIII, PS and phage ori). A phagemid can be introduced into a host cell, and subsequently be cultivated and amplified therein like a plasmid. Phagemid vectors are well, known in the art.

A phagemid does not encode all of the genes necessary to permit assembly of viral particles and requires "rescue" in a host cell with a helper phage. The helper phage provides the missing phage genes that permit assembly of the viral particles. It will be appreciated that use of a phagemid/helper phage system an result in production of particles that contain either the helper phage genome or the phagemid. Methods of preferentially packaging the phagemid are well known in the art, for example by using a helper phage, such as M13 K07 that contains a functional, but defective, DNA origin of replication so that phagemid is preferentially packaged into phagemid particles. Methods for the introduction of genetic material required to produce progeny phage or phagemid particles in appropriate host cells, and for causing or allowing the generation of such particles are well known in the art (see, e.g., Kay et al, eds. (1996) PHAGE DISPLAY OF PEPTIDES AND PROTEINS: A LABORATORY MANUAL. Academic Press, Inc., San Diego).

A vector of the invention can, accordingly, be use to carry out a method for producing a polypeptide or protein having a desired property. This method includes the steps of (i) providing a collection of bacteriophage particles that present on their surface a diverse collection of one or more Ig polypeptides as defined herein; and (i) screening and/or selecting the diverse collection for at least one Ig domain having the desired property. Here, the term "desired property" refers to a property that (a) one of the polypeptides or proteins out of the diverse collection should have and (b) forms the basis for screening and/or selecting the diverse collection. A property might be the ability to: bind a target, block a target, or activate a target-mediated reaction. A further property may be, for example, enzymatic activity, or any other properties known to those skilled in the art Methods for identifying suitable experimental formats and for carrying out necessary steps for performing screening and/or selection are well known in the art.

A preferred property of an Ig polypeptide is specific binding to a target. The target can be presented to the diverse collection of bacteriophage particles in a variety of ways well known to one of ordinary skill, for example, by coating on surfaces for solid phase biopanning, by linkage to particles such as magnetic beads for biopanning in solution, or by display on the surface of cells for whole cell biopanning.

Bacteriophage particles that display (via an Ig-presenting domain) one or more Ig polypeptides (which are bound to a target) can be recovered by a variety of methods well known to one of ordinary skill. If the associating agents link the Ig-presenting polypeptide and Ig polypeptide via a disulfide bond, then the specifically bound Ig-target complexes can be treated under reducing conditions (e.g., incubation with DTT) to cleave the disulfide bonds and to recover the specific bacteriophage particles for further rounds of biopanning and/or for identification of the Ig polypeptide domains specifically binding to said target

EXAMPLES

The present invention can be better understood with reference to the following examples, which are not intended to limit the scope of the invention as described above.

Example 1

General Protocol for Quantitative Analysis of Display of Antibody Fragments on Phage The protocol, which also applies to Examples 2-6, was performed according to Johansen, L. K. et al. (1995), *Protein Engng.* 8, 10, 1063-1067. Different dilutions of the same phage preparation were subjected to a protein gel. However, in Examples 3, 5 and 7, no reducing agents were added, due to the presence of cysteines as associating agents. The proteins of the protein gel were transferred to a membrane. gIIIp protein on the membrane was detected by anti-gIIIp antibody (Western blot). Then, one wild-type gene III protein ("wt-gIIIp") band and one band of the antibody-gIIIp linkage, which have the same intensity were analysed. Given (i) the number of phages loaded, (ii) the molar ratio of both proteins, and (iii) the assumption of 5 wtgIIIp-proteins per phage, the mean number of antibody fragments displayed per phage could be calculated. FIG. 1 provides expression data of a dicistronic Fab vector (pMORPH18) using conventional (i.e., gIIIp-fusion) display. The data indicate a ratio of Fd-gIIIct:wtgIIIp=$1.25\times10^8$ phage:$2\times10^7$ phage. This correlates to the presentation of 1 Fd-gIIIct per 6.25 wtgIIIp; in other words, 1 Fd-gIIIct per 1.25 wtgIIIp. Accordingly, the mean number of Fabs per phage in this experiment was 0.8.

Abbreviations throughout Fd=VH-CH1; Fd-ct=Fd-gIIIct & VH-CH1-gIIIct; g3p=gIIIp.

Example 2

Display Determination of Monocistronic scFv Vector, Using Conventional Display

Figure 4A:
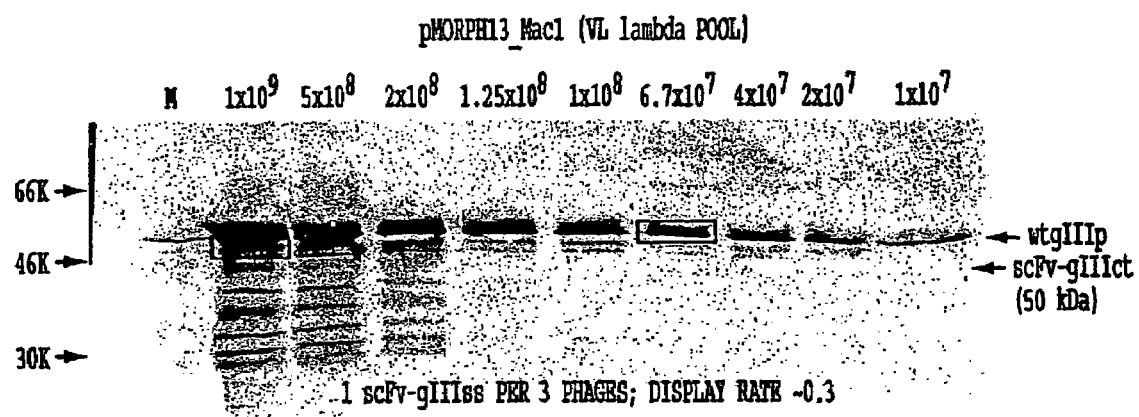
FIG. 4A is a gel that represents the display rate of a monocistronic scFv vector (pMORPH13) encoding scFvs from a VL-λ pool (conventional display).
Figure 4B:
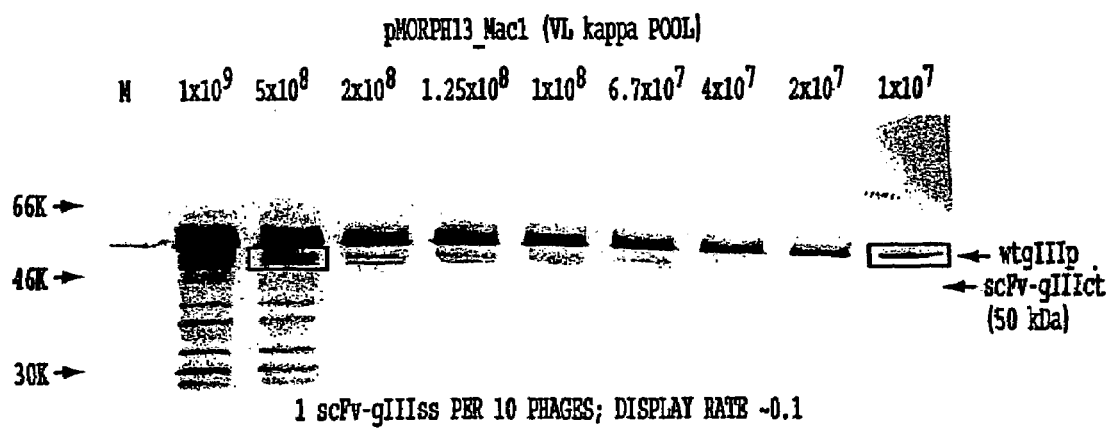
FIG. 4B is a gel that represents the display rate of a monocistronic scFv vector (pMORPH13) encoding scFvs from a VL-κ pool (conventional display).
Figure 4C:
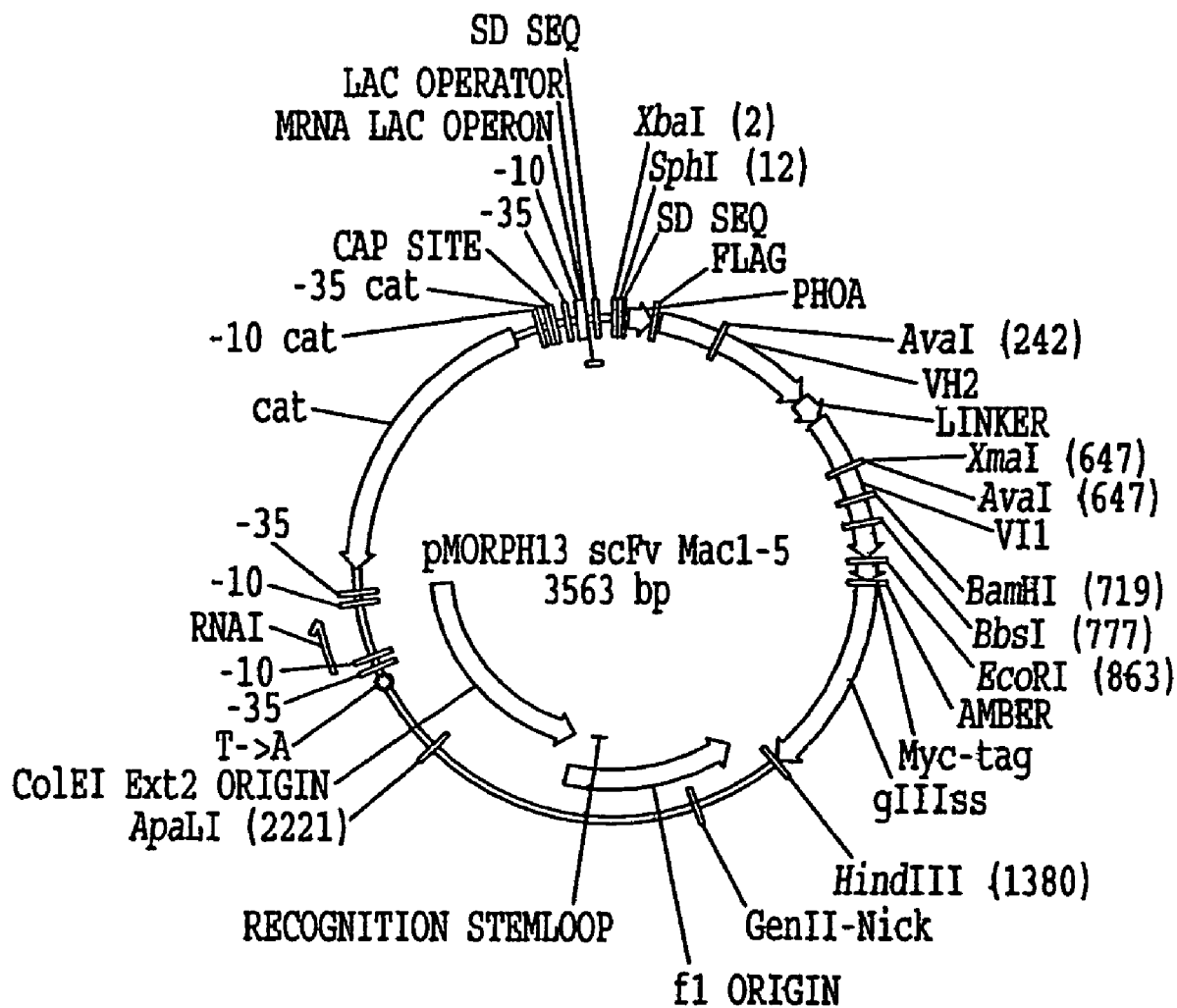
FIG. 4C is a Vector map for pMorph13 scFv Mac1-5

A protocol as disclosed in Example 1 was carried out for performing a quantitative display analysis of a monocistronic scFv vector (pMORPH13), using conventional phage display. FIG. 4A provides expression data of the (pMORPH13) vector from a VL/λ pool; and FIG. 4B provides expression data of the (pMORPH13) vector from a VL-κ pool. The data indicate a ratio of scFv-gIIIct:wtgIIIp=$1\times10^9$phage:$6.7\times10^7$ phage in FIG. 4A, and a ratio of scFv-gIIIct:wtgIIIup=$5\times10^8$phage:$1\times10^7$ phage in FIG. 4B. Accordingly, the mean number of ScFv per phage in this experiment was approximately 0.3 and 0.1, respectively.

Example 3

Display determination of a Dicistronic scFv Vector, Using Cys Display

Figure 5A:
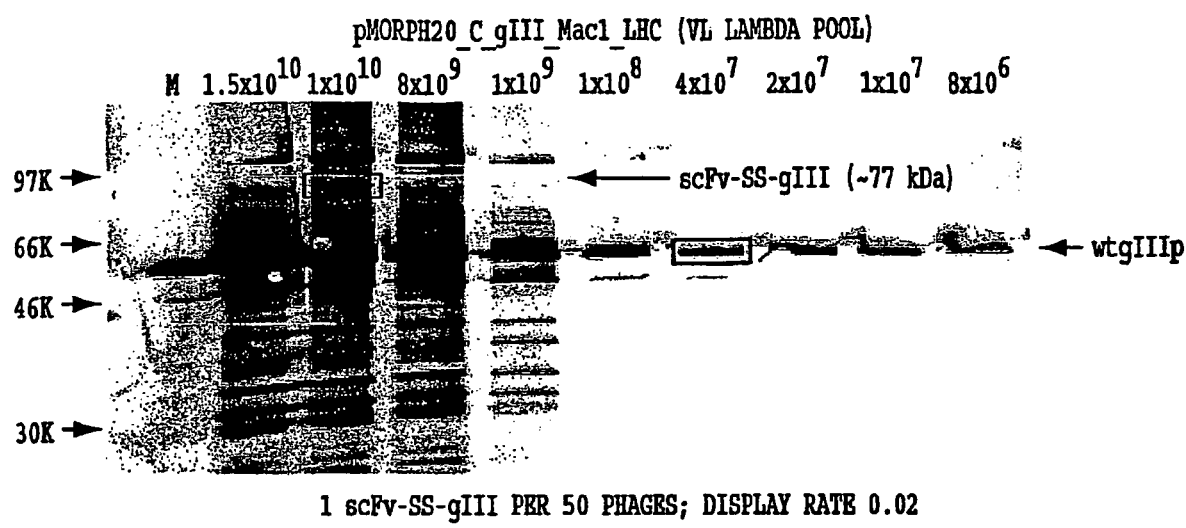
FIG. 5A is a gel that represents the display rate of a dicistronic scFv vector (pMORPH20) encoding scFvs from a VL-λ pool (display via Cys residues).
Figure 5B:
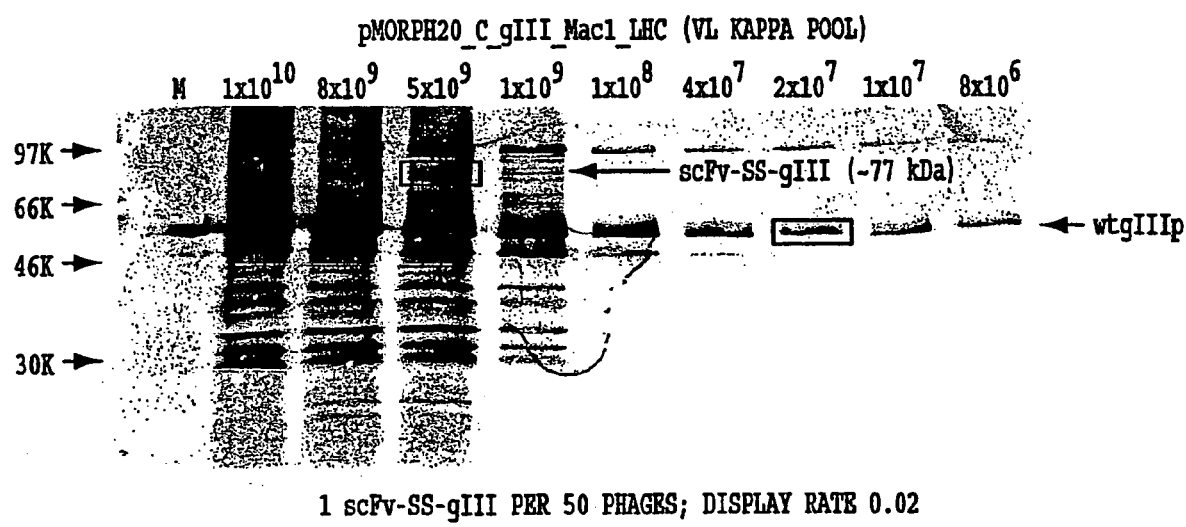
FIG. 5B is a gel that represents the display rate of a dicistronic scFv vector (pMORPH20) encoding scFvs from a VL-κ pool (display via Cys residues).

A protocol as disclosed in Example 1 was carried out (except with using reducing agents) for performing a quantitative display analysis of a dicistronic scFv vector (pMORPH20), using Cys display. FIG. 5A provides expression data of the pMORPH20 vector from a VL-λ pool; and. FIG. 5B provides expression data of the pMORPH-20 vector from a VL-κ pool. The data indicate a ratio of scFv-SS-gIIIct: wtgIIIp=1×10$^{10}$ phage:4×10$^7$ phage in FIG. 5A, and a ratio of scFv-SS-gIIIct:wtgIIIp=5×10$^9$*** phage:2×10$^7$ phage in FIG. 5B. Accordingly, the mean number of scFv per phage in this experiment was approximately 0.02 and 0.02 respectively.

Example 4

Display Determination of a Dicistronic Fab Vector, Using Conventional Display

Figure 6C:
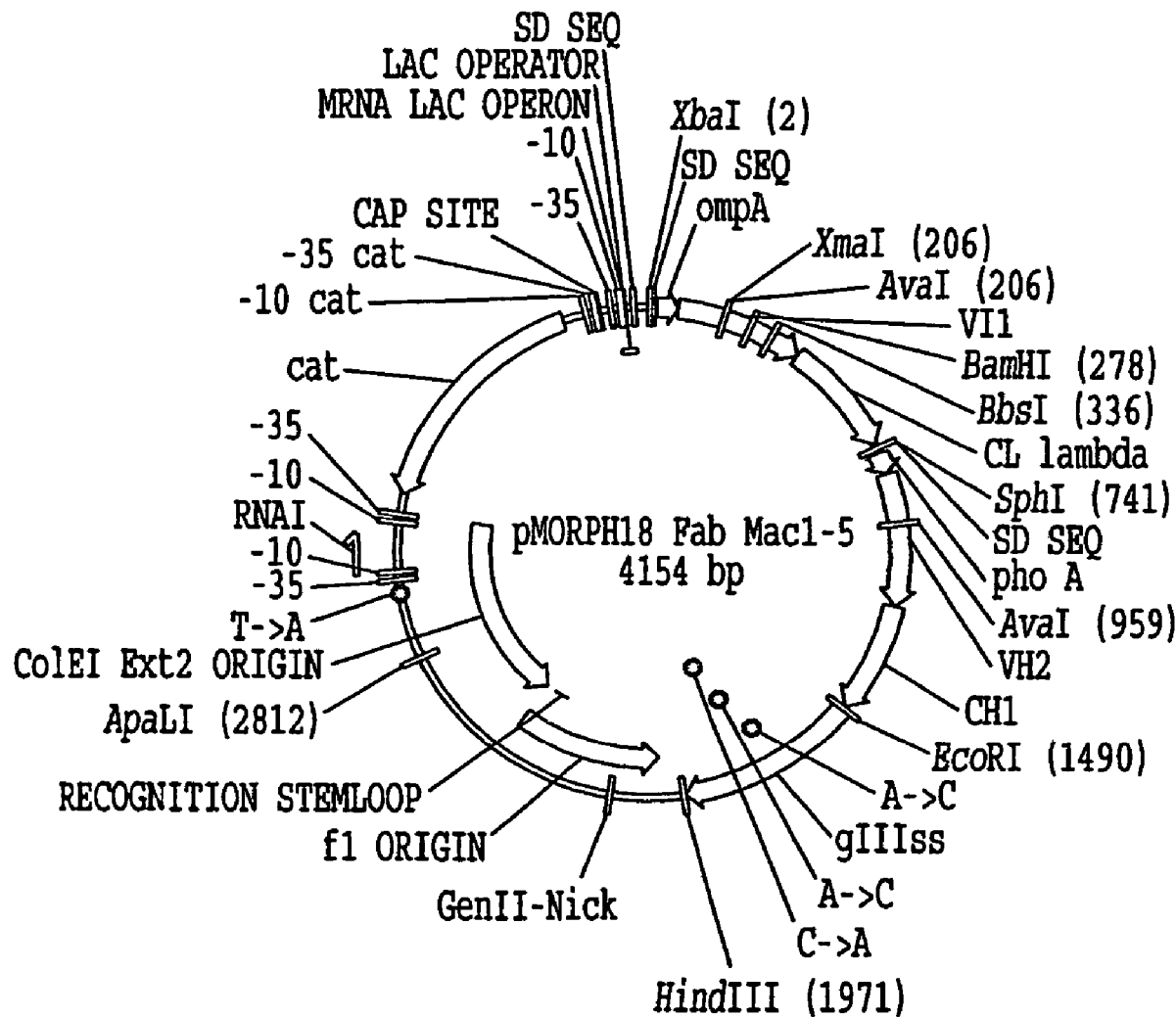
FIG. 6C is a Vector map of pMORPH®18-Fab Mac1-5

A protocol as disclosed in Example 1 was carried out for performing a quantitative display analysis of a dicistronic Fab vector (pMORPH18), using conventional phage display. FIG. 6A provides expression data of the pMORPH 8 vector (single Fab of framework. combination VH2-λ1); and FIG. 6B provides expression data of the pMORPH18 vector (single Fab of framework combination VH3-κ1). The data indicate a ratio of Fd-gIIIct:wtgIIIp=1.×10$^9$ phage:2×10$^7$ phage in FIG. 6A, and a ratio of Fd-gIIIct:wtgIIIp=1×10$^8$ phage:1×10$^7$ phage in FIG. 6B. Accordingly, the mean number of Fabs per phage in this experiment was approximately 0.1 and 0.5, respectively.

Example 5

Display Determination of a Dicistronic Fab Two-Vector System, Using Cys Display

Figure 7A:
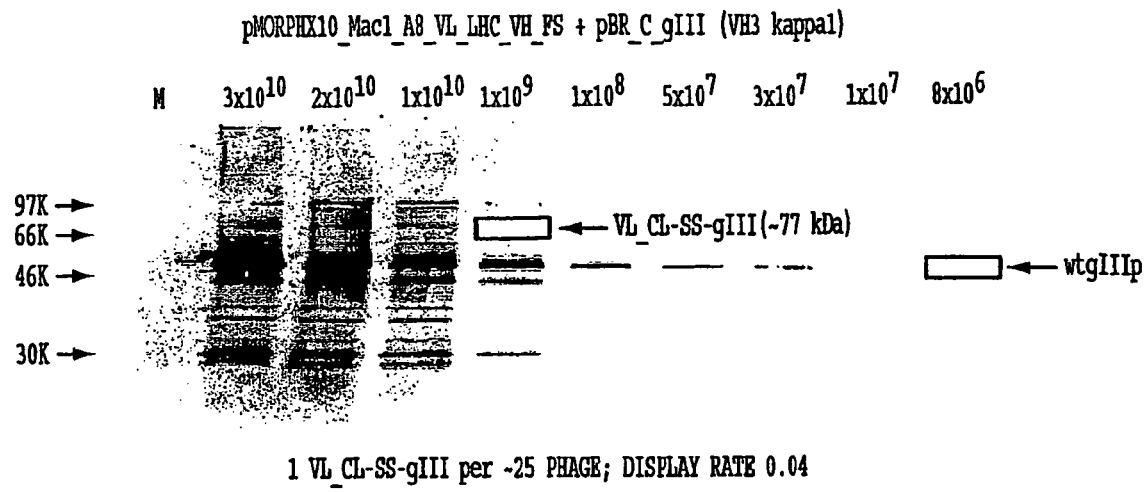
FIG. 7A is a gel that represents the display rate of a dicistronic Fab vector, using a two-vector system (pMORPHX10 & pBR_C_gIII) and encoding a Fab of framework combination VH3 κ-1, respectively (display via Cys residues).
Figure 7B:
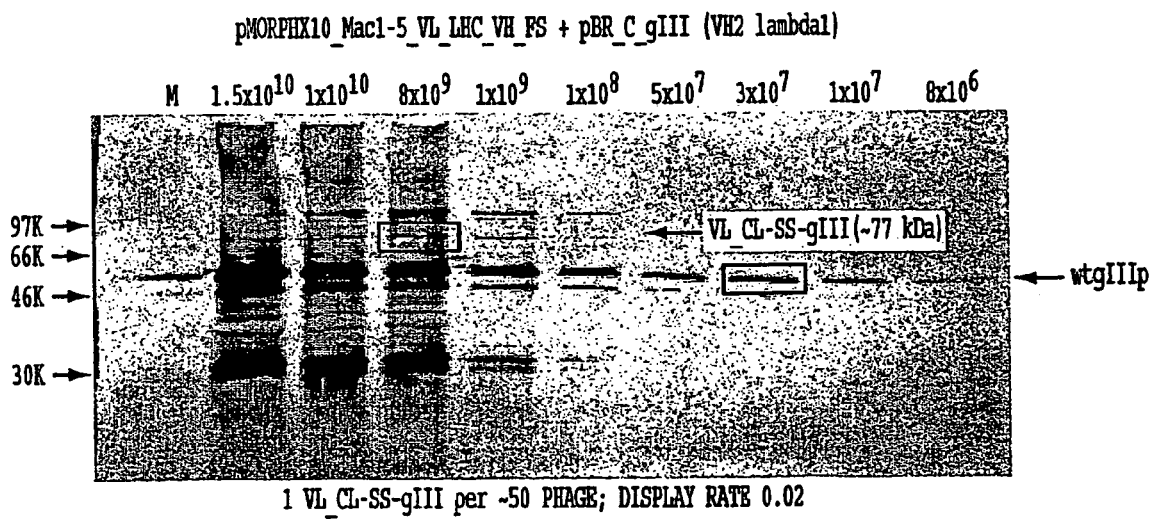
FIG. 7B is a gel that represents the display rate of a dicistronic Fab vector, using a two-vector system (pMORPHX10 & pBR_C_gIII) and encoding a Fab of framework combination VH2 κ-1, respectively (display via Cys residues).
Figure 7C:
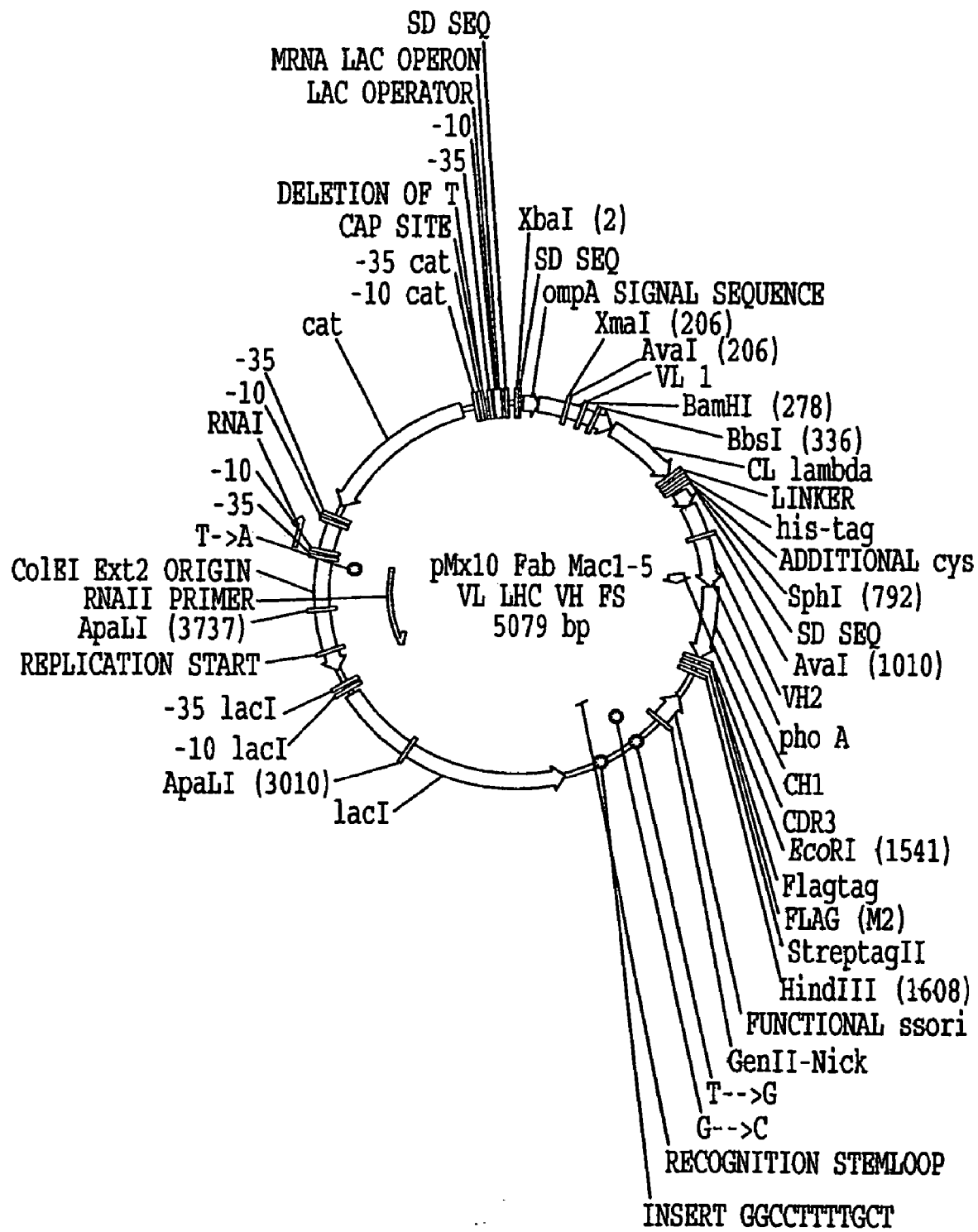
FIG. 7C is the vector map for pMORPHX10 Fab Mac1-5 VL LHC VH FS
Figure 7E:
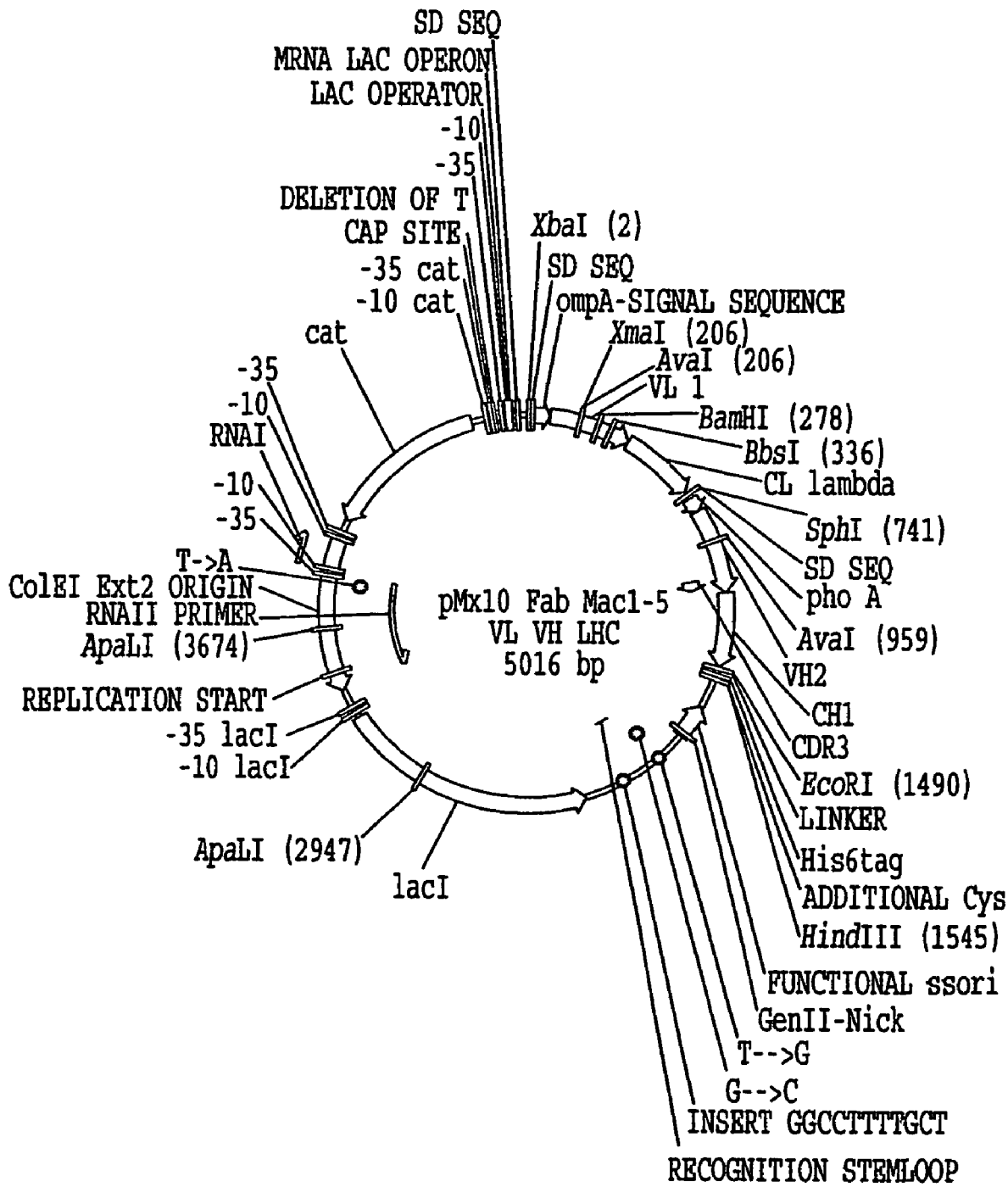
FIG. 7E is the vector map for pMORPHX10 Fab Mac1-5 VL VH LHC
Figure 7G:
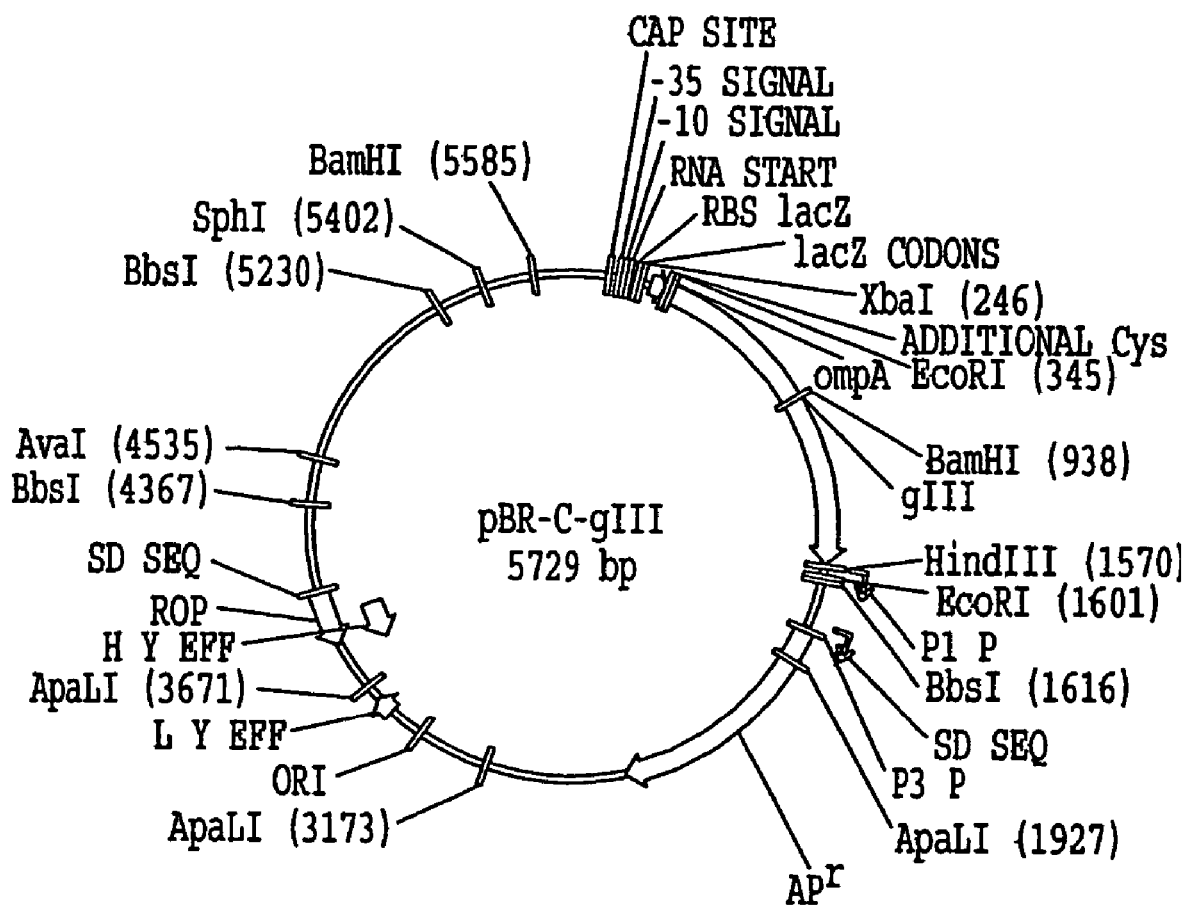
FIG. 7G is the vector map for pBR-C-gIII

A protocol as disclosed in Example 1 was carried out (except with using reducing agents) for performing a quantitative display analysis of a dicistronic Fab vector in a two-vector system (pMORPH10+pBR_C_gIII), using Cys display. FIG. 7A provides expression data of the pMORPH10 vector system (single Fab of framework combination VH3-κ1); and FIG. 7B provides expression data of the pMORPH10 vector system (single Fab of framework combination VH2-λ1). The data indicate a ratio of VL_CL-SS-gIII:wtgIIIp=1× 10$^9$ phage:8×10$^6$ phage in FIG. 7A, and a ratio of VL_CL-SS-gIII:wtgIIIp=8×10$^9$ phage:3×10$^7$ phase in FIG. 7B. Accordingly, the mean number of Fabs per phage in this experiment was approximately 0.04.and 0.02, respectively.

Example 6

Analysis of Display Rates and Efficiency in Phage ELISAs

The following table summarizes approximate display rates obtained in Examples 1-5:

TABLE I

| System | Vector(s) | Approximate display rates (Ig per Phage) |
|---|---|---|
| scFv conventional (monocistronic) | pMORPH13 | 0.1-0.3 |
| scFv CysDisplay (dicistronic) | pMORPH20 | 0.02 |
| Fab conventional (dicistronic) | pMORPH18 | 0.1-0.8 |
| Fab CysDisplay (dicistronic) | pMORPHX10 + pBR_C_gIII | 0.02-0.04 |

From this table, two trends are understood. First, the display rates decrease as much as 2.5 to 40 fold when using CysDisplay in lieu of conventional display. Second, the display rates decrease as much as 5 to 15 fold when moving from a monocistronic conventional display vector to a dicistronic CysDisplay vector. Accordingly, CysDisplay phage generally showed reduced display rates in comparison to phage containing conventional genetic fusions of antibody fragments to gIII (or gIIIct fragment). Because it would be highly undesirable to work with display rates lower than 0.04 Fabs per phage, the use of a tricistronic Fab vector that additionally was engineered for CysDisplay was thought not to be possible, based on the foregoing trends of decreased display rates.

Example 7

Display Determination of Tricistronic Fab Vector, Using Cys Display (Single Vector System)

Figure 8A:
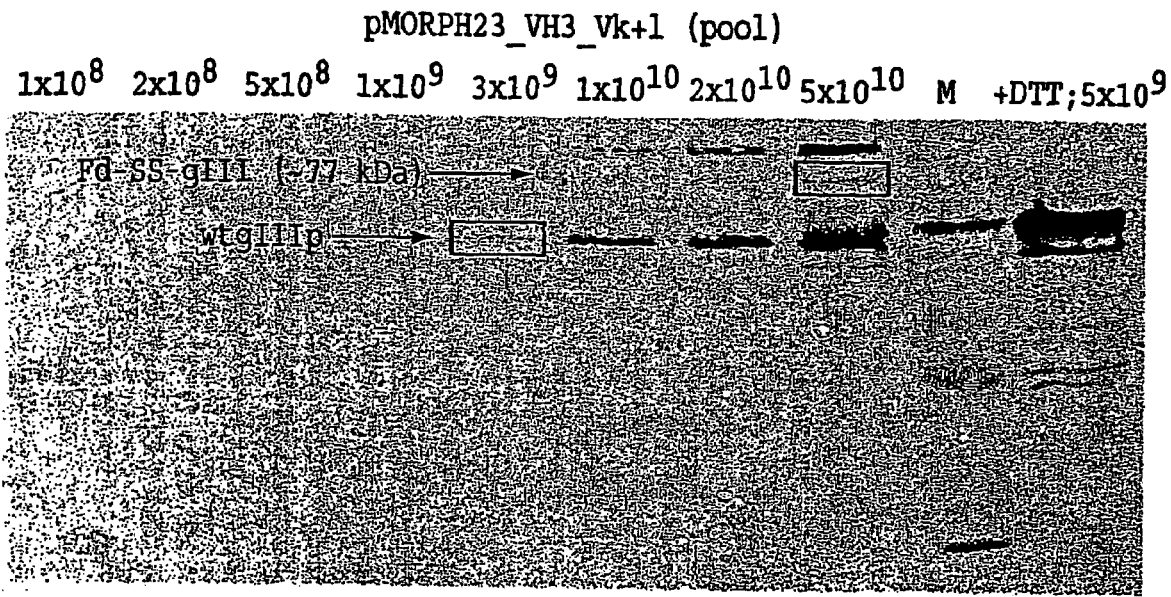
FIG. 8A is a gel that represents the display rate of a tricistronic Fab vector (pMORPH23) encoding a Fab pool (framework combinations VH3 κ/λ).
Figure 8B:
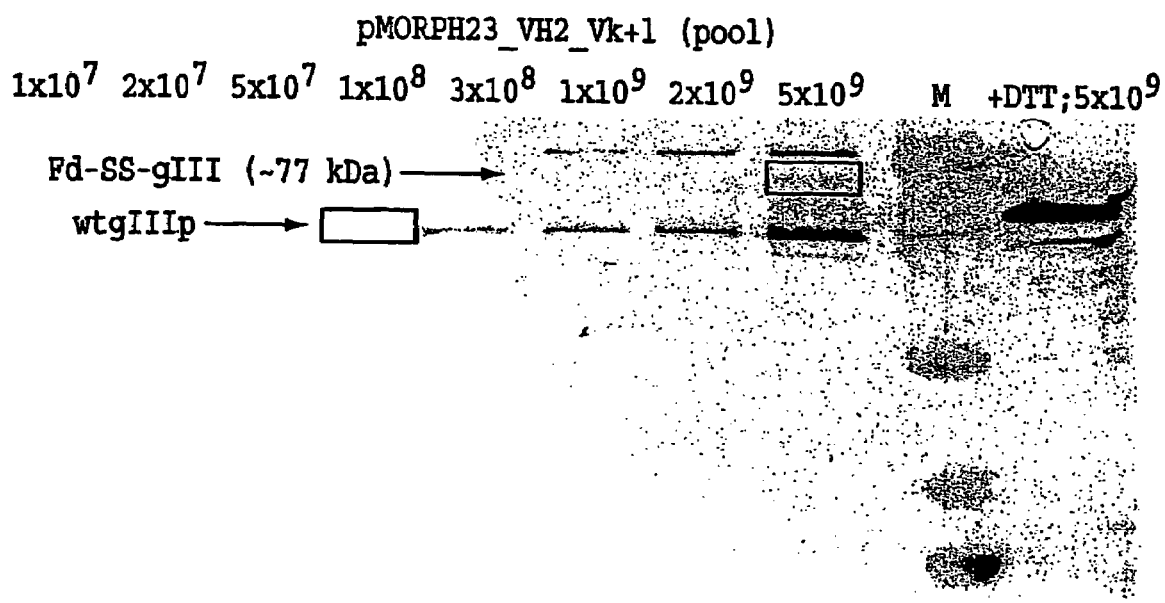
FIG. 8B is a gel that represents the display rate of a tricistronic Fab vector (pMORPH23) encoding a Fab pool (framework combinations VH3 κ/λ).

A protocol as disclosed in Example 1 was carried out (except with using reducing agents) for performing a quantitative display analysis of a tricistronic Fab vector (pMORPH23), using Cys display. FIG. 8A provides expression data of the pMORPH23 vector from a VH3+κ/λ pool; and FIG. 8B provides expression data of the pMORPH23 vector from a VH3+κ/λ pool. The data indicate a ratio of Fd-SS-gIII:wtgIIIp=5×10$^{10}$ phage:3×10$^9$ phage in FIG. 8A, and a ratio of Fd-SS-gIII:wtgIIIp=5×10$^9$ phage:1×10$^8$ phage in FIG. 8B. Accordingly, the mean number of Fabs per phage in this experiment was approximately 0.3 and 0.1, respectively.

As is shown in Table II below, the tricistronic Fab CysDisplay vector (pMORPH23) yield improved Fab display rates when compared to the dicistronic Fab CysDisplay system, which always needs a second vector providing the Cys-gIII construct. When using a constant amount of phage in the foregoing examples, the signals obtained with the tricistronic system were higher than those obtained with the dicistronic system. This indicates an increased display rate with the tricistronic version, which was unexpected.

TABLE II

| System | Vector(s) | Approximate display rates (Ig per Phage) |
|---|---|---|
| scFv conventional | pMORPH13 | 0.1-0.3 |
| scFv CysDisplay | pMORPH20 | 0.02 |
| Fab conventional | pMORPH18 | 0.1-0.8 |
| Fab CysDisplay dicistronic | pMORPHX10 + pBR_C_gIII | 0.02-0.04 |
| Fab CysDisplay tricistronic | pMORPH23 | 0.05-0.3 |

Example 8

Comparison of Dicistronic and Tricistronic Fab Cys Display Vectors in Phage ELISA Phage preparations (i) anti-Mac1 I-domain, (ii) Fab Mac1-5 and (iii) Mac1_A8 were expressed from the dicistronic CysDisplay vector (pMORPHX10+pBR_C_gIII; two-vector-system), the tricistronic CysDisplay vector (pMORPH23) and the dicistronic, conventional Fab vector (pMORPH18) and displayed on phage. The phage were concentrated and the titer of the phage preparations was determined.

Maxisorp wells of a microtiter plate were coated with 1.00 μl Mac1 I-domain protein per well (concentration of the antigen solution in PBS: 50 μg/ml) overnight at 4° C. The antigen solution was removed and the coated wells were washed with PBS. Next, the antigen-coated wells were blocked with 300 μl 5% MPBST for 1 hour at room temperature. At the same time, an aliquot of each phage preparation (100 μl per well, 7.5E+9 phages) 1:1 was mixed with 10% MPBST (incl. 0.1% Tween20). The phage were incubated for 1 hour at room temperature. The coated wells were washed 3× with PBS. Then, 200 μl of pre-blocked phage solution was transferred into each coated well, and incubated for 1 hour at room temperature. Then, the phage were removed from the wells, and non-bound phage were washed off using PBST and PBS. Next, 100 μl anti-M13-HRP conjugate (1:5000) in 5% MPBST (incl. 0.05% Tween20) was added and incubated for one hour at room temperature. Another PBST and PBS wash was performed, and 100 μl POD-Substrate was added. A measurement at 370 nm was taken after several minutes in order to quantify the amount of anti-Mac1 phage attached to the antigen in the wells.

Figure 9:
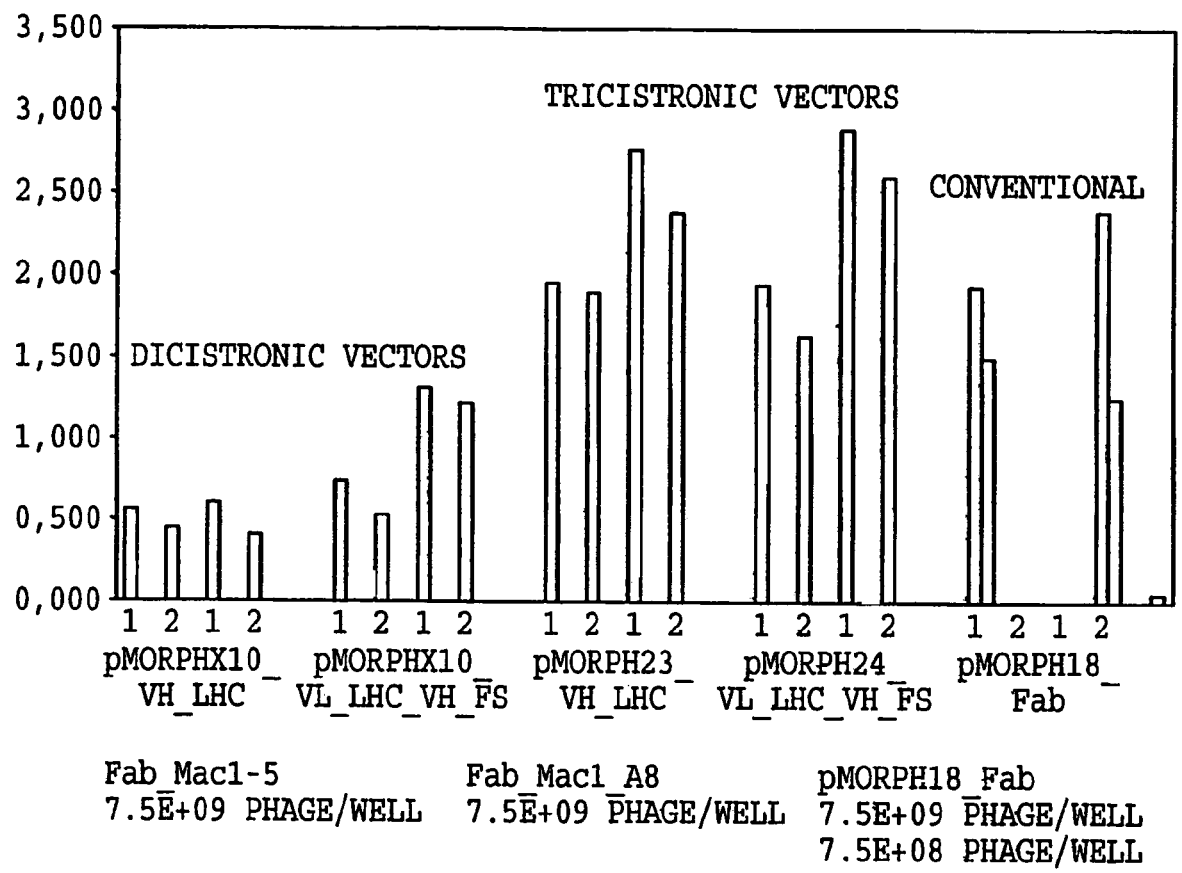
FIG. 9 is a bar graph comparing the functionality and the binding efficiency of Fab-presenting phage of (i) dicistronic Cys display vectors (2-vector system), (ii) tricistronic Cys display vectors, and (iii) dicistronic conventional display vectors in phage ELISA.

FIG. 9 is a bar graph that compares functionality and binding efficiency (functional Fab display) between dicistronic and tricistronic Fab Cys Display vectors in phage ELISA. The improved binding efficiency of the phage resulting from the tricistronic CysDisplay vector versus the dicistronic CysDisplay vector confirms the data of the increased display rates. Bars 1 and 2 represent independent experiments of the same construet. The first two bars for each group represent experiments performed with Fab molecule Mac1-5; the last two bars for each group represent experiments performed with Fab molecule Mac1_A8).

Example 9

Successful Antibody Library Screening Using a Tricistronic Vector System in Cys Display Wells of MaxiSorp™ microtiter plates (NUNC) were coated with 15 μg per antigen (ICAM-1 protein, rabbit myosin, FITC-BSA, estradiol-BSA) dissolved in PBS. Using a tricistronic vector as described in Examples 2A and 2B in conjunction with proprietary MorphoSys phage display and selection techniques, the results provided in Table III were obtained upon screening a MorphoSys HuCAL® Library.

TABLE III

| Antigen | Elution | % primary hits $2^{nd}$ round | % primary hits $3^{rd}$ round | No. of consolidated, specific antibodies |
|---|---|---|---|---|
| ICAM-1 protein | DTT | 0% | 17% | 1 |
| ICAM-1 protein | glycine + TG1 | 0% | 60% | 3 |

TABLE III-continued

| Antigen | Elution | % primary hits $2^{nd}$ round | % primary hits $3^{rd}$ round | No. of consolidated, specific antibodies |
|---|---|---|---|---|
| myosin | DTT | 1% | 29% | 4 |
| myosin | glycine + TG1 | 14% | 19% | 1 |
| FITC-BSA | DTT | 82% | 100% | 6 |
| FITC-BSA | glycine + TG1 | 92% | 87% | 6 |
| estradiol-BSA | DTT | 75% | 67% | 6 |
| estradiol-BSA | glycine + TG1 | 59% | 67% | 3 |

The foregoing data confirm that tricistronic vectors of the invention are effective vehicles for expressing, at a minimum, three functional polypeptide molecules.

Example 10

Construction of pMORPH23 Vector

Figure 5C:
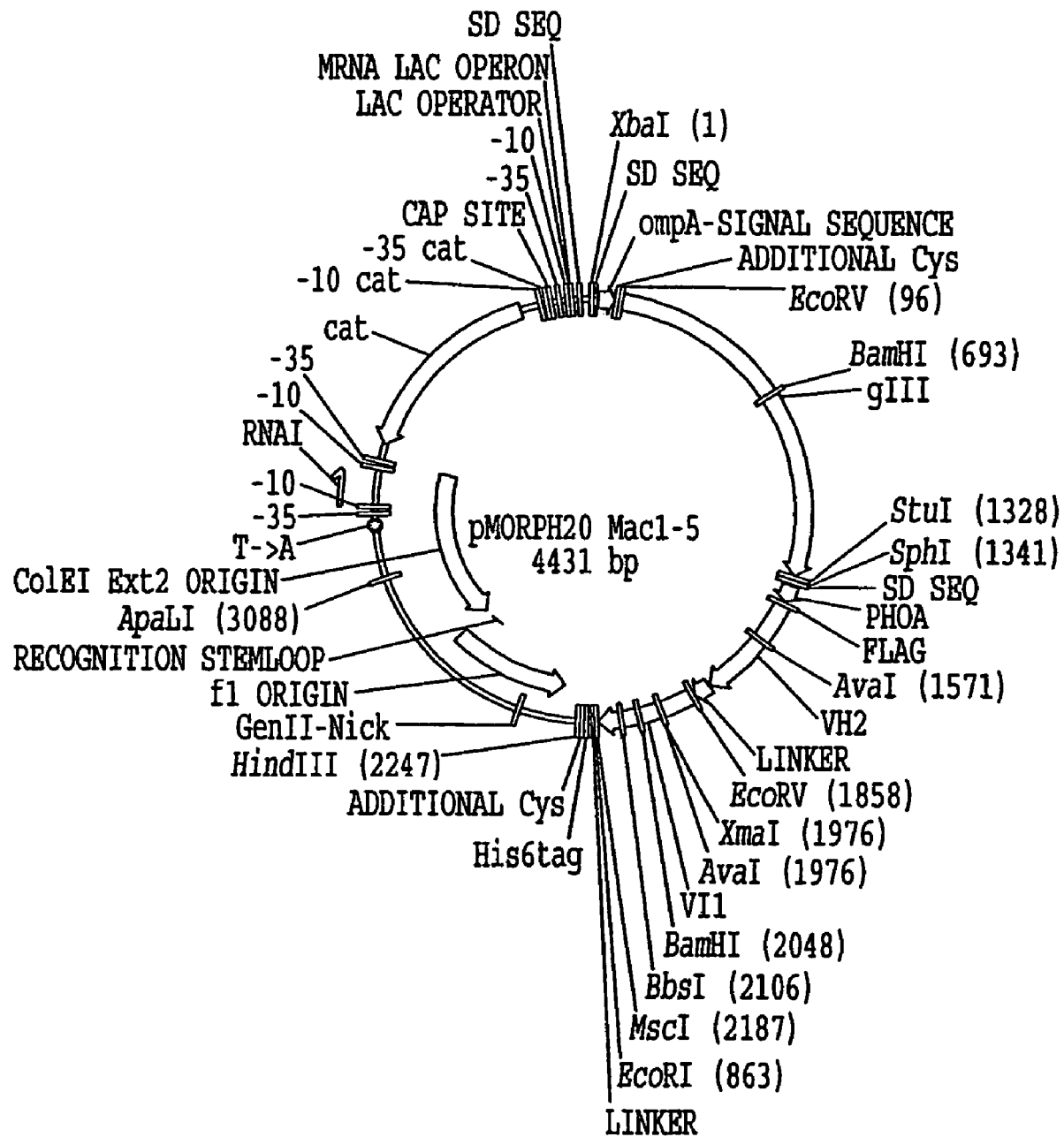
FIG. 5C is a Vector map for pMorph20 Mac1-5

The vector pMORPH23 described here is a derivative of the pCAL vector series (WO 97/08320; Knappik et al., 2000), which is a modified version of the dicistronic expression vector pMORPH20 (example 3). A vector map for pMORPH20 is provided in FIG. 5C and the related nucleic acid sequence is provided in FIG. 5D.

The dicistronic expression vector pMORPH20 was digested with restriction enzymes StuI and MscI, to remove the scFv-expression module. The resulting blunt end cut vector was religated after agarose gel purification and transformed into competent E.coli cells. The intermediate vector product was further modified by replacing the ompA signal-sequence(XbaI and EcoRV digest) by a oligonucleotide cassette preformed by annealing primer pairs A (SEQ. ID NO 1) and B (SEQ. ID NO 2) coding for the gpIII signal sequence and introducing a 5' AccI restriction site and a 3' blunt end.

```
Primer A:
ctagtatacg agggcaaaaa atgaaaaaac tgctgttcgc
gattccgctg gtggtgccgt tctatagcca tagcgactac tgcgac Primer B:
gtcgcagtag tcgctatggc tatagaacgg caccaccagc
ggaatcgcga acagcagttt tttcattttt tgccctcgta ta
```

Figure 2B-1:
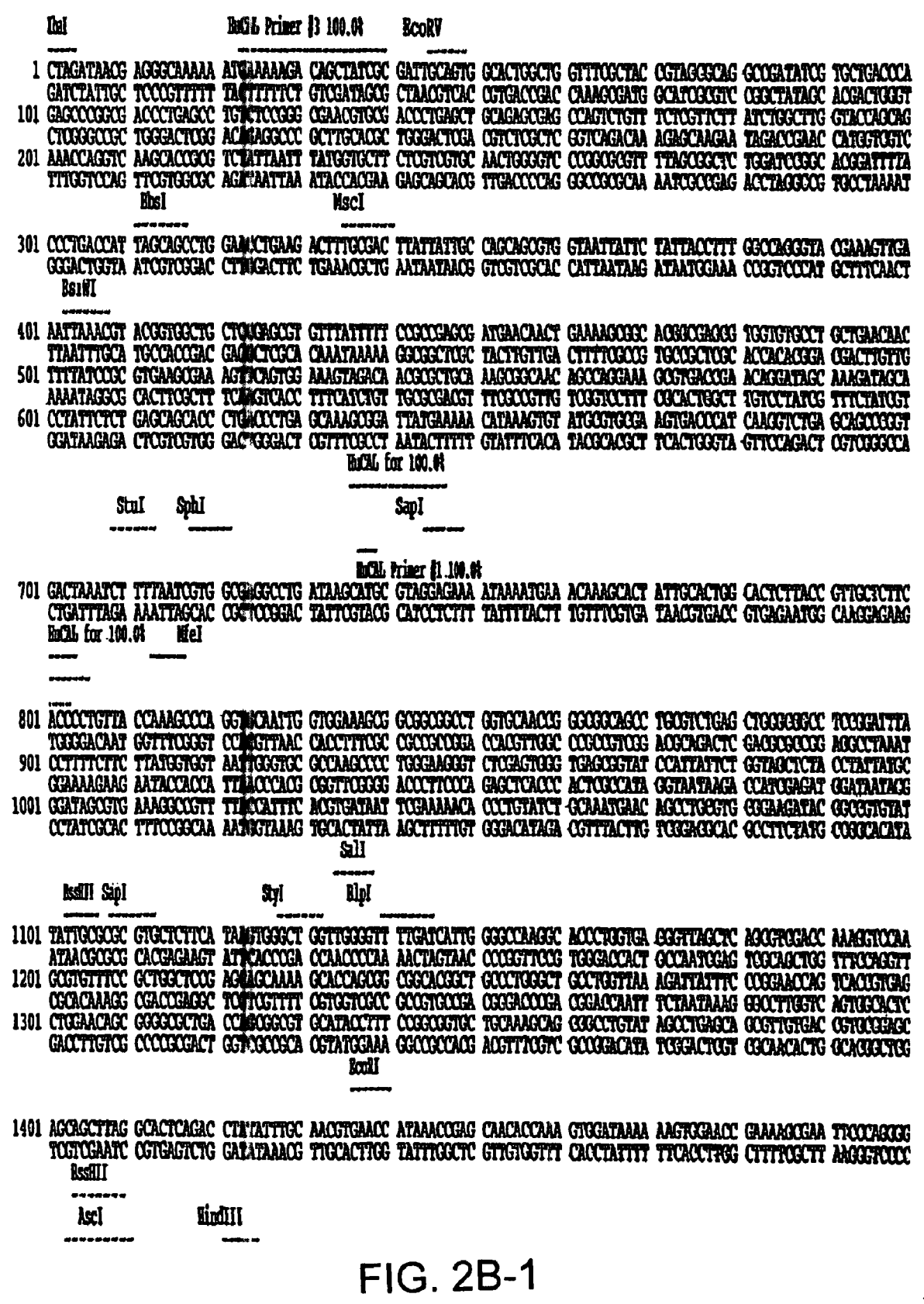

To obtain the final pMORPH23 library cloning vector, an AflII-XbaI-Bla-EcoRI stuffer cassette was introduced by ligation. The stuffer fragment allows efficient cloning of HuCAL Fab fragments by XbaI and EcoRI. An example for tricistronic pMORPH23-HuCAL Fab vector is shown in FIGS. 2A and 2B. All three modules in pMORPH-23 are transcribed as one unit from the lac p/o region.

What is claimed is:

1. A library of tricistronic prokaryotic display vector constructs comprising:
a regulatable prokaryotic promoter;
a first nucleic acid sequence encoding a gIIp phage coat protein or C-terminal domain thereof;
a second nucleic acid sequence encoding a first immunoglobulin (Ig) polypeptide;
a third nucleic acid sequence encoding a second immunoglobulin (Ig) polypeptide;
a nucleic acid sequence encoding a first associating agent fused to or comprised within said nucleic acid sequence encoding the gIIp phage coat protein or C-terminal domain thereof, wherein said first associating agent comprises a cysteine residue; and
a nucleic acid sequence encoding a second associating agent fused to or comprised within said nucleic acid encoding the first immunoglobulin (Ig) polypeptide, wherein said second associating agent comprises a cysteine residue,
wherein said first, second and third nucleic acid sequences are under the control of said promoter, and wherein upon expression of said tricistronic vector, (i) said gIIIp phage coat protein or C-terminal domain thereof and said first Ig polypeptide associate via their respective associating agents and (ii) said first and second Ig polypeptides self-associate.

2. The library of vector constructs according to claim 1, wherein said first and second Ig polypeptides self-associate to form a Fab or other functional Ig fragment.

3. The library of vector constructs according to claim 1, wherein the first and second Ig polypeptides self-associate via non-covalent interactions.

4. The library of vector constructs according to claim 1, further comprising a first secretory signal sequence in the same reading frame as the nucleic acid sequence encoding the first Ig polypeptide.

5. The library of vector constructs according to claim 4, further comprising a second secretory signal sequence in the same reading frame as the nucleic acid sequence encoding the second Ig polypeptide.

6. The library of vector constructs according to claim 5, further comprising a third secretory signal sequence in the same reading frame as the nucleic acid sequence encoding the phage coat protein or C-terminal domain thereof.

7. The library of vector constructs according to claim 1, wherein said vector is a phagemid vector.

8. The library of vector constructs according to claim 1, wherein the associating agents become disassociated in solution upon the addition of a reducing agent.

9. The library of vector constructs according to claim 1, wherein said second associating agent is fused to said first Ig polypeptide via a peptide linker.

10. The library of vector constructs according to claim 6, wherein said first, second, and third secretory signal sequences are prokaryotic signal sequences.

11. The library of vector constructs according to claim 1, further comprising a ribosome binding site positioned 5-primeward of the nucleic acid sequence encoding the second Ig polypeptide.

12. The library of vector constructs according to claim 11, further comprising a ribosome binding site positioned 5-primeward of the nucleic acid sequence encoding the first Ig polypeptide.

13. The library of vector constructs according to claim 12, further comprising a ribosome binding site positioned 5-primeward of the nucleic acid sequence encoding the phage coat protein or C-terminal domain thereof.

* * * * *

UNITED STATES PATENT AND TRADEMARK OFFICE
CERTIFICATE OF CORRECTION

PATENT NO.        : 8,206,977 B2
APPLICATION NO.   : 10/522535
DATED             : June 26, 2012
INVENTOR(S)       : Josef Prassler and Yvonne Stark Page 1 of 1

It is certified that error appears in the above-identified patent and that said Letters Patent is hereby corrected as shown below:

Column 45, line 36, Claim 1, the text "gIIp" should read --gIIIp--.
Column 45, line 44, Claim 1, the text "gIIp" should read --gIIIp--.

Signed and Sealed this
Eighteenth Day of December, 2012

David J. Kappos
*Director of the United States Patent and Trademark Office*

SEQUENCE LISTING

<160> NUMBER OF SEQ ID NOS: 9

<210> SEQ ID NO 1
<211> LENGTH: 86
<212> TYPE: DNA
<213> ORGANISM: artificial sequence
<220> FEATURE:
<223> OTHER INFORMATION: synthetic construct

```
<220> FEATURE:
<221> NAME/KEY: misc_feature
<222> LOCATION: (1)..(86)
<223> OTHER INFORMATION: synthetic construct

<400> SEQUENCE: 1
ctagtatacg agggcaaaaa atgaaaaaac tgctgttcgc gattccgctg gtggtgccgt    60
tctatagcca tagcgactac tgcgac                                        86

<210> SEQ ID NO 2
<211> LENGTH: 82
<212> TYPE: DNA
<213> ORGANISM: artificial sequence
<220> FEATURE:
<223> OTHER INFORMATION: synthetic construct
<220> FEATURE:
<221> NAME/KEY: misc_feature
<222> LOCATION: (1)..(82)
<223> OTHER INFORMATION: synthetic construct

<400> SEQUENCE: 2
gtcgcagtag tcgctatggc tatagaacgg caccaccagc ggaatcgcga acagcagttt    60
tttcattttt tgccctcgta ta                                            82

<210> SEQ ID NO 3
<211> LENGTH: 5049
<212> TYPE: DNA
<213> ORGANISM: artificial sequence
<220> FEATURE:
<223> OTHER INFORMATION: synthetic construct
<220> FEATURE:
<221> NAME/KEY: misc_feature
<222> LOCATION: (1)..(5049)
<223> OTHER INFORMATION: synthetic construct

<400> SEQUENCE: 3
ctagataacg agggcaaaaa atgaaaaaga cagctatcgc gattgcagtg gcactggctg     60
gtttcgctac cgtagcgcag gccgatatcg tgctgaccca gagcccggcg accctgagcc    120
tgtctccggg cgaacgtgcg accctgagct gcagagcgag ccagtctgtt tctcgttctt    180
atctggcttg gtaccagcag aaaccaggtc aagcaccgcg tctattaatt tatggtgctt    240
ctcgtcgtgc aactgggggtc ccggcgcgtt ttagcggctc tggatccggc acggatttta    300
ccctgaccat tagcagcctg aacctgaag actttgcgac ttattattgc cagcagcgtg     360
gtaattattc tattaccttt ggccagggta cgaaagttga aattaaacgt acggtggctg    420
ctccgagcgt gtttattttt ccgccagcg atgaacaact gaaaagcggc acggcgagcg     480
tggtgtgcct gctgaacaac ttttatccgc gtgaagcgaa agttcagtgg aaagtagaca    540
acgcgctgca aagcggcaac agccaggaaa gcgtgaccga acaggatagc aaagatagca    600
cctattctct gagcagcacc ctgaccctga gcaaaagcgga ttatgaaaaa cataaagtgt    660
atgcgtgcga agtgacccat caaggtctga gcagcccggt gactaaatct tttaatcgtg    720
gcgaggcctg ataagcatgc gtaggagaaa ataaaatgaa acaaagcact attgcactgg    780
cactcttacc gttgctcttc acccctgtta ccaaagccca ggtgcaattg gtggaaagcg    840
gcggcggcct ggtgcaaccg ggcggcagcc tgcgtctgag ctgcgcggcc tccggattta    900
cctttttctt ttatgtggt aattgggtgc gccaagcccc tgggaagggt ctcgagtggg    960
tgagcggtat ccattattct ggtagctcta cctattatgc ggatagcgtg aaaggccgtt   1020
ttaccatttc acgtgataat cgaaaaaaca ccctgtatct gcaaatgaac agcctgcgtg   1080
cggaagatac ggccgtgtat tattgcgcgc gtgctcttca taagtgggct ggttgggtt   1140
```

```
ttgatcattg gggccaaggc accctggtga cggttagctc agcgtcgacc aaaggtccaa    1200
gcgtgtttcc gctggctccg agcagcaaaa gcaccagcgg cggcacggct gccctgggct    1260
gcctggttaa agattatttc ccggaaccag tcaccgtgag ctggaacagc ggggcgctga    1320
ccagcggcgt gcatacccttt ccggcggtgc tgcaaagcag cggcctgtat agcctgagca    1380
gcgttgtgac cgtgccgagc agcagcttag cactcagac ctatatttgc aacgtgaacc    1440
ataaaccgag caacaccaaa gtggataaaa aagtggaacc gaaaagcgaa ttcccagggg    1500
ggagcggagg cgcgccgcac catcatcacc atcactgctg ataagcttga cctgtgaagt    1560
gaaaaatggc gcagattgtg cgacattttt tttgtctgcc gtttaatgaa attgtaaacg    1620
ttaatatttt gttaaaattc gcgttaaatt tttgttaaat cagctcattt tttaaccaat    1680
aggccgaaat cggcaaaatc ccttataaat caaaagaata gaccgagata gggttgagtg    1740
ttgttccagt ttggaacaag agtccactat taaagaacgt ggactccaac gtcaaagggc    1800
gaaaaaccgt ctatcagggc gatggcccac tacgagaacc atcaccctaa tcaagttttt    1860
tggggtcgag gtgccgtaaa gcactaaatc ggaaccctaa agggagcccc cgatttagag    1920
cttgacgggg aaagccggcg aacgtggcga aaaggaagg gaagaaagcg aaaggagcgg    1980
gcgctagggc gctggcaagt gtagcggtca cgctgcgcgt aaccaccaca cccgccgcgc    2040
ttaatgcgcc gctacagggc gcgtgctagc catgtgagca aaaggccagc aaaaggccag    2100
gaaccgtaaa aaggccgcgt tgctggcgtt tttccatagg ctccgccccc ctgacgagca    2160
tcacaaaaat cgacgctcaa gtcagaggtg gcgaaacccg acaggactat aaagatacca    2220
ggcgtttccc cctggaagct ccctcgtgcg ctctcctgtt ccgaccctgc cgcttaccgg    2280
atacctgtcc gcctttctcc cttcgggaag cgtggcgctt tctcatagct cacgctgtag    2340
gtatctcagt tcggtgtagg tcgttcgctc caagctgggc tgtgtgcacg aacccccgt    2400 tcagtccgac cgctgcgcct tatccggtaa ctatcgtctt gagtccaacc cggtaagaca    2460
cgacttatcg ccactggcag cagccactgg taacaggatt agcagagcga ggtatgtagg    2520
cggtgctaca gagttcttga agtggtggcc taactacggc tacactagaa gaacagtatt    2580
tggtatctgc gctctgctgt agccagttac cttcggaaaa agagttggta gctcttgatc    2640
cggcaaacaa accaccgctg gtagcggtgg ttttttttgtt tgcaagcagc agattacgcg    2700
cagaaaaaaa ggatctcaag aagatccttt gatcttttct acggggtctg acgctcagtg    2760
gaacgaaaac tcacgttaag ggattttggt cagatctagc accaggcgtt taagggcacc    2820
aataactgcc ttaaaaaaat tacgccccgc cctgccactc atcgcagtac tgttgtaatt    2880
cattaagcat tctgccgaca tggaagccat cacaaacggc atgatgaacc tgaatcgcca    2940
gcggcatcag caccttgtcg ccttgcgtat aatatttgcc catagtgaaa acggggcga    3000 agaagttgtc catattggct acgtttaaat caaaactggt gaaactcacc cagggattgg    3060
ctgagacgaa aaacatattc tcaataaacc ctttagggaa ataggccagg ttttcaccgt    3120
aacacgccac atcttgcgaa tatatgtgta gaaactgccg aaatcgtcg tggtattcac    3180 tccagagcga tgaaaacgtt tcagtttgct catggaaaac ggtgtaacaa gggtgaacac    3240
tatcccatat caccagctca ccgtctttca ttgccatacg gaactccggg tgagcattca    3300
tcaggcgggc aagaatgtga ataaaggccg gataaaactt gtgcttattt ttctttacgg    3360 tcttttaaaaa ggccgtaata tccagctgaa cggtctggtt ataggtacat tgagcaactg    3420
actgaaatgc ctcaaaatgt tctttacgat gccattggga tatatcaacg gtggtatatc    3480
cagtgatttt tttctccatt ttagcttcct tagctcctga aaatctcgat aactcaaaaa    3540
```

```
atacgcccgg tagtgatctt atttcattat ggtgaaagtt ggaacctcac ccgacgtcta    3600
atgtgagtta gctcactcat taggcacccc aggctttaca ctttatgctt ccggctcgta    3660
tgttgtgtgg aattgtgagc ggataacaat ttcacacagg aaacagctat gaccatgatt    3720
acgaatttct agtatacgag ggcaaaaaat gaaaaaactg ctgttcgcga ttccgctggt    3780
ggtgccgttc tatagccata gcgactactg cgacatcgag tttgcagaaa cagttgaaag    3840
ttgtttagca aaaccccata cagaaaattc atttactaac gtctggaaag acgacaaaac    3900
tttagatcgt tacgctaact atgagggctg tctgtggaat gctacaggcg ttgtagtttg    3960
tactggtgac gaaactcagt gttacggtac atgggttcct attgggcttg ctatccctga    4020
aaatgagggt ggtggctctg agggtggcgg ttctgagggt ggcggctctg agggtggcgg    4080
tactaaacct cctgagtacg gtgatacacc tattccgggc tatacttata tcaaccctct    4140
cgacggcact tatccgcctg gtactgagca aaaccccgct aatcctaatc cttctcttga    4200
ggagtctcag cctcttaata ctttcatgtt tcagaataat aggttccgaa ataggcaggg    4260
ggcattaact gtttatacgg gcactgttac tcaaggcact gaccccgtta aaacttatta    4320
ccagtacact cctgtatcat caaaagccat gtatgacgct tactggaacg gtaaattcag    4380
agactgcgct ttccattctg gctttaatga ggatccattc gtttgtgaat atcaaggcca    4440
atcgtctgac ctgcctcaac ctcctgtcaa tgctggcggc ggctctggtg gtggttctgg    4500
tggcggctct gagggtggcg gctctgaggg tggcggttct gagggtggcg gctctgaggg    4560
tggcggttcc ggtggcggct ccggttccgg tgattttgat tatgaaaaaa tggcaaacgc    4620
taataagggg gctatgaccg aaaatgccga tgaaaacgcg ctacagtctg acgctaaagg    4680
caaacttgat tctgtcgcta ctgattacgg tgctgctatc gatggtttca ttggtgacgt    4740
ttccggcctt gctaatggta atggtgctac tggtgatttt gctggctcta attcccaaat    4800
ggctcaagtc ggtgacggtg taattcacc tttaatgaat aatttccgtc aatatttacc    4860
ttctttgcct cagtcggttg aatgtcgccc ttatgtcttt ggcgctggta accatatga    4920 attttctatt gattgtgaca aaataaactt attccgtggt gtctttgcgt ttcttttata    4980
tgttgccacc tttatgtatg tattttcgac gtttgctaac atactgcgta ataaggagtc    5040
ttaagtaat                                                            5049
```

<210> SEQ ID NO 4
<211> LENGTH: 3563
<212> TYPE: DNA
<213> ORGANISM: artificial sequence
<220> FEATURE:
<223> OTHER INFORMATION: synthetic construct
<220> FEATURE:
<221> NAME/KEY: misc_feature
<222> LOCATION: (1)..(3563)
<223> OTHER INFORMATION: synthetic construct

<400> SEQUENCE: 4

```
tctagagcat gcgtaggaga aaataaaatg aaacaaagca ctattgcact ggcactctta     60
ccgttgctct tcacccctgt taccaaagcc gactacaaag atgaagtgca attgaaagaa    120
agcggcccgg ccctggtgaa accgacccaa accctgaccc tgacctgtac cttttccgga    180
tttagcctgt ccacgtctgg cgttggcgtg gctggattc gccagccgcc tgggaaagcc    240
ctcgagtggc tggctctgat tgattgggat gatgataagt attatagcac cagcctgaaa    300
acgcgtctga ccattagcaa agatacttcg aaaaatcagg tggtgctgac tatgaccaac    360
atggacccgg tggatacggc cacctattat tgcgcgcgtt ttgatccttt ttttgattct    420
```

```
tttttttgatt attggggcca aggcaccctg gtgacggtta gctcagcggg tggcggttct    480
ggcggcggtg ggagcggtgg cggtggttct ggcggtggtg gttccgatat cgtgctgacc    540
cagccgcctt cagtgagtgg cgcaccaggt cagcgtgtga ccatctcgtg tagcggcagc    600
agcagcaaca ttggcagcaa ctatgtgagc tggtaccagc agttgcccgg gacggcgccg    660
aaactgctga tttatgataa caaccagcgt ccctcaggcg tgccggatcg ttttagcgga    720
tccaaaagcg gcaccagcgc gagccttgcg attacgggcc tgcaaagcga agacgaagcg    780
gattattatt gccagagcta tgaccagaat gctcttgttg aggtgtttgg cggcggcacg    840
aagttaaccg ttcttggcca ggaattcgag cagaagctga tctctgagga ggatctgaac    900
tagggtggtg gctctggttc cggtgatttt gattatgaaa agatggcaaa cgctaataag    960
ggggctatga ccgaaaatgc cgatgaaaac gcgctacagt ctgacgctaa aggcaaactt   1020
gattctgtcg ctactgatta cggtgctgct atcgatggtt tcattggtga cgtttccggc   1080
cttgctaatg gtaatggtgc tactggtgat tttgctggct ctaattccca aatggctcaa   1140
gtcggtgacg tgataattc acctttaatg aataatttcc gtcaatattt accttccctc   1200
cctcaatcgg ttgaatgtcg ccctttttgtc tttggcgctg gtaaaccata tgaattttct   1260
attgattgtg acaaaataaa cttattccgt ggtgtctttg cgtttctttt atatgttgcc   1320
acctttatgt atgtatttc tacgtttgct aacatactgc gtaataagga gtcttgataa   1380
gcttgacctg tgaagtgaaa atggcgcag attgtgcgac attttttttg tctgccgttt   1440
aatgaaattg taaacgttaa tattttgtta aaattcgcgt taaattttg ttaaatcagc   1500 tcattttta accaataggc cgaaatcggc aaaatccctt ataaatcaaa agaatagacc   1560
gagatagggt tgagtgttgt tccagtttgg aacaagagtc cactattaaa gaacgtggac   1620
tccaacgtca aagggcgaaa aaccgtctat cagggcgatg gcccactacg agaaccatca   1680
ccctaatcaa gttttttggg gtcgaggtgc cgtaaagcac taaatcggaa ccctaaaggg   1740 agccccgat ttagagcttg acggggaaag ccggcgaacg tggcgagaaa ggaagggaag   1800
aaagcgaaag gagcgggcgc tagggcgctg gcaagtgtag cggtcacgct gcgcgtaacc   1860
accacacccg ccgcgcttaa tgcgccgcta cagggcgcgt gctagccatg tgagcaaaag   1920
gccagcaaaa ggccaggaac cgtaaaaagg ccgcgttgct ggcgtttttc cataggctcc   1980
gcccccctga cgagcatcac aaaaatcgac gctcaagtca gaggtggcga aacccgacag   2040
gactataaag ataccaggcg tttccccctg gaagctccct cgtgcgctct cctgttccga   2100
ccctgccgct taccggatac ctgtccgcct ttctccctcc gggaagcgtg gcgctttctc   2160
atagctcacg ctgtaggtat ctcagttcgg tgtaggtcgt tcgctccaag ctgggctgtg   2220
tgcacgaacc ccccgttcag tccgaccgct gcgccttatc cggtaactat cgtcttgagt   2280
ccaacccggt aagacacgac ttatcgccac tggcagcagc cactggtaac aggattagca   2340
gagcgaggta tgtaggcggt gctacagagt tcttgaagtg gtggcctaac tacggctaca   2400
ctagaagaac agtatttggt atctgcgctc tgctgtagcc agttaccttc ggaaaaagag   2460
ttggtagctc ttgatccggc aaacaaacca ccgctggtag cggtggtttt tttgtttgca   2520
agcagcagat tacgcgcaga aaaaaggat ctcaagaaga tcctttgatc ttttctacgg   2580
ggtctgacgc tcagtggaac gaaaactcac gttaagggat tttggtcaga tctagcacca   2640
ggcgtttaag ggcaccaata actgccttaa aaaattacg ccccgccctg ccactcatcg   2700
cagtactgtt gtaattcatt aagcattctg ccgacatgga agccatcaca aacggcatga   2760
tgaacctgaa tcgccagcgg catcagcacc ttgtcgcctt gcgtataata tttgcccata   2820
```

| | |
|---|---|
| gtgaaaacgg gggcgaagaa gttgtccata ttggctacgt ttaaatcaaa actggtgaaa | 2880 |
| ctcacccagg gattggctga gacgaaaaac atattctcaa taaacccttt agggaaatag | 2940 |
| gccaggtttt caccgtaaca cgccacatct tgcgaatata tgtgtagaaa ctgccggaaa | 3000 |
| tcgtcgtggt attcactcca gagcgatgaa aacgtttcag tttgctcatg gaaaacggtg | 3060 |
| taacaagggt gaacactatc ccatatcacc agctcaccgt ctttcattgc catacggaac | 3120 |
| tccgggtgag cattcatcag gcgggcaaga atgtgaataa aggccggata aaacttgtgc | 3180 |
| ttattttct ttacggtctt taaaaaggcc gtaatatcca gctgaacggt ctggttatag | 3240 |
| gtacattgag caactgactg aaatgcctca aaatgttctt tacgatgcca ttgggatata | 3300 |
| tcaacggtgg tatatccagt gatttttttc tccattttag cttccttagc tcctgaaaat | 3360 |
| ctcgataact caaaaaatac gcccggtagt gatcttattt cattatggtg aaagttggaa | 3420 |
| cctcacccga cgtctaatgt gagttagctc actcattagg caccccaggc tttacacttt | 3480 |
| atgcttccgg ctcgtatgtt gtgtggaatt gtgagcggat aacaatttca cacaggaaac | 3540 |
| agctatgacc atgattacga att | 3563 |

<210> SEQ ID NO 5
<211> LENGTH: 4431
<212> TYPE: DNA
<213> ORGANISM: artificial sequence
<220> FEATURE:
<223> OTHER INFORMATION: synthetic construct
<220> FEATURE:
<221> NAME/KEY: misc_feature
<222> LOCATION: (1)..(4431)
<223> OTHER INFORMATION: synthetic construct

<400> SEQUENCE: 5

| | |
|---|---|
| ctagataacg agggcaaaaa atgaaaaaga cagctatcgc gattgcagtg gcactggctg | 60 |
| gtttcgctac cgtagcgcag gccgactact gcgatatcga gtttgcagaa acagttgaaa | 120 |
| gttgtttagc aaaaccccat acagaaaatt catttactaa cgtctggaaa gacgacaaaa | 180 |
| ctttagatcg ttacgctaac tatgagggct gtctgtggaa tgctacaggc gttgtagttt | 240 |
| gtactggtga cgaaactcag tgttacggta catgggttcc tattgggctt gctatccctg | 300 |
| aaaatgaggg tggtggctct gagggtggcg gttctgaggg tggcggctct gagggtggcg | 360 |
| gtactaaacc tcctgagtac ggtgatacac ctattccggg ctatacttat atcaaccctc | 420 |
| tcgacggcac ttatccgcct ggtactgagc aaaaccccgc taatcctaat ccttctcttg | 480 |
| aggagtctca gcctcttaat actttcatgt ttcagaataa taggttccga aataggcagg | 540 |
| gggcattaac tgtttatacg ggcactgtta ctcaaggcac tgaccccgtt aaaacttatt | 600 |
| accagtacac tcctgtatca tcaaaagcca tgtatgacgc ttactggaac ggtaaattca | 660 |
| gagactgcgc tttccattct ggctttaatg aggatccatt cgtttgtgaa tatcaaggcc | 720 |
| aatcgtctga cctgcctcaa cctcctgtca atgctggcgg cggctctggt ggtggttctg | 780 |
| gtggcggctc tgagggtggc ggctctgagg tggcggttc tgagggtggc ggctctgagg | 840 |
| gtggcggttc cggtggcggc tccggttccg gtgattttga ttatgaaaaa atggcaaacg | 900 |
| ctaataaggg ggctatgacc gaaaatgccg atgaaaacgc gctacagtct gacgctaaag | 960 |
| gcaaacttga ttctgtcgct actgattacg gtgctgctat cgatggtttc attggtgacg | 1020 |
| tttccggcct tgctaatggt aatggtgcta ctggtgattt tgctggctct aattcccaaa | 1080 |
| tggctcaagt cggtgacggt gataattcac ctttaatgaa taatttccgt caatatttac | 1140 |
| cttctttgcc tcagtcggtt gaatgtcgcc cttatgtctt tggcgctggt aaaccatatg | 1200 |

```
aattttctat tgattgtgac aaaataaact tattccgtgg tgtctttgcg tttcttttat    1260
atgttgccac ctttatgtat gtattttcga cgtttgctaa catactgcgt aataaggagt    1320
cttaaggcct gataagcatg cgtaggagaa aataaaatga aacaaagcac tattgcactg    1380
gcactcttac cgttgctctt cacccctgtt accaaagccg actacaaaga tgaagtgcaa    1440
ttgaaagaaa gcggcccggc cctggtgaaa ccgacccaaa ccctgaccct gacctgtacc    1500
ttttccggat ttagcctgtc cacgtctggc gttggcgtgg gctggattcg ccagccgcct    1560
gggaaagccc tcgagtggct ggctctgatt gattgggatg atgataagta ttatagcacc    1620
agcctgaaaa cgcgtctgac cattagcaaa gatacttcga aaaatcaggt ggtgctgact    1680
atgaccaaca tggacccggt ggatacggcc acctattatt gcgcgcgttt tgatcctttt    1740
tttgattctt ttttttgatta ttggggccaa ggcaccctgg tgacggttag ctcagcgggt    1800
ggcggttctg gcggcggtgg gagcggtggc ggtggttctg gcggtggtgg ttccgatatc    1860
gtgctgaccc agccgccttc agtgagtggc gcaccaggtc agcgtgtgac catctcgtgt    1920
agcggcagca gcagcaacat tggcagcaac tatgtgagct ggtaccagca gttgcccggg    1980
acggcgccga aactgctgat ttatgataac aaccagcgtc cctcaggcgt gccggatcgt    2040
tttagcggat ccaaaagcgg caccagcgcg agccttgcga ttacgggcct gcaaagcgaa    2100
gacgaagcgg attattattg ccagagctat gaccagaatg ctcttgttga ggtgtttggc    2160
ggcggcacga agttaaccgt tcttggccag gaattcccag gggggagcgg aggcgcgccg    2220
caccatcatc accatcactg ctgataagct tgacctgtga agtgaaaaat ggcgcagatt    2280
gtgcgacatt ttttttgtct gccgtttaat gaaattgtaa acgttaatat tttgttaaaa    2340
ttcgcgttaa attttgtta aatcagctca ttttttaacc aataggccga aatcggcaaa    2400
atcccttata aatcaaaaga atagaccgag atagggttga gtgttgttcc agtttggaac    2460
aagagtccac tattaaagaa cgtggactcc aacgtcaaag ggcgaaaaac cgtctatcag    2520
ggcgatggcc cactacgaga accatcaccc taatcaagtt ttttgggtc gaggtgccgt    2580 aaagcactaa atcggaaccc taaagggagc ccccgattta gagcttgacg gggaaagccg    2640
gcgaacgtgg cgagaaagga agggaagaaa gcgaaaggag cgggcgctag ggcgctggca    2700
agtgtagcgg tcacgctgcg cgtaaccacc acacccgccg cgcttaatgc gccgctacag    2760
ggcgcgtgct agccatgtga gcaaaaggcc agcaaaaggc caggaaccgt aaaaaggccg    2820
cgttgctggc gttttccat aggctccgcc cccctgacga gcatcacaaa aatcgacgct    2880
caagtcagag gtggcgaaac ccgacaggac tataaagata ccaggcgttt ccccctggaa    2940
gctccctcgt gcgctctcct gttccgaccc tgccgcttac cggatacctg tccgcctttc    3000
tcccttcggg aagcgtggcg ctttctcata gctcacgctg taggtatctc agttcggtgt    3060
aggtcgttcg ctccaagctg ggctgtgtgc acgaaccccc cgttcagtcc gaccgctgcg    3120
ccttatccgg taactatcgt cttgagtcca acccggtaag acacgactta tcgccactgg    3180
cagcagccac tggtaacagg attagcagag cgaggtatgt aggcggtgct acagagttct    3240
tgaagtggtg gcctaactac ggctacacta gaagaacagt atttggtatc tgcgctctgc    3300
tgtagccagt taccttcgga aaaagagttg gtagctcttg atccggcaaa caaaccaccg    3360
ctggtagcgg tggttttttt gtttgcaagc agcagattac gcgcagaaaa aaaggatctc    3420
aagaagatcc tttgatcttt tctacggggt ctgacgctca gtggaacgaa aactcacgtt    3480
aagggatttt ggtcagatct agcaccaggc gtttaagggc accaataact gccttaaaaa    3540
aattacgccc cgccctgcca ctcatcgcag tactgttgta attcattaag cattctgccg    3600
```

| | |
|---|---|
| acatggaagc catcacaaac ggcatgatga acctgaatcg ccagcggcat cagcaccttg | 3660 |
| tcgccttgcg tataatattt gcccatagtg aaaacggggg cgaagaagtt gtccatattg | 3720 |
| gctacgttta aatcaaaact ggtgaaactc acccagggat tggctgagac gaaaaacata | 3780 |
| ttctcaataa acccttttagg gaaataggcc aggttttcac cgtaacacgc cacatcttgc | 3840 |
| gaatatatgt gtagaaactg ccggaaatcg tcgtggtatt cactccgag cgatgaaaac | 3900 |
| gtttcagttt gctcatggaa aacggtgtaa caagggtgaa cactatccca tatcaccagc | 3960 |
| tcaccgtctt tcattgccat acggaactcc gggtgagcat tcatcaggcg ggcaagaatg | 4020 |
| tgaataaagg ccggataaaa cttgtgctta tttttctttta cggtctttaa aaaggccgta | 4080 |
| atatccagct gaacggtctg gttataggta cattgagcaa ctgactgaaa tgcctcaaaa | 4140 |
| tgttctttac gatgccattg ggatatatca acggtggtat atccagtgat ttttttctcc | 4200 |
| attttagctt ccttagctcc tgaaaatctc gataactcaa aaaatacgcc cggtagtgat | 4260 |
| cttatttcat tatggtgaaa gttggaacct cacccgacgt ctaatgtgag ttagctcact | 4320 |
| cattaggcac cccaggcttt acactttatg cttccggctc gtatgttgtg tggaattgtg | 4380 |
| agcggataac aatttcacac aggaaacagc tatgaccatg attacgaatt t | 4431 |

```
<210> SEQ ID NO 6
<211> LENGTH: 4154
<212> TYPE: DNA
<213> ORGANISM: artificial sequence
<220> FEATURE:
<223> OTHER INFORMATION: synthetic construct
<220> FEATURE:
<221> NAME/KEY: misc_feature
<222> LOCATION: (1)..(4154)
<223> OTHER INFORMATION: synthetic construct

<400> SEQUENCE: 6
```

| | |
|---|---|
| tctagataac gagggcaaaa aatgaaaaag acagctatcg cgattgcagt ggcactggct | 60 |
| ggtttcgcta ccgtagcgca ggccgatatc gtgctgaccc agccgccttc agtgagtggc | 120 |
| gcaccaggtc agcgtgtgac catctcgtgt agcggcagca gcagcaacat ggcagcaac | 180 |
| tatgtgagct ggtaccagca gttgcccggg acggcgccga aactgctgat ttatgataac | 240 |
| aaccagcgtc cctcaggcgt gccggatcgt tttagcggat ccaaaagcgg caccagcgcg | 300 |
| agccttgcga ttacgggcct gcaaagcgaa gacgaagcgg attattattg ccagagctat | 360 |
| gaccagaatg ctcttgttga ggtgtttggc ggcggcacga agttaaccgt tcttggccag | 420 |
| ccgaaagccg caccgagtgt gacgctgttt ccgccgagca gcgaagaatt gcaggcgaac | 480 |
| aaagcgaccc tggtgtgcct gattagcgac ttttatccgg gagccgtgac agtggcctgg | 540 |
| aaggcagata gcagccccgt caaggcggga gtggagacca ccacaccctc caaacaaagc | 600 |
| aacaacaagt acgcggccag cagctatctg agcctgacgc ctgagcagtg gaagtcccac | 660 |
| agaagctaca gctgccaggt cacgcatgag gggagcaccg tggaaaaaac cgttgcgccg | 720 |
| actgaggcct gataagcatg cgtaggagaa aataaaatga acaaagcac tattgcactg | 780 |
| gcactcttac cgttgctctt caccctgtt accaagcccc aggtgcaatt gaagaaagc | 840 |
| ggccccggccc tggtgaaacc gacccaaacc ctgaccctga cctgtacctt ttccggatt | 900 |
| agcctgtcca cgtctggcgt tggcgtgggc tggattcgcc agccgcctgg gaaagccctc | 960 |
| gagtggctgg ctctgattga ttgggatgat gataagtatt atagcaccag cctgaaaacg | 1020 |
| cgtctgacca tttagcaaaga tacttcgaaa aatcaggtgg tgctgactat gaccaacatg | 1080 |
| gacccggtgg atacggccac ctattattgc gcgcgttttg atcctttttt tgattctttt | 1140 |

```
tttgattatt ggggccaagg caccctggtg acggttagct cagcgtcgac caaaggtcca   1200
agcgtgtttc cgctggctcc gagcagcaaa agcaccagcg gcggcacggc tgccctgggc   1260
tgcctggtta agattatttt cccggaacca gtcaccgtga gctggaacag cggggcgctg   1320
accagcggcg tgcataccct tccggcggtg ctgcaaagca gcggcctgta tagcctgagc   1380
agcgttgtga ccgtgccgag cagcagctta ggcactcaga cctatatttg caacgtgaac   1440
cataaaccga gcaacaccaa agtggataaa aaagtggaac cgaaaagcga attcggggga   1500
gggagcggga gcggtgattt tgattatgaa aagatggcaa cgctaataa ggggctatg    1560 accgaaaatg ccgatgaaaa cgcgctacag tctgacgcta aaggcaaact tgattctgtc   1620
gctactgatt acggtgctgc tatcgatggt ttcattggtg acgtttccgg ccttgctaat   1680
ggtaatggtg ctactggtga ttttgctggc tctaattccc aaatggctca agtcggtgac   1740
ggtgataatt cacctttaat gaataatttc cgtcaatatt taccttccct ccctcaatcg   1800
gttgaatgtc gccctttgt ctttggcgct ggtaaaccat atgaattttc tattgattgt    1860
gacaaaataa acttattccg tggtgtcttt gcgtttcttt tatatgttgc cacctttatg   1920
tatgtatttt ctacgtttgc taacatactg cgtaataagg agtcttgata agcttgacct   1980
gtgaagtgaa aaatggcgca gattgtgcga cattttttt gtctgccgtt taatgaaatt    2040
gtaaacgtta atattttgtt aaaattcgcg ttaaattttt gttaaatcag ctcatttttt   2100
aaccaatagg ccgaaatcgg caaaatccct tataaatcaa agaatagac cgagataggg    2160 ttgagtgttg ttccagtttg gaacaagagt ccactattaa agaacgtgga ctccaacgtc   2220
aaagggcgaa aaaccgtcta tcagggcgat ggcccactac gagaaccatc accctaatca   2280
agttttttgg ggtcgaggtg ccgtaaagca ctaaatcgga accctaaagg agccccccga   2340
tttagagctt gacggggaaa gccggcgaac gtggcgagaa aggaagggaa gaaagcgaaa   2400
ggagcgggcg ctagggcgct ggcaagtgta gcggtcacgc tgcgcgtaac caccacaccc   2460
gccgcgctta atgcgccgct acagggcgcg tgctagccat gtgagcaaaa ggccagcaaa   2520
aggccaggaa ccgtaaaaag gccgcgttgc tggcgttttt ccataggctc cgcccccctg   2580
acgagcatca caaaaatcga cgctcaagtc agaggtggcg aaacccgaca ggactataaa   2640
gataccaggc gtttccccct ggaagctccc tcgtgcgctc tcctgttccg accctgccgc   2700
ttaccggata cctgtccgcc tttctccctt cgggaagcgt ggcgctttct catagctcac   2760
gctgtaggta tctcagttcg gtgtaggtcg ttcgctccaa gctgggctgt gtgcacgaac   2820
cccccgttca gtccgaccgc tgcgccttat ccggtaacta tcgtcttgag tccaacccgg   2880
taagacacga cttatcgcca ctggcagcag ccactggtaa caggattagc agagcgaggt   2940
atgtaggcgg tgctacagag ttcttgaagt ggtggcctaa ctacggctac actagaagaa   3000
cagtatttgg tatctgcgct ctgctgtagc cagttacctt cggaaaaaga gttggtagct   3060
cttgatccgg caaacaaacc accgctggta gcggtggttt ttttgtttgc aagcagcaga   3120
ttacgcgcag aaaaaaagga tctcaagaag atcctttgat cttttctacg ggtctgacg    3180 ctcagtggaa cgaaaactca cgttaaggga ttttggtcag atctagcacc aggcgtttaa   3240
gggcaccaat aactgcctta aaaaaattac gccccgccct gccactcatc gcagtactgt   3300
tgtaattcat taagcattct gccgacatgg aagccatcac aaacggcatg atgaacctga   3360
atcgccagcg gcatcagcac cttgtcgcct tgcgtataat atttgcccat agtgaaaacg   3420
gggcgaagaa gttgtccat attggctacg tttaaatcaa aactggtgaa actcacccag   3480
ggattggctg agacgaaaaa catattctca ataaaccctt tagggaaata ggccaggttt   3540
```

| | | |
|---|---|---|
| tcaccgtaac acgccacatc ttgcgaatat atgtgtagaa actgccggaa atcgtcgtgg | 3600 |
| tattcactcc agagcgatga aaacgtttca gtttgctcat ggaaaacggt gtaacaaggg | 3660 |
| tgaacactat cccatatcac cagctcaccg tctttcattg ccatacgaaa ctccgggtga | 3720 |
| gcattcatca ggcgggcaag aatgtgaata aaggccggat aaaacttgtg cttattttc | 3780 |
| tttacggtct ttaaaaaggc cgtaatatcc agctgaacgg tctggttata ggtacattga | 3840 |
| gcaactgact gaaatgcctc aaaatgttct ttacgatgcc attgggatat atcaacggtg | 3900 |
| gtatatccag tgatttttt ctccatttta gcttccttag ctcctgaaaa tctcgataac | 3960 |
| tcaaaaaata cgcccggtag tgatcttatt tcattatggt gaaagttgga acctcacccg | 4020 |
| acgtctaatg tgagttagct cactcattag gcaccccagg ctttacactt tatgcttccg | 4080 |
| gctcgtatgt tgtgtggaat tgtgagcgga taacaatttc acacaggaaa cagctatgac | 4140 |
| catgattacg aatt | 4154 |

<210> SEQ ID NO 7
<211> LENGTH: 5079
<212> TYPE: DNA
<213> ORGANISM: artificial sequence
<220> FEATURE:
<223> OTHER INFORMATION: synthetic construct
<220> FEATURE:
<221> NAME/KEY: misc_feature
<222> LOCATION: (1)..(5079)
<223> OTHER INFORMATION: synthetic construct

<400> SEQUENCE: 7

| | | |
|---|---|---|
| cagcagttgc ccgggacggc gccgaaactg ctgatttatg ataacaacca gcgtccctca | 60 |
| ggcgtgccgg atcgttttag cggatccaaa agcggcacca gcgcgagcct tgcgattacg | 120 |
| ggcctgcaaa gcgaagacga agcggattat tattgccaga gctatgacca gaatgctctt | 180 |
| gttgaggtgt ttggcggcgg cacgaagtta accgttcttg gccagccgaa agccgcaccg | 240 |
| agtgtgacgc tgttccgcc gagcagcgaa gaattgcagg cgaacaaagc gaccctggtg | 300 |
| tgcctgatta gcgacttta tccgggagcc gtgacagtgg cctggaaggc agatagcagc | 360 |
| cccgtcaagg cgggagtgga gaccaccaca ccctccaaac aaagcaacaa caagtacgcg | 420 |
| gccagcagct atctgagcct gacgcctgag cagtggaagt cccacagaag ctacagctgc | 480 |
| caggtcacgc atgaggggag caccgtggaa aaaaccgttg cgccgactga ggcctctcca | 540 |
| gggggggagcg gaggcgcgcc gcaccatcat caccatcact gctgataata tgcatgcgta | 600 |
| ggagaaaata aaatgaaaca aagcactatt gcactggcac tcttaccgtt gctcttcacc | 660 |
| cctgttacca agcccaggt gcaattgaaa gaaagcggcc cggccctggt gaaaccgacc | 720 |
| caaaccctga ccctgacctg taccttttcc ggatttagcc tgtccacgtc tggcgttggc | 780 |
| gtgggctgga ttcgccagcc gcctgggaaa gccctcgagt ggctggctct gattgattgg | 840 |
| gatgatgata agtattatag caccagcctg aaaacgcgtc tgaccattag caaagatact | 900 |
| tcgaaaaatc aggtggtgct gactatgacc aacatggacc cggtggatac ggccaccta | 960 |
| tattgcgcgc gttttgatcc tttttttgat tcttttttg attattgggg ccaaggcacc | 1020 |
| ctggtgacgg ttagctcagc gtcgaccaaa ggtccaagcg tgtttccgct ggctccgagc | 1080 |
| agcaaaagca ccagcggcgg cacggctgcc ctgggctgcc tggttaaaga ttattccccg | 1140 |
| gaaccagtca ccgtgagctg gaacagcggg gcgctgacca gcggcgtgca tacctttccg | 1200 |
| gcggtgctgc aaagcagcgg cctgtatagc ctgagcagcg ttgtgaccgt gccgagcagc | 1260 |
| agcttaggca ctcagaccta tatttgcaac gtgaaccata aaccgagcaa caccaaagtg | 1320 |

```
gataaaaaag tggaaccgaa aagcgaattc gactataaag atgacgatga caaaggcgcg    1380
ccgtggagcc acccgcagtt tgaaaaatga taagcttgac ctgtgaagtg aaaaatggcg    1440
cagattgtgc gacatttttt ttgtctgccg tttaattaaa gggggggggg ggccggcctg    1500
ggggggggtg tacatgaaat tgtaaacgtt aatattttgt taaaattcgc gttaaatttt    1560
tgttaaatca gctcattttt taaccaatag gccgaaatcg gcaaatccc ttataaatca     1620 aaagaataga ccgagatagg gttgagtgtt gttccagttt ggaacaagag tccactatta    1680
aagaacgtgg actccaacgt caaagggcga aaaaccgtct atcagggcga tggcccacta    1740
cgagaaccat caccctaatc aagttttttg gggtcgaggt gccgtaaagc actaaatcgg    1800
aaccctaaag ggagccccg atttagagct tgacggggaa agccggcgaa cgtggcgaga     1860
aaggaaggga agaaagcgaa aggagcgggc gctagggcgc tggcaagtgt agcggtcacg    1920
ctgcgcgtaa ccaccacacc cgccgcgctt aatgcgccgc tacagggcgc gtgctagact    1980 agtgttaaa ccggaccggg gggggcttaa gtgggctgc aaaacaaaac ggcctcctgt      2040
caggaagccg cttttatcgg gtagcctcac tgcccgcttt ccagtcggga aacctgtcgt    2100
gccagctgca tcagtgaatc ggccaacgcg cggggagagg cggtttgcgt attgggagcc    2160
agggtggttt ttcttttcac cagtgagacg ggcaacagct gattgcccttc accgcctgg    2220 ccctgagaga gttgcagcaa gcggtccacg ctggtttgcc ccagcaggcg aaaatcctgt    2280
ttgatggtgg tcagcggcgg gatataacat gagctgtcct cggtatcgtc gtatcccact    2340
accgagatgt ccgcaccaac gcgcagcccg gactcggtaa tggcacgcat tgcgcccagc    2400
gccatctgat cgttggcaac cagcatcgca gtgggaacga tgccctcatt cagcatttgc    2460
atggtttgtt gaaaccgga catggcactc cagtcgcctt cccgttccgc tatcggctga     2520
atttgattgc gagtgagata tttatgccag ccagccagac gcagacgcgc cgagacagaa    2580
cttaatgggc cagctaacag cgcgatttgc tggtggccca atgcgaccag atgctccacg    2640
cccagtcgcg taccgtcctc atgggagaaa ataatactgt tgatgggtgt ctggtcagag    2700
acatcaagaa ataacgccgg aacattagtg caggcagctt ccacagcaat agcatcctgg    2760
tcatccagcg gatagttaat aatcagccca ctgacacgtt gcgcgagaag attgtgcacc    2820
gccgctttac aggcttcgac gccgcttcgt tctaccatcg acacgaccac gctggcaccc    2880
agttgatcgg cgcgagattt aatcgccgcg acaatttgcg acggcgcgtg cagggccaga    2940
ctggaggtgg caacgccaat cagcaacgac tgtttgcccg ccagttgttg tgccacgcgg    3000
ttaggaatgt aattcagctc cgccatcgcc gcttccactt ttcccgcgt tttcgcagaa     3060 acgtggctgg cctggttcac cacgcgggaa acggtctgat aagagacacc ggcatactct    3120
gcgacatcgt ataacgttac tggtttcaca ttcaccaccc tgaattgact ctcttccggg    3180
cgctatcatg ccataccgcg aaaggttttg cgccattcga tgctagccat gtgagcaaaa    3240
ggccagcaaa aggccaggaa ccgtaaaaag gccgcgttgc tggcgttttt ccataggctc    3300
cgcccccctg acgagcatca aaaaatcga cgctcaagtc agaggtggcg aaacccgaca     3360
ggactataaa gataccaggc gtttcccct ggaagctccc tcgtgcgctc tcctgttccg     3420
accctgccgc ttaccggata cctgtccgcc tttctccctt cgggaagcgt ggcgctttct    3480
catagctcac gctgtaggta tctcagttcg gtgtaggtc ttcgctccaa gctgggctgt     3540
gtgcacgaac cccccgttca gcccgaccgc tgcgccttat ccggtaacta tcgtcttgag    3600
tccaacccgg taagacacga cttatcgcca ctggcagcag ccactggtaa caggattagc    3660
agagcgaggt atgtaggcgg tgctacagag ttcttgaagt ggtggcctaa ctacggctac    3720
```

| | |
|---|---|
| actagaagaa cagtatttgg tatctgcgct ctgctgtagc cagttacctt cggaaaaaga | 3780 |
| gttggtagct cttgatccgg caaacaaacc accgctggta gcggtggttt ttttgtttgc | 3840 |
| aagcagcaga ttacgcgcag aaaaaaagga tctcaagaag atcctttgat cttttctacg | 3900 |
| gggtctgacg ctcagtggaa cgaaaactca cgttaaggga ttttggtcag atctagcacc | 3960 |
| aggcgtttaa gggcaccaat aactgcctta aaaaaattac gccccgccct gccactcatc | 4020 |
| gcagtactgt tgtaattcat taagcattct gccgacatgg aagccatcac aaacggcatg | 4080 |
| atgaacctga atcgccagcg gcatcagcac cttgtcgcct tgcgtataat atttgcccat | 4140 |
| agtgaaaacg ggggcgaaga agttgtccat attggctacg tttaaatcaa aactggtgaa | 4200 |
| actcacccag ggattggctg agacgaaaaa catattctca ataaacccct tagggaaata | 4260 |
| ggccaggttt tcaccgtaac acgccacatc ttgcgaatat atgtgtagaa actgccggaa | 4320 |
| atcgtcgtgg tattcactcc agagcgatga aaacgtttca gtttgctcat ggaaaacggt | 4380 |
| gtaacaaggg tgaacactat cccatatcac cagctcaccg tctttcattg ccatacgaaa | 4440 |
| ctccgggtga gcattcatca ggcgggcaag aatgtgaata aaggccggat aaaacttgtg | 4500 |
| cttattttc tttacggtct ttaaaaaggc cgtaatatcc agctgaacgg tctggttata | 4560 |
| ggtacattga gcaactgact gaaatgcctc aaaatgttct ttacgatgcc attgggatat | 4620 |
| atcaacggtg gtatatccag tgatttttt ctccatttta gcttccttag ctcctgaaaa | 4680 |
| tctcgataac tcaaaaaata cgcccggtag tgatcttatt tcattatggt gaaagttgga | 4740 |
| acctcacccg acgtctaatg tgagttagct cactcattag gcaccccagg ctttacactt | 4800 |
| tatgcttccg gctcgtatgt tgtgtggaat tgtgagcgga taacaatttc acacaggaaa | 4860 |
| cagctatgac catgattacg aatttctaga taacgagggc aaaaaatgaa aaagacagct | 4920 |
| atcgcgattg cagtggcact ggctggtttc gctaccgtag cgcaggccga tatcgtgctg | 4980 |
| acccagccgc cttcagtgag tggcgcacca ggtcagcgtg tgaccatctc gtgtagcggc | 5040 |
| agcagcagca acattggcag caactatgtg agctggtac | 5079 |

<210> SEQ ID NO 8
<211> LENGTH: 5016
<212> TYPE: DNA
<213> ORGANISM: artificial sequence
<220> FEATURE:
<223> OTHER INFORMATION: synthetic construct
<220> FEATURE:
<221> NAME/KEY: misc_feature
<222> LOCATION: (1)..(5016)
<223> OTHER INFORMATION: synthetic construct

<400> SEQUENCE: 8

| | |
|---|---|
| gcgacatcgt ataacgttac tggtttcaca ttcaccaccc tgaattgact ctcttccggg | 60 |
| cgctatcatg ccataccgcg aaaggttttg cgccattcga tgctagccat gtgagcaaaa | 120 |
| ggccagcaaa aggccaggaa ccgtaaaaag gccgcgttgc tggcgttttt ccataggctc | 180 |
| cgcccccctg acgagcatca aaaaatcga cgctcaagtc agaggtggcg aaacccgaca | 240 |
| ggactataaa gataccaggc gtttccccct ggaagctccc tcgtgcgctc tcctgttccg | 300 |
| accctgccgc ttaccggata cctgtccgcc tttctccctt cgggaagcgt ggcgctttct | 360 |
| catagctcac gctgtaggta tctcagttcg gtgtaggtcg ttcgctccaa gctgggctgt | 420 |
| gtgcacgaac cccccgttca gcccgaccgc tgcgccttat ccggtaacta tcgtcttgag | 480 |
| tccaacccgg taagacacga cttatcgcca ctggcagcag ccactggtaa caggattagc | 540 |
| agagcgaggt atgtaggcgg tgctacagag ttcttgaagt ggtggcctaa ctacggctac | 600 |

```
actagaagaa cagtatttgg tatctgcgct ctgctgtagc cagttacctt cggaaaaaga    660
gttggtagct cttgatccgg caaacaaacc accgctggta gcggtggttt ttttgtttgc    720
aagcagcaga ttacgcgcag aaaaaaagga tctcaagaag atcctttgat cttttctacg    780
gggtctgacg ctcagtggaa cgaaaactca cgttaaggga ttttggtcag atctagcacc    840
aggcgtttaa gggcaccaat aactgcctta aaaaaattac gccccgccct gccactcatc    900
gcagtactgt tgtaattcat taagcattct gccgacatgg aagccatcac aaacggcatg    960
atgaacctga atcgccagcg gcatcagcac cttgtcgcct tgcgtataat atttgcccat   1020
agtgaaaacg ggggcgaaga agttgtccat attggctacg tttaaatcaa actggtgaa    1080 actcacccag ggattggctg agacgaaaaa catattctca ataaacccct tagggaaata   1140
ggccaggttt tcaccgtaac acgccacatc ttgcgaatat atgtgtagaa actgccggaa   1200
atcgtcgtgg tattcactcc agagcgatga aacgtttca gtttgctcat ggaaaacggt   1260
gtaacaaggg tgaacactat cccatatcac cagctcaccg tctttcattg ccatacggaa   1320
ctccgggtga gcattcatca ggcgggcaag aatgtgaata aaggccggat aaaacttgtg   1380
cttatttttc tttacggtct ttaaaaaggc cgtaatatcc agctgaacgg tctggttata   1440
ggtacattga gcaactgact gaaatgcctc aaaatgttct ttacgatgcc attgggatat   1500
atcaacggtg gtatatccag tgatttttt ctccatttta gcttccttag ctcctgaaaa   1560
tctcgataac tcaaaaaata cgcccggtag tgatcttatt tcattatggt gaaagttgga   1620
acctcacccg acgtctaatg tgagttagct cactcattag gcaccccagg ctttacactt   1680
tatgcttccg gctcgtatgt tgtgtggaat tgtgagcgga taacaatttc acacaggaaa   1740
cagctatgac catgattacg aatttctaga taacgagggc aaaaaatgaa aaagacagct   1800
atcgcgattg cagtggcact ggctggtttc gctaccgtag cgcaggccga tatcgtgctg   1860
acccagccgc cttcagtgag tggcgcacca ggtcagcgtg tgaccatctc gtgtagcggc   1920
agcagcagca acattggcag caactatgtg agctggtacc agcagttgcc cgggacggcg   1980
ccgaaactgc tgatttatga taacaaccag cgtccctcag gcgtgccgga tcgttttagc   2040
ggatccaaaa gcggcaccag cgcgagcctt gcgattacgg gcctgcaaag cgaagacgaa   2100
gcggattatt attgccagag ctatgaccag aatgctcttg ttgaggtgtt tggcggcggc   2160
acgaagttaa ccgttcttgg ccagccgaaa gccgcaccga gtgtgacgct gtttccgccg   2220
agcagcgaag aattgcaggc gaacaaagcg accctggtgt gcctgattag cgactttat   2280 ccgggagccg tgacagtggc ctggaaggca gatagcagcc ccgtcaaggc gggagtggag   2340
accaccacac cctccaaaca aagcaacaac aagtacgcgg ccagcagcta tctgagcctg   2400
acgcctgagc agtggaagtc ccacagaagc tacagctgcc aggtcacgca tgagggagc    2460 accgtggaaa aaaccgttgc gccgactgag gcctgataag catgcgtagg agaaaataaa   2520
atgaaacaaa gcactattgc actggcactc ttaccgttgc tcttcaccc tgttaccaaa   2580 gcccaggtgc aattgaaaga aagcggcccg gccctggtga accgaccca aaccctgacc   2640 ctgacctgta ccttttccgg atttagcctg tccacgtctg gcgttggcgt gggctggatt   2700
cgccagccgc tgggaaagc cctcgagtgg ctggctctga ttgattggga tgatgataag   2760
tattatagca ccagcctgaa aacgcgtctg accattagca aagatacttc gaaaaatcag   2820
gtggtgctga ctatgaccaa catggacccg gtggatacgg ccacctatta ttgcgcgcgt   2880
tttgatcctt tttttgattc tttttttgat tattggggcc aaggcaccct ggtgacggtt   2940
agctcagcgt cgaccaaagg tccaagcgtg tttccgctgg ctccgagcag caaaagcacc   3000
```

```
agcggcggca cggctgccct gggctgcctg gttaaagatt atttcccgga accagtcacc    3060
gtgagctgga acagcggggc gctgaccagc ggcgtgcata cctttccggc ggtgctgcaa    3120
agcagcggcc tgtatagcct gagcagcgtt gtgaccgtgc cgagcagcag cttaggcact    3180
cagacctata tttgcaacgt gaaccataaa ccgagcaaca ccaaagtgga taaaaaagtg    3240
gaaccgaaaa gcgaattccc aggggggagc ggaggcgcgc cgcaccatca tcaccatcac    3300
tgctgataag cttgacctgt gaagtgaaaa atggcgcaga ttgtgcgaca ttttttttgt    3360
ctgccgttta attaaagggg ggggggggcc ggcctggggg ggggtgtaca tgaaattgta    3420
aacgttaata ttttgttaaa attcgcgtta aattttttgtt aaatcagctc attttttaac    3480
caataggccg aaatcggcaa atcccttat aaatcaaaag aatagaccga gatagggttg    3540
agtgttgttc cagtttggaa caagagtcca ctattaaaga acgtggactc caacgtcaaa    3600
gggcgaaaaa ccgtctatca gggcgatggc ccactacgag aaccatcacc ctaatcaagt    3660
tttttggggt cgaggtgccg taaagcacta atcggaacc ctaaagggag cccccgattt    3720
agagcttgac ggggaaagcc ggcgaacgtg gcgagaaagg aagggaagaa agcgaaagga    3780
gcgggcgcta gggcgctggc aagtgtagcg gtcacgctgc gcgtaaccac cacacccgcc    3840
gcgcttaatg cgccgctaca gggcgcgtgc tagactagtg tttaaaccgg accgggggg     3900 ggcttaagtg ggctgcaaaa caaaacggcc tcctgtcagg aagccgcttt tatcgggtag    3960
cctcactgcc cgctttccag tcgggaaacc tgtcgtgcca gctgcatcag tgaatcggcc    4020
aacgcgcggg gagaggcggt ttgcgtattg ggagccaggg tggttttct tttcaccagt     4080 gagacgggca acagctgatt gcccttcacc gcctggccct gagagagttg cagcaagcgg    4140
tccacgctgg tttgccccag caggcgaaaa tcctgtttga tggtggtcag cggcgggata    4200
taacatgagc tgtcctcggt atcgtcgtat cccactaccg agatgtccgc accaacgcgc    4260
agcccggact cggtaatggc acgcattgcg cccagcgcca tctgatcgtt ggcaaccagc    4320
atcgcagtgg gaacgatgcc ctcattcagc atttgcatgg tttgttgaaa accggacatg    4380
gcactccagt cgccttcccg ttccgctatc ggctgaattt gattgcgagt gagatattta    4440
tgccagccag ccagacgcag acgcgccgag acagaactta atgggccagc taacagcgcg    4500
atttgctggt ggcccaatgc gaccagatgc tccacgccca gtcgcgtacc gtcctcatgg    4560
gagaaaataa tactgttgat gggtgtctgg tcagagacat caagaaataa cgccggaaca    4620
ttagtgcagg cagcttccac agcaaatagc tcctggtcat ccagcggata gttaataatc    4680
agcccactga cacgttgcgc gagaagattg tgcaccgccg ctttacaggc ttcgacgccg    4740
cttcgttcta ccatcgacac gaccacgctg cacccagtt gatcggcgcg agatttaatc     4800
gccgcgacaa tttgcgacgg cgcgtgcagg gccagactgg aggtggcaac gccaatcagc    4860
aacgactgtt tgcccgccag ttgttgtgcc acgcggttag gaatgtaatt cagctccgcc    4920
atcgccgctt ccactttttc ccgcgttttc gcagaaacgt ggctggcctg gttcaccacg    4980
cgggaaacgg tctgataaga gacaccggca tactct                              5016
```

<210> SEQ ID NO 9
<211> LENGTH: 5729
<212> TYPE: DNA
<213> ORGANISM: artificial sequence
<220> FEATURE:
<223> OTHER INFORMATION: synthetic construct
<220> FEATURE:
<221> NAME/KEY: misc_feature
<222> LOCATION: (1)..(5729)
<223> OTHER INFORMATION: synthetic construct

```
<400> SEQUENCE: 9
caagctgtga ccgtctccgg gagctgcatg tgtcagaggt tttcaccgtc atcaccgaaa      60
cgcgcgaggc agctgcggta aagctcatca gcgtggtcgt gaagcgattc acagatgtct     120
gcctgttcat ccgcgtccag ctcgttgagt ttctccagaa gcgttaatgt ctggcttctg     180
ataaagcggg ccatgttaag gcggttttt tcctgtttgg tcactgatgc ctccgtgtaa      240
gggggatttc tgttcatggg ggtaatgata ccgatgaaac gagagaggat gctcacgata     300
cgggttactg atgatgaaca tgcccggtta ctggaacgtt gtgagggtaa acaactggcg     360
gtatggatgc ggcgggacca gagaaaaatc actcagggtc aatgccagcg cttcgttaat     420
acagatgtag gtgttccaca gggtagccag cagcatcctg cgatgcagat ccggaacata     480
atggtgcagg cgctgactt ccgcgttcc agactttacg aaacacggaa accgaagacc       540
attcatgttg ttgctcaggt cgcagacgtt ttgcagcagc agtcgcttca cgttcgctcg     600
cgtatcggtg attcattctg ctaaccagta aggcaacccc gccagcctag ccgggtcctc     660
aacgacagga gcacgatcat gcgcacccgt ggccaggacc caacgctgcc cgagatgcgc     720
cgcgtgcggc tgctggagat ggcggacgcg atggatatgt tctgccaagg gttggtttgc     780
gcattcacag ttctccgcaa gaattgattg gctccaattc ttggagtggt gaatccgtta     840
gcgaggtgcc gccggcttcc attcaggtcg aggtggcccg gctccatgca ccgcgacgca     900
acgcggggag gcagacaagg tatagggcgg cgcctacaat ccatgccaac ccgttccatg     960
tgctcgccga gcggcataa atcgccgtga cgatcagcgg tccagtgatc gaagttaggc    1020
tggtaagagc cgcgagcgat ccttgaagct gtccctgatg gtcgtcatct acctgcctgg    1080
acagcatggc ctgcaacgcg gcatcccga tgccgccgga agcgagaaga atcataatgg     1140
ggaaggccat ccagcctcgc gtcgcgaacg ccagcaagac gtagcccagc gcgtcggccg    1200
ccatgccggc gataatggcc tgcttctcgc cgaaacgttt ggtggcggga ccagtgacga    1260
aggcttgagc gagggcgtgc aagattccga ataccgcaag cgacaggccg atcatcgtcg    1320
cgctccagcg aaagcggtcc tcgccgaaaa tgacccagag cgctgccggc acctgtccta    1380
cgagttgcat gataaagaag acagtcataa gtgcggcgac gatagtcatg ccccgcgccc    1440
accggaagga gctgactggg ttgaaggctc tcaagggcat cggtcgacgc tctcccttat    1500
gcgactcctg cattaggaag cagcccagta gtaggttgag gccgttgagc accgccgccg    1560
caaggaatgg tgcatgcaag gagatggcgc ccaacagtcc cccggccacg gggcctgcca    1620
ccatacccac gccgaaacaa gcgctcatga gcccgaagtg gcgagcccga tcttccccat    1680
cggtgatgtc ggcgatatag gcgccagcaa ccgcacctgt ggcgccggtg atgcggcca     1740
cgatgcgtcc ggcgtagagg atccacagga cgggtgtggt cgccatgatc gcgtagtcga    1800
tagtggctcc aagtagcgaa gcgagcagga ctgggcggcg gccaaagcgg tcggacagtg    1860
ctccgagaac gggtgcgcat agaaattgca tcaacgcata tagcgctagc ctgaggccag    1920
tttgctcagg ctctccccgt ggaggtaata attgctcgac cgataaaagc ggcttcctga    1980
caggaggccg ttttgttttg cagcccacct caacgcaatt aatgtgagtt agctcactca    2040
ttaggcaccc caggctttac actttatgct tccggctcgt atgttgtgtg gaattgtgag    2100
cggataacaa tttcacacag gaaacagcta tgaccatgat tacgaattc tagataacga     2160
gggcaaaaaa tgaaaaagac agctatcgcg attgcagtgg cactggctgg tttcgctacc    2220
gtagcgcagg ccgactactg cgatatcgaa ttcgagaaa cagttgaaag ttgtttagca     2280
aaaccccata cagaaaattc atttactaac gtctggaaag acgacaaaac tttagatcgt    2340
```

```
tacgctaact atgagggctg tctgtggaat gctacaggcg ttgtagtttg tactggtgac    2400
gaaactcagt gttacggtac atgggttcct attgggcttg ctatccctga aaatgagggt    2460
ggtggctctg agggtggcgg ttctgagggt ggcggctctg agggtggcgg tactaaacct    2520
cctgagtacg gtgatacacc tattccgggc tatacttata tcaaccctct cgacggcact    2580
tatccgcctg gtactgagca aaaccccgct aatcctaatc cttctcttga ggagtctcag    2640
cctcttaata ctttcatgtt tcagaataat aggttccgaa ataggcaggg ggcattaact    2700
gtttatacgg gcactgttac tcaaggcact gaccccgtta aaacttatta ccagtacact    2760
cctgtatcat caaaagccat gtatgacgct tactggaacg gtaaattcag agactgcgct    2820
ttccattctg gctttaatga ggatccattc gtttgtgaat atcaaggcca atcgtctgac    2880
ctgcctcaac ctcctgtcaa tgctggcggc ggctctggtg gtggttctgg tggcggctct    2940
gagggtggcg ctctgaggg tggcggttct gagggtggcg ctctgaggg tggcggttcc    3000 ggtggcggct ccggttccgg tgattttgat tatgaaaaaa tggcaaacgc taataagggg    3060
gctatgaccg aaaatgccga tgaaaacgcg ctacagtctg acgctaaagg caaacttgat    3120
tctgtcgcta ctgattacgg tgctgctatc gatggtttca ttggtgacgt ttccggcctt    3180
gctaatggta atggtgctac tggtgatttt gctggctcta attcccaaat ggctcaagtc    3240
ggtgacggtg ataattcacc tttaatgaat aatttccgtc aatatttacc ttctttgcct    3300
cagtcggttg aatgtcgccc ttatgtcttt ggcgctggta accatatga attttctatt    3360 gattgtgaca aaataaactt attccgtggt gtctttgcgt ttcttttata tgttgccacc    3420
tttatgtatg tattttcgac gtttgctaac atactgcgta ataaggagtc ttaagcttat    3480
cgatgataag ctgtcaaaca tgagaattct tgaagacgaa agggcctcgt gatacgccta    3540
tttttatagg ttaatgtcat gataataatg gtttcttaga cgtcaggtgg cacttttcgg    3600
ggaaatgtgc gcggaacccc tatttgttta ttttctaaa tacattcaaa tatgtatccg    3660
ctcatgagac aataaccctg ataaatgctt caataatatt gaaaaaggaa gagtatgagt    3720
attcaacatt tccgtgtcgc ccttattccc ttttttgcgg catttgcct tcctgttttt    3780 gctcacccag aaacgctggt gaaagtaaaa gatgctgaag atcagttggg tgcacgagtg    3840
ggttacatcg aactggatct caacagcggt aagatccttg agagttttcg ccccgaagaa    3900
cgttttccaa tgatgagcac ttttaaagtt ctgctatgtg gcgcggtatt atcccgtgtt    3960
gacgccgggc aagagcaact cggtcgccgc atacactatt ctcagaatga cttggttgag    4020
tactcaccag tcacagaaaa gcatcttacg gatggcatga cagtaagaga attatgcagt    4080
gctgccataa ccatgagtga taacactgcg gccaacttac ttctgacaac gatcggagga    4140
ccgaaggagc taaccgcttt tttgcacaac atgggggatc atgtaactcg ccttgatcgt    4200
tgggaaccgg agctgaatga agccatacca aacgacgagc gtgacaccac gatgcctgca    4260
gcaatggcaa caacgttgcg caaactatta actggcgaac tacttactct agcttcccgg    4320
caacaattaa tagactggat ggaggcggat aaagttgcag gaccacttct gcgctcggcc    4380
cttccggctg gctggtttat tgctgataaa tctggagccg gtgagcgtgg gtctcgcggt    4440
atcattgcag cactggggcc agatggtaag ccctcccgta tcgtagttat ctacacgacg    4500
gggagtcagg caactatgga tgaacgaaat agacagatcg ctgagatagg tgcctcactg    4560
attaagcatt ggtaactgtc agaccaagtt tactcatata cttagat tgatttaaaa    4620 cttcattttt aatttaaaag gatctaggtg aagatccttt ttgataatct catgaccaaa    4680
atcccttaac gtgagttttc gttccactga gcgtcagacc ccgtagaaaa gatcaaagga    4740
```

```
tcttcttgag atccttttt  tctgcgcgta atctgctgct tgcaaacaaa aaaaccaccg    4800
ctaccagcgg tggtttgttt gccggatcaa gagctaccaa ctcttttcc  gaaggtaact    4860 ggcttcagca gagcgcagat accaaatact gtccttctag tgtagccgta gttaggccac    4920
cacttcaaga actctgtagc accgcctaca tacctcgctc tgctaatcct gttaccagtg    4980
gctgctgcca gtggcgataa gtcgtgtctt accgggttgg actcaagacg atagttaccg    5040
gataaggcgc agcggtcggg ctgaacgggg ggttcgtgca cacagcccag cttggagcga    5100
acgacctaca ccgaactgag atacctacag cgtgagctat gagaaagcgc cacgcttccc    5160
gaagggagaa aggcggacag gtatccggta agcggcaggg tcggaacagg agagcgcacg    5220
agggagcttc caggggaaa  cgcctggtat ctttatagtc ctgtcgggtt tcgccacctc    5280
tgacttgagc gtcgattttt gtgatgctcg tcagggggge ggagcctatg gaaaaacgcc    5340
agcaacgcgg cctttttacg gttcctggcc ttttgctggc cttttgctca catgttcttt    5400
cctgcgttat cccctgattc tgtggataac cgtattaccg cctttgagtg agctgatacc    5460
gctcgccgca gccgaacgac cgagcgcagc gagtcagtga gcgaggaagc ggaagagcgc    5520
ctgatgcggt attttctcct tacgcatctg tgcggtattt cacaccgcat atggtgcact    5580
ctcagtacaa tctgctctga tgccgcatag ttaagccagt atacactccg ctatcgctac    5640
gtgactgggt catggctgcg ccccgacacc cgccaacacc cgctgacgcg ccctgacggg    5700
cttgtctgct cccggcatcc gcttacaga                                      5729
```